(12) United States Patent
Guillemont et al.

(10) Patent No.: US 9,133,167 B2
(45) Date of Patent: Sep. 15, 2015

(54) ANTIBACTERIAL QUINOLINE DERIVATIVES

(71) Applicant: JANSSEN PHARMACEUTICA NV, Beerse (BE)

(72) Inventors: Jerome Emile Georges Guillemont, Val de Reuil Cedex (FR); Magali Madeleine Simone Motte, Val de Reuil Cedex (FR); David Francis Alain Lancois, Val de Reuil Cedex (FR); Wendy Mia Albert Balemans, Beerse (BE)

(73) Assignee: Janssen Pharmaceutica NV, Beerse (BE)

( * ) Notice: Subject to any disclaimer, the term of this patent is extended or adjusted under 35 U.S.C. 154(b) by 0 days.

(21) Appl. No.: 14/391,045

(22) PCT Filed: Apr. 26, 2013

(86) PCT No.: PCT/EP2013/058703
§ 371 (c)(1),
(2) Date: Oct. 7, 2014

(87) PCT Pub. No.: WO2013/160435
PCT Pub. Date: Oct. 31, 2013

(65) Prior Publication Data
US 2015/0065502 A1    Mar. 5, 2015

(30) Foreign Application Priority Data
Apr. 27, 2012  (EP) .................... 12165934

(51) Int. Cl.
*C07D 401/06* (2006.01)
*A61K 31/4709* (2006.01)
*C07D 401/14* (2006.01)
*A61K 31/5377* (2006.01)
*A61K 45/06* (2006.01)
*C07D 405/14* (2006.01)

(52) U.S. Cl.
CPC .......... *C07D 401/14* (2013.01); *A61K 31/4709* (2013.01); *A61K 31/5377* (2013.01); *A61K 45/06* (2013.01); *C07D 401/06* (2013.01); *C07D 405/14* (2013.01)

(58) Field of Classification Search
CPC .. C07D 401/06; C07D 401/14; C07D 405/14; A61K 31/4709; A61K 31/5377; A61K 45/06
See application file for complete search history.

(56) References Cited

U.S. PATENT DOCUMENTS 5,965,572 A    10/1999  Ellis et al.

FOREIGN PATENT DOCUMENTS

| WO | WO 00/34265 A2 | 6/2000 |
|---|---|---|
| WO | WO 2004/011436 A1 | 2/2004 |
| WO | 2005/070924 * | 8/2005 |
| WO | WO 2005/070430 A1 | 8/2005 |
| WO | WO 2005/070924 A1 | 8/2005 |
| WO | WO 2005/075428 A1 | 8/2005 |
| WO | WO 2005/117875 A1 | 12/2005 |
| WO | WO 2005/123081 A2 | 12/2005 |
| WO | WO 2006/035051 A1 | 4/2006 |
| WO | WO 2006/067048 A1 | 6/2006 |
| WO | WO 2006/131519 A1 | 12/2006 |
| WO | WO 2007/000434 A1 | 1/2007 |
| WO | WO 2007/000435 A1 | 1/2007 |
| WO | WO 2007/000436 A1 | 1/2007 |
| WO | WO 2007/014885 A1 | 2/2007 |

(Continued)

OTHER PUBLICATIONS

Guillaume, M., et al., "Process Development of the Synthetic Route to R116301", Organic Process Research & Development 2007), vol. 11, pp. 1079-1086.
Ye, X., et al., "Discovery of a Novel Sulfonamide-Pyrazolopiperiine Series as Potent and Efficacious γ-Secretase Inhibitors", Bioorganic & Medicinal Chemistry Letters, (2010), vol. 20, pp. 2195-2199.
Zurenko, G., et al., "In Vitro Activities of U-100592 and U-100766, Novel Oxazolidinone Antibacterial Agents", Antimicrobial Agents and Chemotherapy (1996), pp. 839-845.
International Search Report mailed Jun. 11, 2013 for Application No. PCT/EP2013/058703.
International Search Report mailed Jun. 13, 2013, for Application No. PCT/EP2013/058697.

*Primary Examiner* — D M Seaman
(74) *Attorney, Agent, or Firm* — Thomas J. Dodd

(57) ABSTRACT

The present invention relates to novel substituted quinoline derivatives according to the general Formula (Ia) or Formula (Ib):

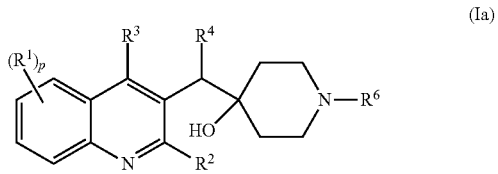

(Ia)

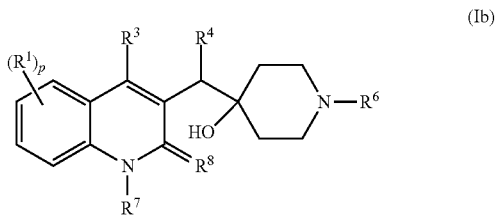

(Ib)

including any stereochemically isomeric form thereof, a pharmaceutically acceptable salt thereof, a N-oxide form thereof or a solvate thereof. The claimed compounds are useful for the treatment of a bacterial infection. Also claimed is a composition comprising a pharmaceutically acceptable carrier and, as active ingredient, a therapeutically effective amount of the claimed compounds, the use of the claimed compounds or compositions for the manufacture of a medicament for the treatment of a bacterial infection and a process for preparing the claimed compounds.

25 Claims, No Drawings

(56) References Cited

FOREIGN PATENT DOCUMENTS

| WO | WO 2007/014934 A2 | 2/2007 |
| WO | WO 2007/014940 A2 | 2/2007 |
| WO | WO 2007/014941 A2 | 2/2007 |
| WO | WO 2008/068266 A1 | 6/2008 |
| WO | WO 2008/068267 A1 | 6/2008 |
| WO | WO 2008/068268 A1 | 6/2008 |
| WO | WO 2008/068269 A1 | 6/2008 |
| WO | WO 2008/068270 A1 | 6/2008 |
| WO | WO 2008/068272 A2 | 6/2008 |

\* cited by examiner

ANTIBACTERIAL QUINOLINE DERIVATIVES

CROSS-REFERENCE TO RELATED APPLICATIONS

The present application claims priority of the benefits of the filing of Application Nos. EP 12165934.6 filed Apr. 27, 2012, and PCT/EP2013/058703 (WO2013/160435) filed Apr. 26, 2013. The complete disclosures of the aforementioned related patent applications are hereby incorporated herein by reference for all purposes.

The present invention relates to novel substituted quinoline derivatives useful for the treatment of bacterial diseases, including but not limited to diseases caused by pathogenic mycobacteria such as *Mycobacterium tuberculosis, M. bovis, M. leprae, M. avium* and *M. marinum*, or pathogenic Staphylococci or Streptococci.

BACKGROUND OF THE INVENTION

*Mycobacterium tuberculosis* is the causative agent of tuberculosis (TB), a serious and potentially fatal infection with a world-wide distribution. Estimates from the World Health Organization indicate that more than 8 million people contract TB each year, and 2 million people die from tuberculosis yearly. In the last decade, TB cases have grown 20% worldwide with the highest burden in the most impoverished communities. If these trends continue, TB incidence will increase by 41% in the next twenty years. Fifty years since the introduction of an effective chemotherapy, TB remains after AIDS, the leading infectious cause of adult mortality in the world. Complicating the TB epidemic is the rising tide of multi-drug-resistant strains, and the deadly symbiosis with HIV. People who are HIV-positive and infected with TB are 30 times more likely to develop active TB than people who are HIV-negative and TB is responsible for the death of one out of every three people with HIV/AIDS worldwide.

Existing approaches to treatment of tuberculosis all involve the combination of multiple agents. For example, the regimen recommended by the U.S. Public Health Service is a combination of isoniazid, rifampicin and pyrazinamide for two months, followed by isoniazid and rifampicin alone for a further four months. These drugs are continued for a further seven months in patients infected with HIV. For patients infected with multi-drug resistant strains of *M. tuberculosis*, agents such as ethambutol, streptomycin, kanamycin, amikacin, capreomycin, ethionamide, cycloserine, ciprofoxacin and ofloxacin are added to the combination therapies. There exists no single agent that is effective in the clinical treatment of tuberculosis, nor any combination of agents that offers the possibility of therapy of less than six months' duration.

There is a high medical need for new drugs that improve current treatment by enabling regimens that facilitate patient and provider compliance. Shorter regimens and those that require less supervision are the best way to achieve this. Most of the benefit from treatment comes in the first 2 months, during the intensive, or bactericidal, phase when four drugs are given together; the bacterial burden is greatly reduced, and patients become noninfectious. The 4- to 6-month continuation, or sterilizing, phase is required to eliminate persisting bacilli and to minimize the risk of relapse. A potent sterilizing drug that shortens treatment to 2 months or less would be extremely beneficial. Drugs that facilitate compliance by requiring less intensive supervision also are needed. Obviously, a compound that reduces both the total length of treatment and the frequency of drug administration would provide the greatest benefit.

Complicating the TB epidemic is the increasing incidence of multi-drug-resistant strains or MDR-TB. Up to four percent of all cases worldwide are considered MDR-TB—those resistant to the most effective drugs of the four-drug standard, isoniazid and rifampin. MDR-TB is lethal when untreated and cannot be adequately treated through the standard therapy, so treatment requires up to 2 years of "second-line" drugs. These drugs are often toxic, expensive and marginally effective. In the absence of an effective therapy, infectious MDR-TB patients continue to spread the disease, producing new infections with MDR-TB strains. There is a high medical need for a new drug with a new mechanism of action, which is likely to demonstrate activity against drug resistant, in particular MDR strains.

The term "drug resistant" as used hereinbefore or hereinafter is a term well understood by the person skilled in microbiology. A drug resistant *Mycobacterium* is a *Mycobacterium* which is no longer susceptible to at least one previously effective drug; which has developed the ability to withstand antibiotic attack by at least one previously effective drug. A drug resistant strain may relay that ability to withstand to its progeny. Said resistance may be due to random genetic mutations in the bacterial cell that alters its sensitivity to a single drug or to different drugs. MDR tuberculosis is a specific form of drug resistant tuberculosis due to a bacterium resistant to at least isoniazid and rifampicin (with or without resistance to other drugs), which are at present the two most powerful anti-TB drugs. Thus, whenever used hereinbefore or hereinafter "drug resistant" includes multi drug resistant.

Another factor in the control of the TB epidemic is the problem of latent TB. In spite of decades of tuberculosis (TB) control programs, about 2 billion people are infected by *M. tuberculosis*, though asymptomatically. About 10% of these individuals are at risk of developing active TB during their lifespan. The global epidemic of TB is fuelled by infection of HIV patients with TB and rise of multi-drug resistant TB strains (MDR-TB). The reactivation of latent TB is a high risk factor for disease development and accounts for 32% deaths in HIV infected individuals. To control TB epidemic, the need is to discover new drugs that can kill dormant or latent bacilli. The dormant TB can get reactivated to cause disease by several factors like suppression of host immunity by use of immunosuppressive agents like antibodies against tumor necrosis factor α or interferon-γ. In case of HIV positive patients the only prophylactic treatment available for latent TB is two-three months regimens of rifampicin, pyrazinamide. The efficacy of the treatment regime is still not clear and furthermore the length of the treatments is an important constraint in resource-limited environments. Hence there is a drastic need to identify new drugs, which can act as chemoprophylactic agents for individuals harboring latent TB bacilli.

The tubercle bacilli enter healthy individuals by inhalation; they are phagocytosed by the alveolar macrophages of the lungs. This leads to potent immune response and formation of granulomas, which consist of macrophages infected with *M. tuberculosis* surrounded by T cells. After a period of 6-8 weeks the host immune response causes death of infected cells by necrosis and accumulation of caseous material with certain extracellular bacilli, surrounded by macrophages, epitheloid cells and layers of lymphoid tissue at the periphery. In case of healthy individuals, most of the mycobacteria are killed in these environments but a small proportion of bacilli still survive and are thought to exist in a non-replicating, hypometabolic state and are tolerant to killing by anti-TB drugs like isoniazid. These bacilli can remain in the altered physiological environments even for individual's lifetime without showing any clinical symptoms of disease. However, in 10% of the cases these latent bacilli may reactivate to cause disease. One of the hypothesis about development of these persistent bacteria is patho-physiological environment in human lesions namely, reduced oxygen tension, nutrient limitation, and acidic pH. These factors have been postulated to render these bacteria phenotypically tolerant to major anti-mycobacterial drugs.

In addition to the management of the TB epidemic, there is the emerging problem of resistance to first-line antibiotic agents. Some important examples include penicillin-resistant *Streptococcus pneumoniae*, vancomycin-resistant enterococci, methicillin-resistant *Staphylococcus aureus*, multi-resistant salmonellae.

The consequences of resistance to antibiotic agents are severe. Infections caused by resistant microbes fail to respond to treatment, resulting in prolonged illness and greater risk of death. Treatment failures also lead to longer periods of infectivity, which increase the numbers of infected people moving in the community and thus exposing the general population to the risk of contracting a resistant strain infection. Hospitals are a critical component of the antimicrobial resistance problem worldwide. The combination of highly susceptible patients, intensive and prolonged antimicrobial use, and cross-infection has resulted in infections with highly resistant bacterial pathogens.

Self-medication with antimicrobials is another major factor contributing to resistance. Self-medicated antimicrobials may be unnecessary, are often inadequately dosed, or may not contain adequate amounts of active drug.

Patient compliance with recommended treatment is another major problem. Patients forget to take medication, interrupt their treatment when they begin to feel better, or may be unable to afford a full course, thereby creating an ideal environment for microbes to adapt rather than be killed.

Because of the emerging resistance to multiple antibiotics, physicians are confronted with infections for which there is no effective therapy. The morbidity, mortality, and financial costs of such infections impose an increasing burden for health care systems worldwide.

Therefore, there is a high need for new compounds to treat bacterial infections, especially mycobacterial infections including drug resistant and latent mycobacterial infections, and also other bacterial infections especially those caused by resistant bacterial strains.

WO2004/011436, WO2005/070924, WO2005/070430, WO2005/075428 and WO2007/014885 disclose certain substituted quinoline derivatives having activity against Mycobacteria, in particular against *Mycobacterium tuberculosis*. WO2005/117875 describes substituted quinoline derivatives having activity against resistant Mycobacterial strains. WO2006/067048 describes substituted quinoline derivatives having activity against latent tuberculosis. One particular compound of these substituted quinoline derivatives is described in Science (2005), 307, 223-227 and its mode of action is described in WO2006/035051.

WO2006/131519, WO2007/000434, WO2007/000435, WO2007/000436, WO2007/014934, WO2007/014940 and WO2007/014941 disclose certain substituted quinoline derivatives having activity against bacteria such as *Staphylococcus* and *Streptococcus*.

WO2008/068266, WO2008/068267, WO2008/068268, WO2008/068269, WO2008/068270 and WO2008/068272 disclose certain substituted quinoline derivatives having activity against Mycobacteria, in particular against *Mycobacterium tuberculosis*, and also against bacteria such as *Staphylococcus* and *Streptococcus*.

Other substituted quinolines are disclosed in U.S. Pat. No. 5,965,572 (The United States of America) for treating antibiotic resistant infections and in WO00/34265 to inhibit the growth of bacterial microorganisms.

The purpose of the present invention is to provide novel compounds, in particular substituted quinoline derivatives, having the property of inhibiting bacterial growth especially of mycobacteria but also of other bacteria such as Streptococci and Staphylococci and the compounds are therefore useful for the treatment of bacterial diseases, particularly those diseases caused by pathogenic bacteria such as *Streptococcus pneumonia*, *Staphylococcus aureus* or *Mycobacterium tuberculosis* (including the latent disease and including drug resistant *M. tuberculosis* strains), *M. bovis*, *M. leprae*, *M. avium* and *M. marinum*.

SUMMARY OF THE INVENTION

The present invention relates to novel substituted quinoline derivatives according to formula (Ia) or (Ib):

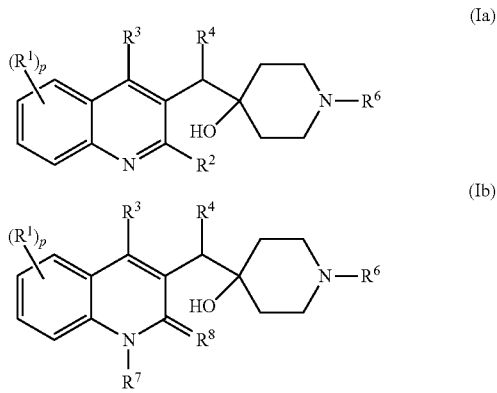

including any stereochemically isomeric form thereof, wherein p is an integer equal to 1, 2, 3 or 4;

$R^1$ is hydrogen, cyano, cyano$C_{1-6}$alkyl, formyl, carboxyl, halo, $C_{1-6}$alkyl, $C_{2-6}$alkenyl, $C_{2-6}$alkynyl, polyhalo$C_{1-6}$alkyl, hydroxy, hydroxy$C_{1-6}$alkyl, $C_{1-6}$alkyloxy, $C_{1-6}$alkylthio, $C_{1-6}$alkylthio$C_{1-6}$alkyl, —C=N—$OR^{11}$, amino, mono or di($C_{1-6}$alkyl)amino, amino$C_{1-6}$alkyl, mono or di($C_{1-6}$alkyl)amino$C_{1-6}$alkyl, $C_{1-6}$alkylcarbonylamino $C_{1-6}$alkyl, $R^{9b}R^{10b}$N—C(=O)—, aryl$C_{1-6}$alkyl, arylcarbonyl, $R^{9a}R^{10a}$N—$C_{1-6}$alkyl, di(aryl)$C_{1-6}$alkyl, aryl, $C_{3-6}$cycloalkyl, $R^{9a}R^{10a}$N—, $R^{9a}R^{10a}$N—C(=O)—, $C_{1-4}$alkyl-S(=O)$_2$—, or Het;

$R^2$ is hydrogen, $C_{1-6}$alkyloxy, aryl, aryloxy, hydroxy, mercapto, $C_{1-6}$alkyloxy$C_{1-6}$alkyloxy, $C_{1-6}$alkylthio, mono or di($C_{1-6}$alkyl)amino, amino, pyrrolidino or a radical of formula

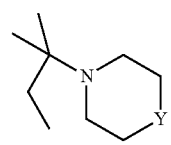

wherein Y is CH$_2$, O, S, NH or N—C$_{1-6}$alkyl;

R$^3$ is hydrogen, halo, C$_{1-6}$alkyl, aryl or Het;

R$^4$ is aryl$^1$ or Het;

R$^6$ is hydrogen, C$_{1-6}$alkyl, arylC$_{1-6}$alkyl, Het, HetC$_{1-6}$alkyl or —C(=NH)—NH$_2$;

R$^7$ is hydrogen, C$_{1-6}$alkyl or mono or di(C$_{1-6}$alkyl)amino;

R$^8$ is oxo; or

R$^7$ and R$^8$ together form the radical —CH=CH—N=;

R$^{9a}$ and R$^{10a}$ together with the nitrogen atom to which they are attached form a radical selected from the group consisting of pyrrolidinyl, piperidinyl, piperazinyl, morpholinyl, 4-thiomorpholinyl, 2,3-dihydroisoindol-1-yl, thiazolidin-3-yl, 1,2,3,6-tetrahydropyridyl, hexahydro-1H-azepinyl, hexahydro-1H-1,4-diazepinyl, hexahydro-1,4-oxazepinyl, 1,2,3,4-tetrahydroisoquinolin-2-yl, pyrrolinyl, pyrrolyl, imidazolidinyl, pyrazolidinyl, 2-imidazolinyl, 2-pyrazolinyl, imidazolyl, pyrazolyl, triazolyl, pyridinyl, pyridazinyl, pyrimidinyl, pyrazinyl and triazinyl, each radical being optionally substituted with 1, 2, 3 or 4 substituents, each substituent being independently selected from C$_{1-6}$alkyl, polyhaloC$_{1-6}$alkyl, halo, arylC$_{1-6}$alkyl, hydroxy, C$_{1-6}$alkyloxy, amino, mono- or di(C$_{1-6}$alkyl)amino, C$_{1-6}$alkylthio, C$_{1-6}$alkylthioC$_{1-6}$alkyl, aryl, pyridyl or pyrimidinyl;

R$^{9b}$ and R$^{10b}$ each independently represent hydrogen, C$_{1-6}$alkyl, aryl or Het;

R$^{11}$ is hydrogen or C$_{1-6}$alkyl;

aryl is a homocycle selected from phenyl, naphthyl, acenaphthyl or tetrahydronaphthyl, each being optionally substituted with 1, 2 or 3 substituents, each substituent being independently selected from hydroxy, hydroxyC$_{1-6}$alkyl, halo, cyano, cyanoC$_{1-6}$alkyl, nitro, amino, mono- or di(C$_{1-6}$alkyl)amino, C$_{1-6}$alkyl, C$_{2-6}$alkenyl optionally substituted with phenyl, polyhaloC$_{1-6}$alkyl, C$_{1-6}$alkyloxy, C$_{1-6}$alkyloxyC$_{1-6}$alkyl, polyhaloC$_{1-6}$alkyloxy, carboxyl, C$_{1-6}$alkyloxycarbonyl, aminocarbonyl, morpholinyl or mono- or di(C$_{1-6}$alkyl)aminocarbonyl;

aryl$^1$ is a homocycle selected from phenyl, naphthyl, acenaphthyl or tetrahydronaphthyl, each being optionally substituted with 1, 2 or 3 substituents, each substituent being independently selected from hydroxy, hydroxyC$_{1-6}$alkyl, halo, cyano, cyanoC$_{1-6}$alkyl, nitro, amino, mono- or di(C$_{1-6}$alkyl)amino, C$_{1-6}$alkyl, polyhaloC$_{1-6}$alkyl, C$_{1-6}$alkyloxy, C$_{1-6}$alkyloxyC$_{1-6}$alkyl, C$_{1-6}$alkylthio, polyhaloC$_{1-6}$alkyloxy, carboxyl, C$_{1-6}$alkyloxycarbonyl, aminocarbonyl, Het, mono- or di(C$_{1-6}$alkyl)aminocarbonyl, or C$_{1-4}$alkyl-S(=O)$_2$—;

Het is a monocyclic heterocycle selected from N-phenoxypiperidinyl, piperidinyl, piperazinyl, morpholinyl, 4-thiomorpholinyl, pyrrolyl, pyrazolyl, imidazolyl, furanyl, thienyl, oxazolyl, isoxazolyl, thiazolyl, isothiazolyl, pyridinyl, pyrimidinyl, pyrazinyl or pyridazinyl; or a bicyclic heterocycle selected from quinolinyl, quinoxalinyl, indolyl, benzimidazolyl, benzoxazolyl, benzisoxazolyl, benzothiazolyl, benzisothiazolyl, benzofuranyl, benzothienyl, 2,3-dihydrobenzo[1,4]dioxinyl or benzo[1,3]dioxolyl; each monocyclic and bicyclic heterocycle being optionally substituted with 1, 2 or 3 substituents, each substituent being independently selected from halo, hydroxy, C$_{1-6}$alkyl, C$_{1-6}$alkyloxy or arylC$_{1-6}$alkyl;

the N-oxides thereof, the pharmaceutically acceptable salts thereof or the solvates thereof.

Whenever used herein, the term "compounds of formula (Ia) or (Ib)" or "compounds according to the invention" is meant to also include their pharmaceutically acceptable salts or their N-oxide forms or their solvates.

The compounds of formula (Ia) and (Ib) are interrelated in that e.g. a compound according to formula (Ib), with R$^8$ equal to oxo and R$^7$ equal to hydrogen, is the tautomeric equivalent of a compound according to formula (Ia) with R$^2$ equal to hydroxy (keto-enol tautomerism).

In the definition of Het, it is meant to include all the possible isomeric forms of the heterocycles, for instance, pyrrolyl comprises 1H-pyrrolyl and 2H-pyrrolyl.

The aryl, aryl$^1$ or Het listed in the definitions of the substituents of the compounds of formula (Ia) or (Ib) (see for instance R$^4$ or R$^6$) as mentioned hereinbefore or hereinafter may be attached to the remainder of the molecule of formula (Ia) or (Ib) through any ring carbon or heteroatom as appropriate, if not otherwise specified. Thus, for example, when Het is imidazolyl, it may be 1-imidazolyl, 2-imidazolyl, 4-imidazolyl and the like.

Lines drawn from substituents into ring systems indicate that the bond may be attached to any of the suitable ring atoms.

The pharmaceutically acceptable salts as mentioned hereinbefore or hereinafter are meant to comprise the therapeutically active non-toxic acid addition salt forms which the compounds according to formula (Ia) or formula (Ib) are able to form. Said acid addition salts can be obtained by treating the base form of the compounds according to formula (Ia) or formula (Ib) with appropriate acids, for example inorganic acids, for example hydrohalic acid, in particular hydrochloric acid, hydrobromic acid, sulfuric acid, nitric acid and phosphoric acid; organic acids, for example acetic acid, hydroxyacetic acid, propanoic acid, lactic acid, pyruvic acid, oxalic acid, malonic acid, succinic acid, maleic acid, fumaric acid, malic acid, tartaric acid, citric acid, methanesulfonic acid, ethanesulfonic acid, benzenesulfonic acid, p-toluenesulfonic acid, cyclamic acid, salicyclic acid, p-aminosalicylic acid and pamoic acid.

The compounds of formula (Ia) or (Ib) containing acidic protons may be converted into their therapeutically active non-toxic metal or amine addition salt forms by treatment with appropriate organic and inorganic bases. The pharmaceutically acceptable salts as mentioned hereinbefore or hereinafter are meant to also comprise the therapeutically active non-toxic metal or amine addition salt forms (base addition salt forms) which the compounds of formula (Ia) or (Ib) are able to form. Appropriate base addition salt forms comprise, for example, the ammonium salts, the alkali and earth alkaline metal salts, e.g. the lithium, sodium, potassium, magnesium, calcium salts and the like, salts with organic bases, e.g. primary, secondary and tertiary aliphatic and aromatic amines such as methylamine, ethylamine, propylamine, isopropylamine, the four butylamine isomers, dimethylamine, diethylamine, diethanolamine, dipropylamine, diisopropylamine, di-n-butylamine, pyrrolidine, piperidine, morpholine, trimethylamine, triethylamine, tripropylamine, quinuclidine, pyridine, quinoline and isoquinoline, the benzathine, N-methyl-D-glucamine, 2-amino-2-(hydroxymethyl)-1,3-propanediol, hydrabamine salts, and salts with amino acids such as, for example, arginine, lysine and the like.

Conversely, said acid or base addition salt forms can be converted into the free forms by treatment with an appropriate base or acid.

The term pharmaceutically acceptable salt also comprises the quaternary ammonium salts (quaternary amines) which the compounds of formula (Ia) or (Ib) are able to form by reaction between a basic nitrogen of a compound of formula (Ia) or (Ib) and an appropriate quaternizing agent, such as, for example, an optionally substituted C$_{1-6}$alkylhalide, arylC$_{1-6}$alkylhalide, C$_{1-6}$alkylcarbonylhalide, arylcarbonylhalide, HetC$_{1-6}$alkylhalide or Hetcarbonylhalide, e.g. methyliodide or benzyliodide. Preferably, Het represents a monocyclic heterocycle selected from furanyl or thienyl; or a bicyclic heterocycle selected from benzofuranyl or benzothienyl; each monocyclic and bicyclic heterocycle may optionally be substituted with 1, 2 or 3 substituents, each substituent being independently selected from the group of halo, alkyl and aryl. Preferably, the quaternizing agent is a C$_{1-6}$alkylhalide. Other reactants with good leaving groups may also be used, such as C$_{1-6}$alkyl trifluoromethanesulfonates, C$_{1-6}$alkyl methanesulfonates, and C$_{1-6}$alkyl p-toluenesulfonates. A quaternary amine has a positively charged nitrogen. Pharmaceutically acceptable counterions include chloro, bromo, iodo, trifluoroacetate, acetate, triflate, sulfate, sulfonate. Preferably, the counterion is iodo. The counterion of choice can be introduced using ion exchange resins.

Preferably, the term pharmaceutically acceptable salt means the pharmaceutically acceptable acid and base additional salts as mentioned hereinabove.

The term solvate comprises the hydrates and solvent addition forms which the compounds of formula (Ia) or (Ib) are able to form, as well as the salts thereof. Examples of such forms are e.g. hydrates, alcoholates and the like.

In the framework of this application, a compound according to the invention is inherently intended to comprise all stereochemically isomeric forms thereof. The term "stereochemically isomeric forms" as used hereinbefore or hereinafter defines all the possible stereoisomeric forms which the compounds of formula (Ia) and (Ib), and their N-oxides, pharmaceutically acceptable salts, solvates or physiologically functional derivatives may possess. Unless otherwise mentioned or indicated, the chemical designation of compounds denotes the mixture of all possible stereochemically isomeric forms. In particular, stereogenic centers may have the R- or S-configuration; substituents on bivalent cyclic (partially) saturated radicals may have either the cis- or trans-configuration. Compounds encompassing double bonds can have an E (entgegen) or Z (zusammen)-stereochemistry at said double bond. The terms cis, trans, R, S, E and Z are well known to a person skilled in the art. Stereochemically isomeric forms of the compounds of formula (Ia) and (Ib) are obviously intended to be embraced within the scope of this invention. 3. Of special interest are those compounds of formula (Ia) or (Ib) which are stereochemically pure.

Following CAS-nomenclature conventions, when stereogenic centers of known absolute configuration are present in a molecule, an R or S descriptor is assigned (based on Cahn-Ingold-Prelog sequence rule) to the lowest-numbered chiral center, the reference center.

When a specific stereoisomeric form is indicated, this means that said form is substantially free, i.e. associated with less than 50%, preferably less than 20%, more preferably less than 10%, even more preferably less than 5%, further preferably less than 2% and most preferably less than 1% of the other isomer(s). Thus, when a compound of formula (Ia) or (Ib) is for instance specified as a specific enantiomer, this means that the compound is substantially free of the other enantiomers.

Compounds of either formula (Ia) and (Ib) and some of the intermediate compounds have a stereogenic center in their structure which may lead to at least two stereochemically different structures. In the structures below, the stereogenic center is indicated with *.

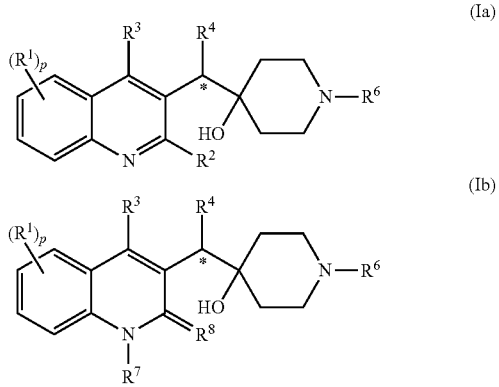

The compounds of either formula (Ia) and (Ib) may be synthesized in the form of mixtures, in particular racemic mixtures, of enantiomers which can be separated from one another following art-known resolution procedures. A manner of separating the enantiomeric forms of the compounds of either formula (Ia) and (Ib) involves liquid chromatography using a chiral stationary phase. Said pure stereochemically isomeric forms may also be derived from the corresponding pure stereochemically isomeric forms of the appropriate starting materials, provided that the reaction occurs stereospecifically. Preferably if a specific stereoisomer is desired, said compound will be synthesized by stereospecific methods of preparation. These methods will advantageously employ enantiomerically pure starting materials.

The tautomeric forms of the compounds of formula (Ia) or (Ib) are meant to comprise those compounds of formula (Ia) or (Ib) wherein e.g. an enol group is converted into a keto group (keto-enol tautomerism). Tautomeric forms of the compounds of formula (Ia) and (Ib) or of intermediates of the present invention are intended to be embraced by the ambit of this invention.

The N-oxide forms of the present compounds are meant to comprise the compounds of formula (Ia) or (Ib) wherein one or several tertiary nitrogen atoms are oxidized to the so-called N-oxide.

The compounds of formula (Ia) and (Ib) may be converted to the corresponding N-oxide forms following art-known procedures for converting a trivalent nitrogen into its N-oxide form. Said N-oxidation reaction may generally be carried out by reacting the starting material of formula (Ia) or (Ib) with an appropriate organic or inorganic peroxide. Appropriate inorganic peroxides comprise, for example, hydrogen peroxide, alkali metal or earth alkaline metal peroxides, e.g. sodium peroxide, potassium peroxide; appropriate organic peroxides may comprise peroxy acids such as, for example, benzenecarboperoxoic acid or halo substituted benzenecarboperoxoic acid, e.g. 3-chlorobenzenecarboperoxoic acid, peroxoalkanoic acids, e.g. peroxoacetic acid, alkylhydroperoxides, e.g. tert-butyl hydroperoxide. Suitable solvents are, for example, water, lower alcohols, e.g. ethanol and the like, hydrocarbons, e.g. toluene, ketones, e.g. 2-butanone, halogenated hydrocarbons, e.g. dichloromethane, and mixtures of such solvents.

In the framework of this application, a compound according to the invention is inherently intended to comprise all isotopic combinations of its chemical elements. In the framework of this application, a chemical element, in particular when mentioned in relation to a compound according to formula (Ia) or (Ib), comprises all isotopes and isotopic mixtures of this element, either naturally occurring or synthetically produced, either with natural abundance or in an isotopically enriched form. In particular, when hydrogen is mentioned, it is understood to refer to $^{1}$H, $^{2}$H, $^{3}$H and mixtures thereof; when carbon is mentioned, it is understood to refer to $^{11}$C, $^{12}$C, $^{13}$C, $^{14}$C and mixtures thereof; when nitrogen is mentioned, it is understood to refer to $^{13}$N, $^{14}$N, $^{15}$N and mixtures thereof; when oxygen is mentioned, it is understood to refer to $^{14}$O, $^{15}$O, $^{16}$O, $^{17}$O, $^{18}$O and mixtures thereof; and when fluor is mentioned, it is understood to refer to $^{18}$F, $^{19}$F and mixtures thereof.

A compound according to the invention therefore inherently comprises a compound with one or more isotopes of one or more element, and mixtures thereof, including a radioactive compound, also called radiolabelled compound, wherein one or more non-radioactive atoms has been replaced by one of its radioactive isotopes. By the term "radiolabelled compound" is meant any compound according to formula (Ia) or (Ib), a pharmaceutically acceptable salt thereof or an N-oxide form thereof or a solvate thereof, which contains at least one radioactive atom. For example, a compound can be labelled with positron or with gamma emitting radioactive isotopes. For radioligand-binding techniques (membrane receptor assay), the $^{3}$H-atom or the $^{125}$I-atom is the atom of choice to be replaced. For imaging, the most commonly used positron emitting (PET) radioactive isotopes are $^{11}$C, $^{18}$F, $^{15}$O and $^{13}$N, N all of which are accelerator produced and have half-lives of 20, 100, 2 and 10 minutes respectively. Since the half-lives of these radioactive isotopes are so short, it is only feasible to use them at institutions which have an accelerator on site for their production, thus limiting their use. The most widely used of these are $^{18}$F, $^{99m}$Tc, $^{201}$Tl and $^{123}$I. The handling of these radioactive isotopes, their production, isolation and incorporation in a molecule are known to the skilled person.

In particular, the radioactive atom is selected from the group of hydrogen, carbon, nitrogen, sulfur, oxygen and halogen. Preferably, the radioactive atom is selected from the group of hydrogen, carbon and halogen.

In particular, the radioactive isotope is selected from the group of $^{3}$H, $^{11}$C, $^{18}$F, $^{122}$I, $^{123}$I, $^{125}$I, $^{131}$I, $^{75}$Br, $^{76}$Br, $^{77}$Br and $^{82}$Br. Preferably, the radioactive isotope is selected from the group of $^{3}$H, $^{11}$C and $^{18}$F.

In the framework of this application, $C_{1-6}$alkyl represents a straight or branched saturated hydrocarbon radical having from 1 to 6 carbon atoms such as for example methyl, ethyl, propyl, 2-methyl-ethyl, pentyl, hexyl and the like. A preferred subgroup of $C_{1-6}$alkyl is $C_{1-4}$alkyl which represents a straight or branched saturated hydrocarbon radical having from 1 to 4 carbon atoms such as for example methyl, ethyl, propyl, 2-methyl-ethyl and the like.

In the framework of this application $C_{2-6}$alkenyl is a straight or branched hydrocarbon radical having from 2 to 6 carbon atoms containing a double bond such as ethenyl, propenyl, butenyl, pentenyl, hexenyl and the like; $C_{2-6}$alkynyl is a straight or branched hydrocarbon radical having from 2 to 6 carbon atoms containing a triple bond such as ethynyl, propynyl, butynyl, pentynyl, hexynyl and the like; $C_{3-6}$cycloalkyl is a cyclic saturated hydrocarbon radical having from 3 to 6 carbon atoms and is generic to cyclo-propyl, cyclobutyl, cyclopentyl and cyclohexyl.

In the framework of this application, halo is a substituent selected from the group of fluoro, chloro, bromo and iodo. Preferably, halo is bromo, fluoro or chloro; in particular chloro or bromo.

In the framework of this application, polyhalo$C_{1-6}$alkyl is defined as mono- or polyhalosubstituted $C_{1-6}$alkyl, for example, methyl with one or more fluoro atoms, for example, difluoromethyl or trifluoromethyl, 1,1-difluoro-ethyl and the like. In case more than one halo atom is attached to a $C_{1-6}$alkyl group within the definition of polyhalo$C_{1-6}$alkyl, they may be the same or different.

An interesting embodiment relates to a compound of formula (Ia) or (Ib), wherein $R^{1}$ is hydrogen, cyano, carboxyl, halo, $C_{1-6}$alkyl, $C_{2-6}$alkenyl, polyhalo$C_{1-6}$alkyl, hydroxyl, hydroxy$C_{1-6}$alkyl, $C_{1-6}$alkyloxy, $C_{1-6}$alkylthio, amino, mono or di($C_{1-6}$alkyl)amino, amino$C_{1-6}$alkyl, mono or di($C_{1-6}$alkyl)amino$C_{1-6}$alkyl, $R^{9b}R^{10b}N$—C(=O)—, aryl, $R^{9a}R^{10a}N$—, $R^{9a}R^{10a}N$—C(=O)—, $C_{1-4}$alkyl-S(=O)$_{2}$—, or Het; in particular $R^{1}$ is hydrogen, cyano, carboxyl, halo, $C_{1-6}$alkyl, $C_{2-6}$alkenyl, polyhalo$C_{1-6}$alkyl, hydroxy$C_{1-6}$alkyl, $C_{1-6}$alkyloxy, $C_{1-6}$alkylthio, amino$C_{1-6}$alkyl, $R^{9b}R^{10b}N$—C(=O)—, aryl, $C_{1-4}$alkyl-S(=O)$_{2}$—, or Het; more in particular $R^{1}$ is halo especially bromo, $C_{1-4}$alkyl-S(=O)$_{2}$— especially $CH_{3}$—(S=O)$_{2}$—, or Het especially pyridinyl.

A second interesting embodiment relates to a compound of formula (Ia) or (Ib), or a subgroup thereof as mentioned hereinbefore as an interesting embodiment, wherein p is 1 or 2; in particular p is 1.

A third interesting embodiment relates to a compound of formula (Ia), or any subgroup thereof as mentioned hereinbefore as an interesting embodiment, wherein $R^{2}$ is hydrogen, $C_{1-6}$alkyloxy, $C_{1-6}$alkylthio, mono or di($C_{1-6}$alkyl)amino, amino or a radical of formula

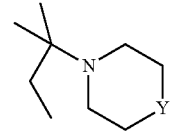

wherein Y is $CH_{2}$, O, S, NH or N—$C_{1-6}$alkyl; in particular $R^{2}$ is $C_{1-6}$alkyloxy, $C_{1-6}$alkylthio, mono or di($C_{1-6}$alkyl)amino, or a radical of formula

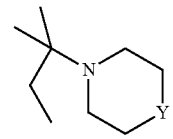

wherein Y is $CH_{2}$ or O; more in particular $R^{2}$ is $C_{1-6}$alkyloxy or $C_{1-6}$alkylthio; even more in particular $R^{2}$ is $C_{1-6}$alkyloxy especially methyloxy, or a radical of formula

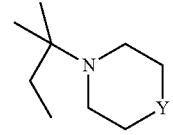

wherein Y is O.

A fourth interesting embodiment relates to a compound of formula (Ia) or (Ib), or any subgroup thereof as mentioned hereinbefore as an interesting embodiment, wherein $R^{3}$ is hydrogen, halo or $C_{1-6}$alkyl; in particular $R^{3}$ is hydrogen.

A fifth interesting embodiment relates to a compound of formula (Ia) or (Ib), or any subgroup thereof as mentioned hereinbefore as an interesting embodiment, wherein $R^{4}$ is aryl$^{1}$; in particular $R^{4}$ is phenyl or naphthyl, each being optionally substituted with 1, 2 or 3 substituents, each substituent being independently selected from halo, cyano, $C_{1-6}$alkyl, polyhalo$C_{1-6}$alkyl, $C_{1-6}$alkyloxy, $C_{1-6}$alkylthio, $C_{1-4}$alkyl-S(=O)$_2$—; more in particular $R^4$ is phenyl or naphthyl optionally substituted with 1, 2 or 3 substituents, each substituent being independently selected from halo, cyano, $C_{1-6}$alkyl, polyhalo$C_{1-6}$alkyl, $C_{1-6}$alkyloxy, $C_{1-6}$alkylthio or $C_{1-4}$alkyl-S(=O)$_2$—; even more in particular $R^4$ is phenyl or naphthyl optionally substituted with 1 substituent, said substituent being selected from halo especially chloro, cyano or $C_{1-4}$alkyl-S(=O)$_2$ especially $CH_3$—(S=O)$_2$—.

A sixth interesting embodiment relates to a compound of formula (Ia) or (Ib), or any subgroup thereof as mentioned hereinbefore as an interesting embodiment, wherein $R^4$ is Het; in particular $R^4$ is a monocyclic heterocycle selected from N-phenoxypiperidinyl, piperidinyl, piperazinyl, pyrrolyl, pyrazolyl, imidazolyl, furanyl, thienyl, oxazolyl, isoxazolyl, thiazolyl, isothiazolyl, pyridinyl, pyrimidinyl, pyrazinyl or pyridazinyl; each monocyclic heterocycle being optionally substituted with 1, 2 or 3 substituents, each substituent being independently selected from halo, hydroxy, $C_{1-6}$alkyl or $C_{1-6}$alkyloxy; more in particular $R^4$ is a monocyclic heterocycle selected from piperidinyl, pyrazolyl, furanyl or pyridinyl, especially pyrazolyl or pyridinyl; each monocyclic heterocycle being optionally substituted with 1 substituent selected from halo, hydroxy, $C_{1-6}$alkyl or $C_{1-6}$alkyloxy, in particular hydroxy.

A seventh interesting embodiment relates to a compound of formula (Ia) or (Ib), or any subgroup thereof as mentioned hereinbefore as an interesting embodiment, wherein $R^6$ is hydrogen, $C_{1-6}$alkyl, aryl$C_{1-6}$alkyl, Het, or —C(=NH)—NH$_2$; in particular $R^6$ is hydrogen, $C_{1-6}$alkyl, aryl$C_{1-6}$alkyl or —C(=NH)—NH$_2$; more in particular $R^6$ is hydrogen, $C_{1-6}$alkyl, phenyl$C_{1-6}$alkyl or —C(=NH)—NH$_2$; even further in particular $R^6$ is hydrogen, $C_{1-6}$alkyl, benzyl or phenylethyl.

An eighth interesting embodiment relates to a compound of formula (Ib), or any subgroup thereof as mentioned hereinbefore as an interesting embodiment, wherein $R^7$ is hydrogen or $C_{1-6}$alkyl especially ethyl, and $R^8$ is oxo; in particular $R^7$ is hydrogen and $R^8$ is oxo.

A ninth interesting embodiment relates to a compound of formula (Ia) or (Ib), or any subgroup thereof as mentioned hereinbefore as an interesting embodiment, wherein the compound is a compound of formula (Ia).

A tenth interesting embodiment relates to a compound of formula (Ia) or (Ib), or any subgroup thereof as mentioned hereinbefore as an interesting embodiment, wherein the compound is a compound of formula (Ib).

A eleventh interesting embodiment relates to a compound of formula (Ia) or (Ib), or any subgroup thereof as mentioned hereinbefore as an interesting embodiment wherein $R^1$ is placed in position 6 of the quinoline ring.

In the framework of this application, the quinoline ring of the compounds of formula (Ia) or (Ib) is numbered as follows:

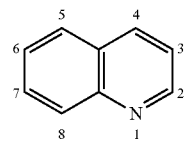

A twelfth interesting embodiment relates to a compound of formula (Ia) or (Ib), or any subgroup thereof as mentioned hereinbefore as an interesting embodiment, wherein aryl is naphthyl or phenyl, more preferably phenyl, each being optionally substituted with one or two substituents each being independently selected from halo, for example chloro; cyano; alkyl for example methyl; or alkyloxy for example methyloxy.

A thirteenth interesting embodiment relates to a compound of formula (Ia) or (Ib), or any subgroup thereof as mentioned hereinbefore as interesting embodiment, wherein aryl$^1$ is naphthyl or phenyl, more preferably phenyl, each optionally substituted with one or two substituents selected from halo, for example chloro; cyano; $C_{1-6}$alkyl for example methyl; alkyloxy, for example methyloxy; $C_{1-6}$alkylthio for example methylthio; or $C_{1-4}$alkyl-S(=O)$_2$— for example methyl-S(=O)$_2$—.

A fourteenth interesting embodiment relates to a compound of formula (Ia) or (Ib), or any subgroup thereof as mentioned hereinbefore as an interesting embodiment, wherein Het is piperdinyl, furanyl, pyridinyl, benzofuranyl or benzo[1,3]dioxolyl.

A fifteenth interesting embodiment relates to a compound of formula (Ia) or any subgroup thereof as mentioned hereinbefore as interesting embodiment, wherein one or more, preferably all, of the following definitions apply:

p is 1;

$R^1$ is halo, in particular bromo, chloro or fluoro; $C_{1-6}$alkylthio, in particular methylthio;

$C_{1-4}$alkyl-S(=O)$_2$—, in particular methyl-S(=O)$_2$—; or Het, in particular pyridinyl;

$R^2$ is $C_{1-6}$alkyloxy, in particular methyloxy, or Het in particular morpholinyl;

$R^3$ is hydrogen;

$R^4$ is phenyl optionally substituted with halo, in particular chloro, cyano or $C_{1-4}$alkyl-S(=O)$_2$—, in particular methyl-S(=O)$_2$—, in either the 3- or 4-position; and $R^6$ is hydrogen, $C_{1-6}$alkyl in particular methyl, phenyl$C_{1-6}$alkyl in particular benzyl or phenylethyl, or —C(=NH)—NH$_2$.

A sixteenth interesting embodiment relates to a compound of formula (Ib) or any subgroup thereof as mentioned hereinbefore as interesting embodiment wherein one or more, preferably all, of the following definitions apply:

p is 1;

$R^1$ is halo, in particular bromo, chloro or fluoro; $C_{1-6}$alkylthio, in particular methylthio;

$C_{1-4}$alkyl-S(=O)$_2$—, in particular methyl-S(=O)$_2$—; or Het, in particular pyridinyl;

$R^3$ is hydrogen;

$R^4$ is phenyl optionally substituted with halo, in particular chloro, cyano or $C_{1-4}$alkyl-S(=O)$_2$—, in particular methyl-S(=O)$_2$—, in either the 3- or 4-position;

$R^6$ is hydrogen, $C_{1-6}$alkyl in particular methyl, phenyl$C_{1-6}$alkyl in particular benzyl or phenylethyl, or —C(=NH)—NH$_2$;

$R^7$ is hydrogen or $C_{1-6}$alkyl especially ethyl; and $R^8$ is oxo.

Preferred compounds according to the present invention are selected from the following compounds:

Comp. No. 25
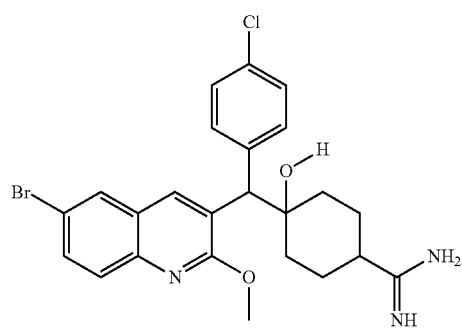
Comp. No. 1
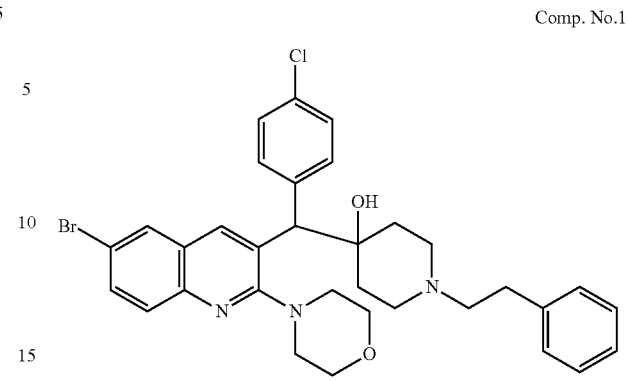
Comp. No. 10
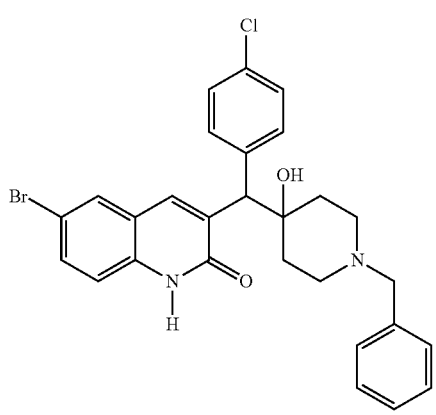
Comp. No. 3
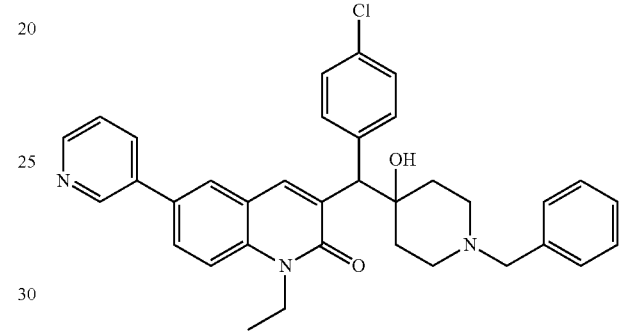
Comp. No. 80
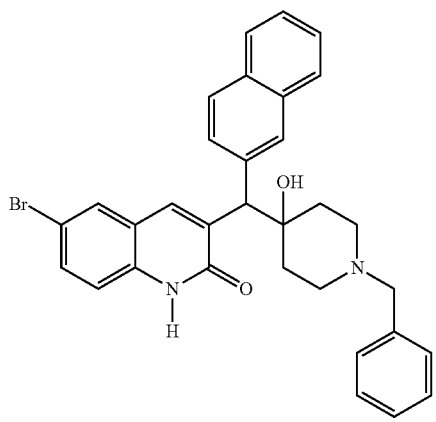
Comp. No. 20
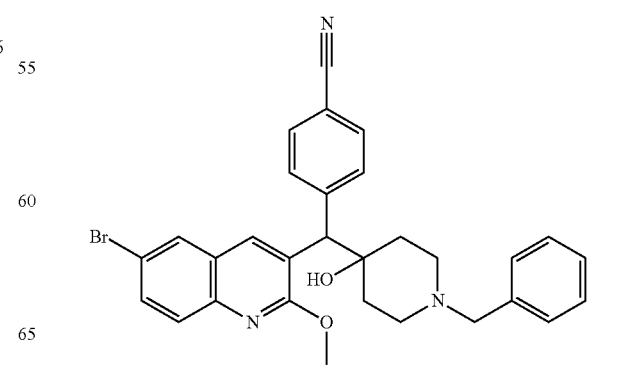
Comp. No. 16
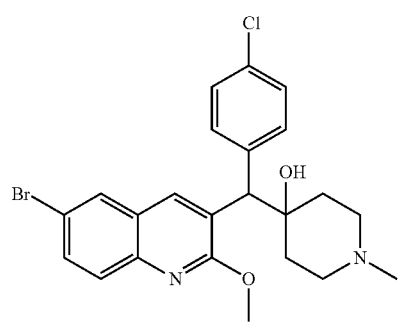
Comp. No. 58

Comp. No.100

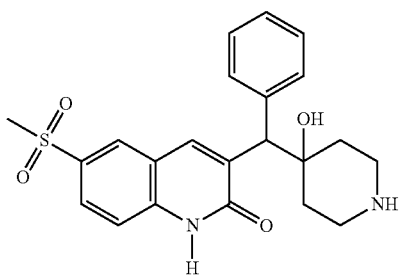

Comp. No.27

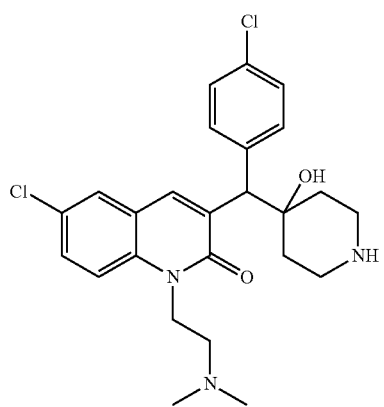

including any stereochemically isomeric form thereof; a N-oxide thereof, a pharmaceutically acceptable salt thereof or a solvate thereof.

PHARMACOLOGY

The compounds according to the invention have surprisingly been shown to be suitable for the treatment of a bacterial infection including a mycobacterial infection, particularly those diseases caused by pathogenic mycobacteria such as *Mycobacterium tuberculosis* (including the latent and drug resistant form thereof), *M. bovis, M. avium, M. leprae* and *M. marinum*. The present invention thus also relates to compounds of formula (Ia) or (Ib) as defined hereinabove and their stereochemically isomeric forms, the pharmaceutically acceptable salts thereof or the N-oxide forms thereof or the solvates thereof, for use as a medicine, in particular for use as a medicine for the treatment of a bacterial infection including a mycobacterial infection.

Further, the present invention also relates to the use of a compound of formula (Ia) or (Ib) and their stereochemically isomeric forms, the pharmaceutically acceptable salts thereof or the N-oxide forms thereof or the solvates thereof, as well as any of the pharmaceutical compositions thereof as described hereinafter for the manufacture of a medicament for the treatment of a bacterial infection including a mycobacterial infection.

Accordingly, in another aspect, the invention provides a method of treating a patient suffering from, or at risk of, a bacterial infection, including a mycobacterial infection, which comprises administering to the patient a therapeutically effective amount of a compound or pharmaceutical composition according to the invention.

In addition to their activity against mycobacteria, the compounds according to the invention are also active against other bacteria. In general, bacterial pathogens may be classified as either gram-positive or gram-negative pathogens. Antibiotic compounds with activity against both gram-positive and gram-negative pathogens are generally regarded as having a broad spectrum of activity. The compounds of the present invention are regarded as active against gram-positive and/or gram-negative bacterial pathogens, in particular against gram-positive bacterial pathogens. In particular, the present compounds are active against at least one gram-positive bacterium, preferably against several gram-positive bacteria, more preferably against one or more gram-positive bacteria and/or one or more gram-negative bacteria.

The present compounds have bactericidal or bacteriostatic activity.

Examples of gram-positive and gram-negative aerobic and anaerobic bacteria, include Staphylococci, for example *S. aureus*; Enterococci, for example *E. faecalis*; Streptococci, for example *S. pneumoniae, S. mutans, S. pyogens*; Bacilli, for example *Bacillus subtilis; Listeria*, for example *Listeria monocytogenes; Haemophilus*, for example *H. influenza; Moraxella*, for example *M. catarrhalis; Pseudomonas*, for example *Pseudomonas aeruginosa*; and *Escherichia*, for example *E. coli*.

Gram-positive pathogens, for example Staphylococci, Enterococci and Streptococci are particularly important because of the development of resistant strains which are both difficult to treat and difficult to eradicate from for example a hospital environment once established. Examples of such strains are methicillin resistant *Staphylococcus aureus* (MRSA), methicillin resistant coagulase negative staphylococci (MRCNS), penicillin resistant *Streptococcus pneumoniae* and multiple resistant *Enterococcus faecium*.

The compounds of the present invention also show activity against resistant bacterial strains.

The compounds of the present invention are especially active against *Staphylococcus aureus*, including resistant *Staphylococcus aureus* such as for example methicillin resistant *Staphylococcus aureus* (MRSA).

Therefore, the present invention also relates to the use of a compound of formula (Ia) or (Ib) and their stereochemically isomeric forms, the pharmaceutically acceptable salts thereof or the N-oxide forms thereof or the solvates thereof, as well as any of the pharmaceutical compositions thereof as described hereinafter for the manufacture of a medicament for the treatment of a bacterial infection including an infection caused by Staphylococci.

Accordingly, in another aspect, the invention provides a method of treating a patient suffering from, or at risk of, a bacterial infection, including an infection caused by Staphylococci, which comprises administering to the patient a therapeutically effective amount of a compound or pharmaceutical composition according to the invention.

Without being bound to any theory, it is taught that the activity of the present compounds lies in inhibition of the F1F0 ATP synthase, in particular the inhibition of the F0 complex of the F1F0 ATP synthase, more in particular the inhibition of subunit c of the F0 complex of the F1F0 ATP synthase, leading to killing of the bacteria by depletion of the cellular ATP levels of the bacteria. Therefore, in particular, the compounds of the present invention are active on those bacteria of which the viability depends on proper functioning of F1F0 ATP synthase.

Bacterial infections which may be treated by the present compounds include, for example, central nervous system infections, external ear infections, infections of the middle ear, such as acute otitis media, infections of the cranial sinuses, eye infections, infections of the oral cavity, such as infections of the teeth, gums and mucosa, upper respiratory tract infections, lower respiratory tract infections, genitourinary infections, gastrointestinal infections, gynaecological infections, septicemia, bone and joint infections, skin and skin structure infections, bacterial endocarditis, burns, antibacterial prophylaxis of surgery, and antibacterial prophylaxis in immunosuppressed patients, such as patients receiving cancer chemotherapy, or organ transplant patients.

Whenever used hereinbefore or hereinafter, that the compounds can treat a bacterial infection it is meant that the compounds can treat an infection with one or more bacterial strains.

The invention also relates to a composition comprising a pharmaceutically acceptable carrier and, as active ingredient, a therapeutically effective amount of a compound according to the invention. The compounds according to the invention may be formulated into various pharmaceutical forms for administration purposes. As appropriate compositions there may be cited all compositions usually employed for systemically administering drugs. To prepare the pharmaceutical compositions of this invention, an effective amount of the particular compound, optionally in addition salt form, as the active ingredient is combined in intimate admixture with a pharmaceutically acceptable carrier, which carrier may take a wide variety of forms depending on the form of preparation desired for administration. These pharmaceutical compositions are desirable in unitary dosage form suitable, in particular, for administration orally or by parenteral injection. For example, in preparing the compositions in oral dosage form, any of the usual pharmaceutical media may be employed such as, for example, water, glycols, oils, alcohols and the like in the case of oral liquid preparations such as suspensions, syrups, elixirs, emulsions and solutions; or solid carriers such as starches, sugars, kaolin, diluents, lubricants, binders, disintegrating agents and the like in the case of powders, pills, capsules and tablets. Because of their ease in administration, tablets and capsules represent the most advantageous oral dosage unit forms in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. Also included are solid form preparations which are intended to be converted, shortly before use, to liquid form preparations.

Depending on the mode of administration, the pharmaceutical composition will preferably comprise from 0.05 to 99% by weight, more preferably from 0.1 to 70% by weight, even more preferably from 0.1 to 50% by weight of the active ingredient(s), and, from 1 to 99.95% by weight, more preferably from 30 to 99.9% by weight, even more preferably from 50 to 99.9% by weight of a pharmaceutically acceptable carrier, all percentages being based on the total weight of the composition.

The pharmaceutical composition may additionally contain various other ingredients known in the art, for example, a lubricant, stabilising agent, buffering agent, emulsifying agent, viscosity-regulating agent, surfactant, preservative, flavouring or colorant.

It is especially advantageous to formulate the aforementioned pharmaceutical compositions in unit dosage form for ease of administration and uniformity of dosage. Unit dosage form as used herein refers to physically discrete units suitable as unitary dosages, each unit containing a predetermined quantity of active ingredient calculated to produce the desired therapeutic effect in association with the required pharmaceutical carrier. Examples of such unit dosage forms are tablets (including scored or coated tablets), capsules, pills, powder packets, wafers, suppositories, injectable solutions or suspensions and the like, and segregated multiples thereof. The daily dosage of the compound according to the invention will, of course, vary with the compound employed, the mode of administration, the treatment desired and the mycobacterial disease indicated. However, in general, satisfactory results will be obtained when the compound according to the invention is administered at a daily dosage not exceeding 1 gram, e.g. in the range from 10 to 50 mg/kg body weight.

Given the fact that the compounds of formula (Ia) or Formula (Ib) are active against bacterial infections, the present compounds may be combined with other antibacterial agents in order to effectively combat bacterial infections.

Therefore, the present invention also relates to a combination of (a) a compound according to the invention, and (b) one or more other antibacterial agents.

The present invention also relates to a combination of (a) a compound according to the invention, and (b) one or more other antibacterial agents, for use as a medicine.

The present invention also relates to the use of a combination or pharmaceutical composition as defined directly above for the treatment of a bacterial infection.

A pharmaceutical composition comprising a pharmaceutically acceptable carrier and, as active ingredient, a therapeutically effective amount of (a) a compound according to the invention, and (b) one or more other antibacterial agents, is also comprised by the present invention.

The weight ratio of (a) the compound according to the invention and (b) the other antibacterial agent(s) when given as a combination may be determined by the person skilled in the art. Said ratio and the exact dosage and frequency of administration depends on the particular compound according to the invention and the other antibacterial agent(s) used, the particular condition being treated, the severity of the condition being treated, the age, weight, gender, diet, time of administration and general physical condition of the particular patient, the mode of administration as well as other medication the individual may be taking, as is well known to those skilled in the art. Furthermore, it is evident that the effective daily amount may be lowered or increased depending on the response of the treated subject and/or depending on the evaluation of the physician prescribing the compounds of the instant invention. A particular weight ratio for the present compound of formula (Ia) or (Ib) and another antibacterial agent may range from 1/10 to 10/1, more in particular from 1/5 to 5/1, even more in particular from 1/3 to 3/1.

The compounds according to the invention and the one or more other antibacterial agents may be combined in a single preparation or they may be formulated in separate preparations so that they can be administered simultaneously, separately or sequentially. Thus, the present invention also relates to a product containing (a) a compound according to the invention, and (b) one or more other antibacterial agents, as a combined preparation for simultaneous, separate or sequential use in the treatment of a bacterial infection.

The other antibacterial agents which may be combined with the compounds of formula (Ia) or (Ib) are for example antibacterial agents known in the art. The other antibacterial agents comprise antibiotics of the β-lactam group such as natural penicillins, semisynthetic penicillins, natural cephalosporins, semisynthetic cephalosporins, cephamycins, 1-oxacephems, clavulanic acids, penems, carbapenems, nocardicins, monobactams; tetracyclines, anhydrotetracyclines, anthracyclines; aminoglycosides; nucleosides such as N-nucleosides, C-nucleosides, carbocyclic nucleosides, blasticidin S; macrolides such as 12-membered ring macrolides, 14-membered ring macrolides, 16-membered ring macrolides; ansamycins; peptides such as bleomycins, gramicidins, polymyxins, bacitracins, large ring peptide antibiotics containing lactone linkages, actinomycins, amphomycin, capreomycin, distamycin, enduracidins, mikamycin, neocarzinostatin, stendomycin, viomycin, virginiamycin; cycloheximide; cycloserine; variotin; sarkomycin A; novobiocin; griseofulvin; chloramphenicol; mitomycins; fumagillin; monensins; pyrrolnitrin; fosfomycin; fusidic acid; D-(p-hydroxyphenyl)glycine; D-phenylglycine; enediynes.

Specific antibiotics which may be combined with the present compounds of formula (Ia) or (Ib) are for example benzylpenicillin (potassium, procaine, benzathine), phenoxymethylpenicillin (potassium), phenethicillin potassium, propicillin, carbenicillin (disodium, phenyl sodium, indanyl sodium), sulbenicillin, ticarcillin disodium, methicillin sodium, oxacillin sodium, cloxacillin sodium, dicloxacillin, flucloxacillin, ampicillin, mezlocillin, piperacillin sodium, amoxicillin, ciclacillin, hectacillin, sulbactam sodium, talampicillin hydrochloride, bacampicillin hydrochloride, pivmecillinam, cephalexin, cefaclor, cephaloglycin, cefadroxil, cephradine, cefroxadine, cephapirin sodium, cephalothin sodium, cephacetrile sodium, cefsulodin sodium, cephaloridine, cefatrizine, cefoperazone sodium, cefamandole, vefotiam hydrochloride, cefazolin sodium, ceftizoxime sodium, cefotaxime sodium, cefmenoxime hydrochloride, cefuroxime, ceftriaxone sodium, ceftazidime, cefoxitin, cefmetazole, cefotetan, latamoxef, clavulanic acid, imipenem, aztreonam, tetracycline, chlortetracycline hydrochloride, demethylchlortetracycline, oxytetracycline, methacycline, doxycycline, rolitetracycline, minocycline, daunorubicin hydrochloride, doxorubicin, aclarubicin, kanamycin sulfate, bekanamycin, tobramycin, gentamycin sulfate, dibekacin, amikacin, micronomicin, ribostamycin, neomycin sulfate, paromomycin sulfate, streptomycin sulfate, dihydrostreptomycin, destomycin A, hygromycin B, apramycin, sisomicin, netilmicin sulfate, spectinomycin hydrochloride, astromicin sulfate, validamycin, kasugamycin, polyoxin, blasticidin S, erythromycin, erythromycin estolate, oleandomycin phosphate, tracetyloleandomycin, kitasamycin, josamycin, spiramycin, tylosin, ivermectin, midecamycin, bleomycin sulfate, peplomycin sulfate, gramicidin S, polymyxin B, bacitracin, colistin sulfate, colistinmethanesulfonate sodium, enramycin, mikamycin, virginiamycin, capreomycin sulfate, viomycin, enviomycin, vancomycin, actinomycin D, neocarzinostatin, bestatin, pepstatin, monensin, lasalocid, salinomycin, amphotericin B, nystatin, natamycin, trichomycin, mithramycin, lincomycin, clindamycin, clindamycin palmitate hydrochloride, flavophospholipol, cycloserine, pecilocin, griseofulvin, chloramphenicol, chloramphenicol palmitate, mitomycin C, pyrrolnitrin, fosfomycin, fusidic acid, bicozamycin, tiamulin, siccanin.

Other antimycobacterial agents which may be combined with the compounds of formula (Ia) or (Ib) are for example rifampicin (=rifampin); isoniazid; pyrazinamide; amikacin; ethionamide; ethambutol; streptomycin; para-aminosalicylic acid; cycloserine; capreomycin; kanamycin; thioacetazone; PA-824; quinolones/fluoroquinolones such as for example moxifloxacin, gatifloxacin, ofloxacin, ciprofloxacin, sparfloxacin; macrolides such as for example clarithromycin, clofazimine, amoxycillin with clavulanic acid; rifamycins; rifabutin; rifapentine; the compounds disclosed in WO2004/011436.

General Preparation

The compounds according to the invention can generally be prepared by a succession of steps, each of which is known to the skilled person.

Compounds of formula (Ia) wherein $R^6$ is hydrogen, said compounds being represented by formula (Ia-1), can be prepared by deprotecting an intermediate of formula (II-a) wherein $P^1$ is a suitable protecting group such as a $C_{1-6}$alkyloxycarbonyl group especially a tert-butyloxycarbonyl group, for example with a suitable acid such as trifluoroacetic acid or hydrochloric acid in a suitable solvent such as dichloromethane or iso-propanol; alternatively $P^1$ may represent an aryl$C_{1-6}$alkyloxycarbonyl group such as benzyloxycarbonyl and deprotection may be effected by treatment with boron tribromide in a suitable solvent such as dichloromethane.

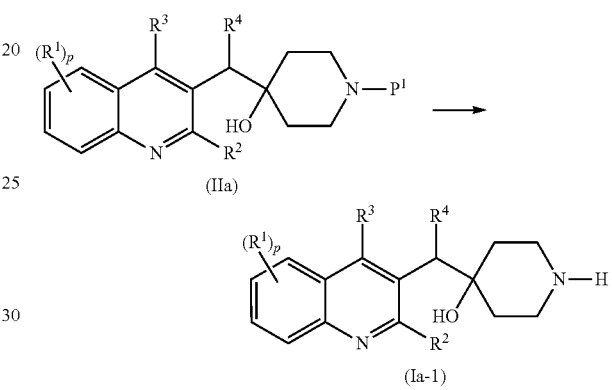

Compounds of formula (Ib) wherein $R^6$ is hydrogen, $R^7$ is hydrogen and $R^8$ is oxo, said compounds being represented by formula (Ib-2), can be prepared by deprotecting an intermediate of formula (IIa) with a suitable acid for example hydrochloric acid or trifluoroacetic acid in a suitable solvent such as tetrahydrofuran or iso-propanol.

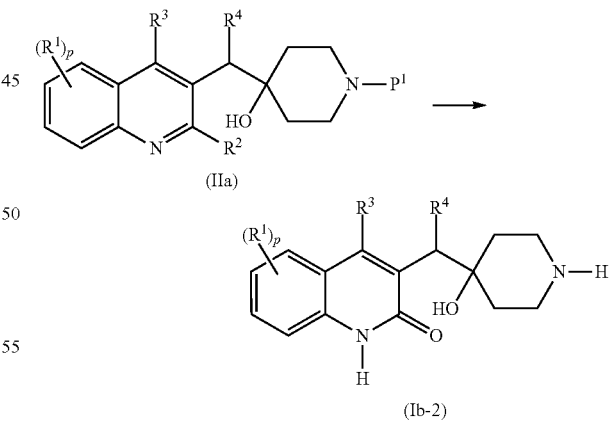

Compounds of formula (Ia) can be prepared by reacting an intermediate of formula (Va) with a compound of formula (VIa) for example in the presence of n-butyl-lithium in hexane in a solvent system comprising for example diisopropylamine in tetrahydrofuran. Alternatively, the reaction can be effected for example in the presence of n-butyl-lithium in a solution of N-(1-methylethyl)-2-propanamine in tetrahydrofuran. Both reactions are preferably effected at a low temperature for example about −70° to −78° C. A further alternative comprises effecting the reaction in the presence of lithium diisopropylamide in a solvent system comprising for example tetrahydrofuran, heptane and ethylbenzene. The reaction may also be effected using sodium cyanoborohydride in an acidic medium such acetic acid and in a suitable solvent such as methanol.

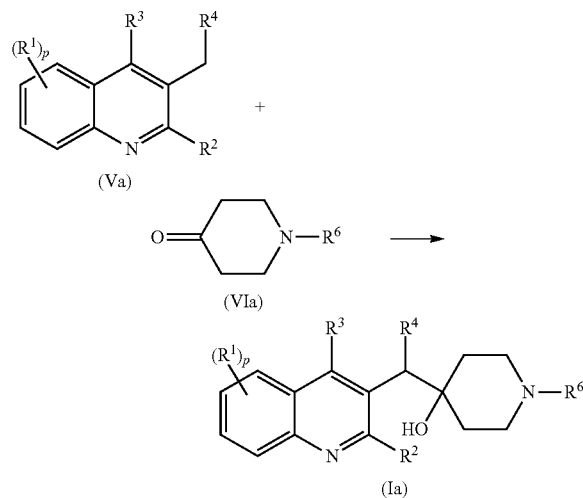

It is considered within the knowledge of the skilled man to explore the appropriate temperatures, dilutions, and reaction times in order to optimize the above reactions in order to obtain a desired compound.

The compounds of formula (Ia) or (Ib) may further be prepared by converting compounds of formula (Ia) or (Ib) into each other according to art-known group transformation reactions.

The compounds of formula (Ia) or (Ib) may be converted to the corresponding N-oxide forms following art-known procedures for converting a trivalent nitrogen into its N-oxide form. Said N-oxidation reaction may generally be carried out by reacting the starting material of formula (Ia) or (Ib) with an appropriate organic or inorganic peroxide. Appropriate inorganic peroxides comprise, for example, hydrogen peroxide, alkali metal or earth alkaline metal peroxides, e.g. sodium peroxide, potassium peroxide; appropriate organic peroxides may comprise peroxy acids such as, for example, benzenecarboperoxoic acid or halo substituted benzenecarboperoxoic acid, e.g. 3-chlorobenzenecarboperoxoic acid, peroxoalkanoic acids, e.g. peroxoacetic acid, alkylhydroperoxides, e.g. tert.butyl hydro-peroxide. Suitable solvents are, for example, water, lower alcohols, e.g. ethanol and the like, hydrocarbons, e.g. toluene, ketones, e.g. 2-butanone, halogenated hydrocarbons, e.g. dichloromethane, and mixtures of such solvents.

Compounds of formula (Ia) or (Ib) wherein $R^1$ represents halo, e.g. bromo, can be converted into a compound of formula (Ia) or (Ib) wherein $R^1$ represents aryl or Het, by reaction with aryl-B(OH)$_2$ or Het-B(OH)$_2$, or a derivative thereof in the presence of a suitable catalyst, such as for example Pd(OAc)$_2$ or Pd(PPh$_3$)$_4$, in the presence of a suitable base, such as for example K$_3$PO$_4$, K$_2$CO$_3$ or Na$_2$CO$_3$, and a suitable solvent, such as for example toluene or 1,2-dimethoxyethane (DME).

Similarly, compounds of formula (Ia) or (Ib) in which $R^1$ is halo, for example bromo, may be converted into compounds of formula (Ia) or (Ib) in which $R^1$ is alkyl, for example methyl, by treatment with an appropriate alkylating agent such as CH$_3$B(OH)$_2$ or (CH$_3$)$_4$Sn in the presence of a suitable catalyst, such as for example Pd(PPh$_3$)$_4$, in a suitable solvent such as for example toluene or 1,2-dimethoxyethane (DME).

Compounds of formula (Ia) or (Ib) wherein $R^1$ is halo, in particular bromo, or aryl C$_{1-6}$ alkyl, can be converted into a compound of formula (Ia) or (Ib) wherein $R^1$ is hydrogen, by reaction with HCOONH$_4$ in the presence of a suitable catalyst such as for example palladium/carbon, and in the presence of a suitable solvent, such as for example an alcohol, e.g. methanol. Alternatively, such conversion can be effected for example using n-butyl-lithium in a suitable solvent such as diethyl ether.

Compounds of formula (Ia) or (Ib) wherein $R^1$ is halo in particular bromo or chloro and $R^6$ is other than hydrogen for example an arylC$_{1-6}$alkyl group such as 1-ethylphenyl, can be converted into a compound of formula (Ia) or (Ib) wherein $R^1$ is hydrogen and $R^6$ is hydrogen by hydrogenation with palladium/carbon in the presence of acetic acid in a suitable solvent such as methanol.

Compounds of formula (Ia) or (Ib) wherein $R^1$ is halo, in particular bromo, can also be converted into a compound wherein $R^1$ is formyl, by reaction with N,N-dimethylformamide in the presence of n-butyl-lithium and a suitable solvent, such as for example tetrahydrofuran. These compounds can then further be converted into a compound of formula (Ia) or (Ib) wherein $R^1$ is —CH$_2$—OH by reaction with a suitable reducing agent, such as for example NaBH$_4$, and in the presence of a suitable solvent, such as for example an alcohol, e.g. methanol, and tetrahydrofuran.

Compounds of formula (Ia) or (Ib) wherein $R^1$ is halo, in particular bromo, can also be converted into a compound wherein $R^1$ is carboxyl by treatment with for example carbon dioxide in the presence of n-butyl-lithium in hexane.

Compounds of formula (Ia) or (Ib) wherein $R^1$ is carboxyl can be converted into compounds of formula (Ia) or (Ib) wherein $R^1$ is Het-NH—CO— by treatment with an appropriate Het-NH$_2$ compound in the presence for example of 1-hydroxybenzotriazole and N'-(ethylcarbonimidoyl)-N,N-dimethyl-1,3-propanediamine in a suitable solvent such as dichloromethane.

Compounds of formula (Ia) or (Ib) wherein $R^1$ is C$_{2-6}$alkenyl, can be prepared by reacting a compound of formula (Ia) or (Ib) wherein $R^1$ is halo, e.g. bromo and the like, with tributyl(C$_{2-6}$alkenyl)tin, such as for example tributyl(vinyl)tin, in the presence of a suitable catalyst, such as for example Pd(PPh$_3$)$_4$, in the presence of a suitable solvent, such as for example N,N-dimethylformamide. This reaction is preferably performed at elevated temperature.

Compounds of formula (Ia) or (Ib) wherein $R^1$ is $R^{9a}R^{10a}$N—, can be prepared from a compound of formula (Ia) or (Ib) wherein $R^1$ is halo, e.g. bromo and the like, by reaction with $R^{9a}R^{10a}$NH or a functional derivative thereof in the presence of a suitable catalyst, such as for example tris (dibenzylideneacetone)palladium, a suitable ligand, such as for example 2-(di-t-butylphosphino)biphenyl, a suitable base, such as for example sodium t-butoxide, and a suitable solvent, such as for example toluene. For example, when $R^1$ represents pyridinyl the initial said compound of formula (Ia) or (Ib) may be reacted with a pyridine compound such as the boronic acid 1,3-propanediol cyclic ester in the presence of a suitable catalyst such as tetrakis(triphenylphosphine)-palladium and a suitable base such as potassium carbonate and in a suitable solvent such as 1,2-dimethoxyethane.

Compounds of formula (Ia) or (Ib) wherein $R^1$ is —C=N—OR$^{11}$, can be prepared from a compound of formula (Ia) or (Ib) wherein $R^1$ is formyl, by reaction with hydroxylamine hydrochloride or $C_{1-6}$alkoxylamine hydrochloride in the presence of a suitable solvent, such as for example pyridine.

Compounds of formula (Ia) or (Ib) wherein $R^1$ is —$CH_2$—$NH_2$, can be prepared from a compound of formula (Ia) or (Ib) wherein $R^1$ is formyl, by reduction in the presence of $H_2$, a suitable catalyst, such as for example palladium/carbon, and a suitable solvent, such as for example $NH_3$/alcohol, e.g. $NH_3$/methanol. Compounds of formula (Ia) or (Ib) wherein $R^1$ is —$CH_2$—$NH_2$ can be converted into a compound of formula (Ia) or (Ib) wherein $R^1$ is —$CH_2$—$N(C_{1-6}alkyl)_2$ by reaction with a suitable aldehyde or ketone reagent, such as for example paraformaldehyde or formaldehyde, in the presence of sodium cyanoborohydride, acetic acid and a suitable solvent, such as for example acetonitrile.

Compounds of formula (Ia) or (Ib) wherein $R^1$ is $R^{9a}R^{10a}N$—$CH_2$—, can be prepared by reacting a compound of formula (Ia) or (Ib) wherein $R^1$ is formyl, with a suitable reagent of formula $R^{9a}R^{10a}N$—H in the presence of a suitable reducing agent, such as for example $BH_3CN$, a suitable solvent, such as for example acetonitrile and tetrahydrofuran, and a suitable acid, such as for example acetic acid.

Compounds of formula (Ia) or (Ib) wherein $R^1$ is amino, can be prepared by reacting a compound of formula (Ia) or (Ib) wherein $R^1$ is carboxyl, with a suitable azide, such as for example diphenylphosphorylazide (DPPA), and a suitable base, such as for example triethylamine, in a suitable solvent, such as for example toluene. The obtained product undergoes a Curtius reaction, and by adding trimethylsilylethanol a carbamate intermediate is formed. In a next step, this intermediate is reacted with tetrabutylammonium bromide (TBAB) in a suitable solvent, such as for example tetrahydrofuran to obtain the amino derivative.

Compounds of formula (Ia) or (Ib) wherein $R^1$ is aminocarbonyl, mono or di(alkyl)aminocarbonyl or $R^{9a}R^{10a}N$—C(=O)—, can be prepared by reacting a compound of formula (Ia) or (Ib) wherein $R^1$ is carboxyl, with a suitable amine, a suitable coupling reagent such as for example hydroxybenzotriazole, a suitable activating reagent such as for example 1,1'-carbonyldiimidazole or N,N'-dicyclohexylcarbodiimide or 1-(3-dimethylaminopropyl)-3-ethylcarbodiimide, a suitable base, such as for example triethylamine, and a suitable solvent, such as for example tetrahydrofuran and methylene chloride.

Compounds of formula (Ia) or (Ib) wherein $R^1$ is arylcarbonyl, can be prepared by reacting in a first step (a) a compound of formula (Ia) or (Ib) wherein $R^1$ is halo, e.g. bromo and the like, with a suitable arylaldehyde in the presence of n-butyl-lithium and a suitable solvent, such as for example tetrahydrofuran. This reaction is preferably performed at low temperature such as for example −70° C. In a next step (b), the product obtained in step (a) is oxidized with a suitable oxidizing agent, such as for example manganese oxide, in the presence of a suitable solvent, such as for example methylene chloride.

Compounds of formula (Ia) or (Ib) wherein $R^4$ is phenyl substituted with halo, can be converted into a compound of formula (Ia) or (Ib) wherein $R^4$ is phenyl substituted with Het, by reaction with Het-B(OH)$_2$ in the presence of a suitable catalyst, such as for example Pd(PPh$_3$)$_4$, in the presence of a suitable base, such as for example Na$_2$CO$_3$, and a suitable solvent, such as for example toluene or 1,2-dimethoxyethane (DME) and an alcohol, for example methanol.

Compounds of formula (Ia) or (Ib) wherein $R^1$ is halo, in particular bromo, can be converted into a compound of formula (Ia) or (Ib) wherein $R^1$ is cyano by reaction with a cyano derivative for example zinc cyanide in the presence of tris[μ-[(1,2-η:4,5-η)-(1E,4E)-1,5-diphenyl-1,4-pentadien-3-one]] dipalladium (Pd$_2$(dba)$_3$) and [1,1'-bis(diphenylphosphino-κP)ferrocene]dichloropalladium (dppf) in a suitable solvent such as for example dimethylformamide.

Compounds of formula (Ia) wherein $R^2$ is methoxy, can be converted into a corresponding compound of formula (Ib) wherein $R^8$ is hydrogen and $R^9$ is oxo, by hydrolysis in the presence of a suitable acid, such as for example hydrochloric acid, and a suitable solvent, such as for example dioxane or tetrahydrofuran.

Compounds of formula (Ia) or (Ib) wherein $R^6$ is hydrogen can be converted into corresponding compounds of formula (Ia) or (Ib) wherein $R^6$ is other than hydrogen using conventional techniques. For example a compound of formula (Ia) or (Ib) wherein $R^6$ is $C_{1-6}$alkyl can be prepared by alkylation of a compound of formula (Ia) or (Ib) wherein $R^6$ is hydrogen, for example in the case where $R^6$ is methyl by treatment with aqueous formaldehyde in the presence of sodium triacetoxyborohydride in a suitable solvent such as dichloromethane. A compound of formula (Ia) or (Ib) wherein $R^6$ is aryl$C_{1-6}$alkyl can be prepared by arylalkylation of a compound of formula (Ia) or (Ib) wherein $R^6$ is hydrogen, for example by treatment with an appropriate aryl$C_{1-6}$alkyl halide in the presence of a base such as potassium carbonate in a suitable solvent such as acetonitrile. A compound of formula (Ia) or (Ib) wherein $R^6$ is aryl$C_{1-6}$alkyl can be prepared by treatment of a compound of formula (Ia) or (Ib) wherein $R^6$ is hydrogen, for example by treatment with an appropriate aldehyde such as benzaldehyde with sodium triactoxyborohydride in a suitable solvent such as dichloromethane.

Compounds of formula (Ia) or (Ib) wherein $R^6$ is hydrogen can be converted into a corresponding compound of formula (Ia) or (Ib) wherein $R^6$ is —C(=NH)—$NH_2$ for example by treatment with 1H-pyrazole-1-carboxamidine and a base such as triethylamine in a suitable solvent such as actonitrile.

Compounds of formula (Ia) or (Ib) wherein $R^6$ is other than hydrogen can be converted into a corresponding compound of formula (Ia) or (Ib) wherein $R^6$ is hydrogen using conventional techniques. For example, a compound of formula (Ia) or (Ib) wherein $R^6$ is an aryl$C_{1-6}$ alkyl group for example an ethyl-1-phenyl group can be converted in to a corresponding compound of formula (Ia) or (Ib) wherein $R^6$ is hydrogen by hydrogenation in the presence of palladium/carbon in a suitable solvent such as methanol.

It is evident that in the foregoing and in the following reactions, the reaction products may be isolated from the reaction medium and, if necessary, further purified according to methodologies generally known in the art, such as extraction, crystallization and chromatography. It is further evident that reaction products that exist in more than one enantiomeric form, may be isolated from their mixture by known techniques, in particular preparative chromatography, such as preparative HPLC, chiral chromatography. Individual diastereoisomers or individual enantiomers can also be obtained by Supercritical Fluid Chromatography (SCF).

The starting materials and the intermediates are compounds that are either commercially available or may be prepared according to conventional reaction procedures generally known in the art. Piperidone compounds useful as starting materials in the above processes can be prepared for example in accordance with the procedures described in Xiaocong M. Ye el, Bioorganic & Medicinal Chemistry Letters, 20 (2010) 2195-2199, Michel Guillaume et al, Organic Process Research and Development 2007, 11, 1079-1086 and WO 2005/123081. Various procedures for the preparation of compounds useful as the quinoline starting materials are described in the WO specifications herein referred to above.

In particular, the intermediates of formula (II-a) can be prepared according to the following reaction scheme (1):

Scheme 1

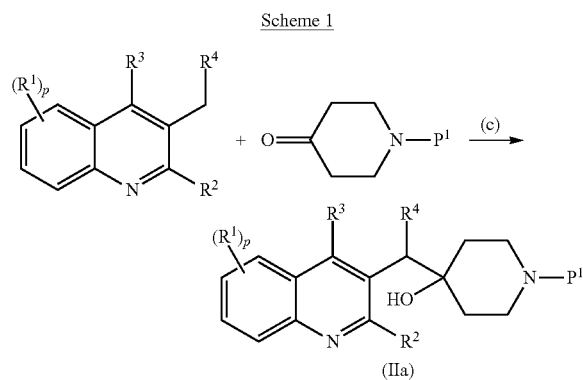

(IIa)

In reaction scheme (1), the quinoline compound is reacted with a piperidin-4-one derivative for example with n-butyl-lithium in hexane in a suitable solvent such as tetrahydrofuran.

The quinoline starting material used in scheme (1) can be prepared in conventional manner for example in accordance with the following scheme (1-a) when $R^3$ is hydrogen:

Scheme 1-a

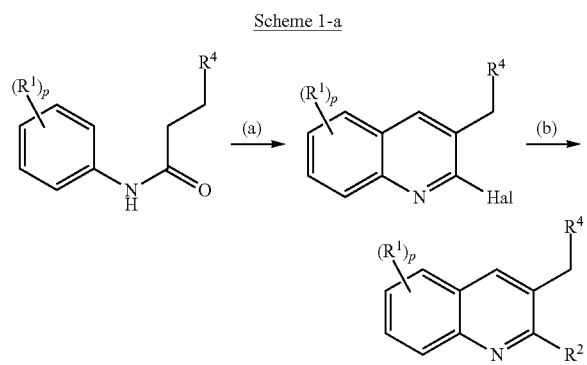

In scheme (1-a), step (a) comprises the cyclisation of a benzene propanamide compound with conversion of the oxo group to a halo (Hal) group preferably chloro for example by treatment with phosphorus oxychloride in a suitable solvent such as dimethylformamide.

In step (b), the resulting halo (Hal) group can be converted into the appropriate $R^2$ group in conventional manner for example by treatment with an alkoxide compound such as sodium methoxide to form a $C_{1-6}$alkyloxy group especially a methyloxy group, in a suitable solvent such as methanol.

The quinoline starting material used in scheme (1) can be prepared in accordance with the following scheme (1-b) when $R^3$ is halo especially chloro:

Scheme 1-b

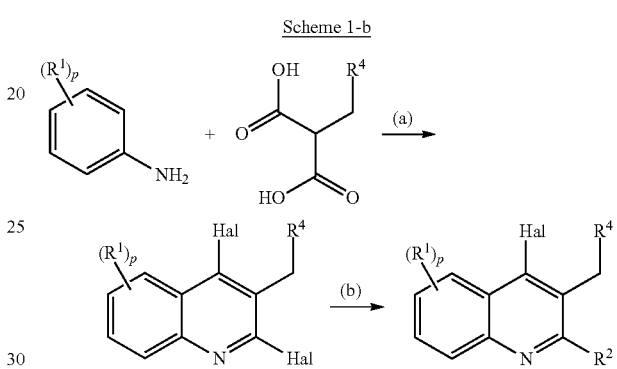

In scheme (1-b), step (a) comprises the reaction of an aminobenzene derivative with a benzenepropanoic acid derivative in the presence of a halogenating agent especially a chlorinating agent such as phosphorus trichloride at an elevated temperature for example about 80° C.

In step (b) the 2-Hal group can be converted into the desired $R^2$ group in conventional manner for example with an appropriate alkyloxylating agent such as a sodium alkoxide for example sodium methoxide to introduce an alkyloxy group preferably in a suitable solvent such methanol.

The quinoline starting material used in scheme (1) can be prepared in accordance with the following scheme (1-c) when $R^3$ is alkyl, aryl or Het:

Scheme 1-c

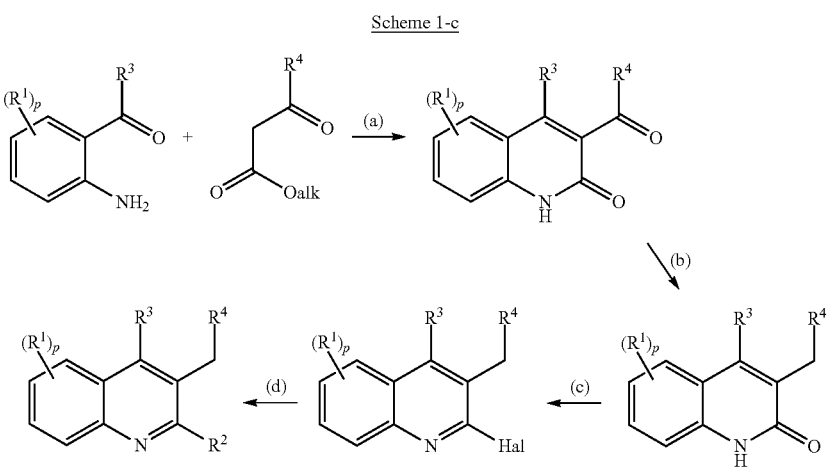

In Scheme (1-c), step (a) comprises the reaction of an aminophenylalkanone with an appropriate β-oxobenzene (or heterocyclyl)-propanoic acid alkyl (alk) ester preferably the benzenepropanoic acid ester for example the ethyl ester at an elevated temperature for example about 180° C.

In step (b) the resulting quinoline derivative is reduced to convert the oxo group attached to the 3-position of the quinoline nucleus to a methylene (—CH$_2$—) group for example by reaction with hydrazine in a suitable solvent such as 1,2-ethanediol, preferably at an elevated temperature such as about 100° C., followed by the addition of a base such as potassium hydroxide.

In step (c) the 2-oxo group can be converted into a halo (Hal) group for example a chloro group in conventional manner by treatment with an appropriate halogenating agent such as phosphorus oxychloride in the presence of benzyltriethylammonium chloride in an appropriate solvent such acetone, preferably at an elevated temperature such as 80° C.

In step (d) the 2-halo group can be converted in conventional manner into the desired $R^2$ group for example with an appropriate alkyloxylating agent such as a sodium alkoxide for example sodium methoxide to introduce an alkyloxy group preferably in a suitable solvent such methanol.

The piperidin-4-one derivatives used in scheme (1) are generally known and may be prepared by processes known, or analogous to those known, in the literature. For example, such derivatives can be prepared according to the following reaction scheme (2).

Scheme 2

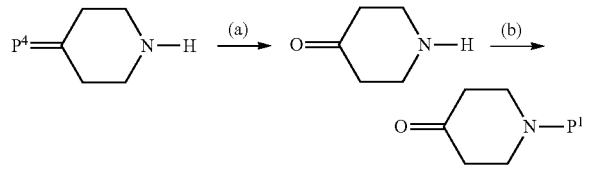

In step (a), a piperidine derivative in which $P^4$ represents a precursor group for the oxo group such as a $C_{1-4}$ alkylenedioxydioxy group especially the 1,2-ethylenedioxy group is treated to convert the precursor group to the desired oxo group for example by treatment with an acid such as hydrochloric acid to effect conversion of the $C_{1-4}$ alkylenedioxy group to the oxo group. In step (b) the protecting group $P^1$ can be introduced in conventional manner. Thus, for example, when the $\alpha^1$ group is a $C_{1-6}$alkyloxycarbonyl group, the piperdin-4-one compound can be reacted with an appropriate di-$C_{1-6}$ alkyl dicarbonate such as di-tert-butyl dicarbonate in the presence of a base such as triethylamine and in a suitable solvent such as tetrahydrofuran.

Alternatively the above piperidin-4-one derivative can be prepared by reduction of a corresponding 3,4-dihydropyridine compound according to reaction scheme (3):

Scheme 3

In this reaction the 3,4-dihydropyridine compound is reduced for example with a reducing agent such as lithium hydrotris(1-methylpropyl) (1-)borate in a suitable solvent such as tetrahydrofuran, preferably at a temperature of about −78° C.

Experimental Part

Of some compounds or intermediates the absolute stereochemical configuration of the stereogenic carbon atom(s) therein or the configuration at the double bond was not experimentally determined. However, such isomeric forms can be unambiguously characterized by a person skilled in the art, using art-known methods such as, for example, NMR. It is considered to be within the knowledge of the skilled person to recognize the most appropriate method to determine the actual stereochemical configuration.

Hereinafter "BTEAC" means benzyltriethylammonium chloride, "n-BuLi" means n-butyl lithium, "DCM" means dichloromethane (CH$_2$Cl$_2$), "DIPE" means diisopropyl ether, "DME" means 1,2-dimethoxyethane, "DMF" means N,N-dimethylformamide, "dppf" means [1,1'-bis(diphenylphosphino-κP)ferrocene]dichloropalladium, "EtOAc" means ethyl acetate, "EtOH" means ethanol, "MeOH" means methanol (CH$_3$OH), "Pd$_2$(dba)$_3$" means tris[μ-[(1,2-η:4,5-η)-(1E,4E)-1,5-diphenyl-1,4-pentadien-3-one]]dipalladium (also tris(dibenzylideneacetone)dipalladium), "RT" means room temperature, "RM" means reaction mixture, "THF" means tetrahydrofuran, and "SFC" means Supercritical Fluid Chromatography.

A. Preparation of the Intermediates

Example A1

Preparation of Intermediate 1

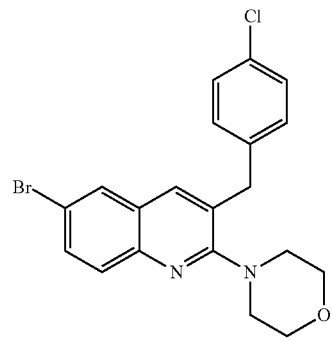 [SMILES: Clc1ccc(Cc2cc3cc(Br)ccc3nc2N2CCOCC2)cc1]

A mixture of 6-bromo-2-chloro-3-[(4-chlorophenyl)methyl]quinoline (1 g, 0.0027 mol) in morpholine (4.5 ml) was stirred at 90° C. overnight, poured into ice water. The precipitate was filtered, washed with H$_2$O and dried at 60° C. in vacuo, yielding 1.01 g (90%) of intermediate 1.

Example A2 a) Preparation of Intermediate 2

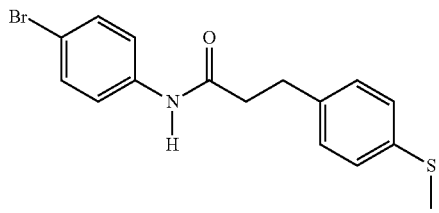 [SMILES: CSc1ccc(CCC(=O)Nc2ccc(Br)cc2)cc1]

A solution of 4-(methylthio)benzenepropanoyl chloride (9 g, 0.042 mol) in CH$_2$Cl$_2$ (80 ml) was added dropwise at 0° C. to a solution of 4-bromobenzenamine (7.19 g, 0.042 mol) and N,N-diethylethanamine (6.4 ml, 0.046 mol) in CH$_2$Cl$_2$ (70 ml). The mixture was stirred at RT overnight and poured into water. The organic layer was extracted with CH$_2$Cl$_2$, washed with water, dried (MgSO$_4$), filtered and the solvent was evaporated to dryness. The residue was crystallized from DIPE/CH$_2$Cl$_2$. The precipitate was filtered off and dried, yielding 5.5 g (38%) of intermediate 2.

b) Preparation of Intermediate 3

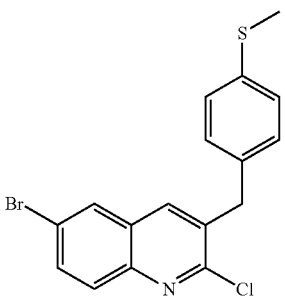 [SMILES: CSc1ccc(Cc2cc3cc(Br)ccc3nc2Cl)cc1]

DMF (1.81 ml, 0.0236 mol) then intermediate 2 (5.5 g, 0.0157 mol) were added portionwise at 5° C. to POCl$_3$ (10.2 ml, 0.011 mol). The mixture was stirred at 90° C. overnight, then cooled to RT and poured into ice water. The organic layer was extracted with CH$_2$Cl$_2$, washed with 10% aqueous K$_2$CO$_3$ solution, dried (MgSO$_4$), filtered and the solvent was evaporated to dryness. The residue was purified by column chromatography over silica gel (eluent: cyclohexane/CH$_2$Cl$_2$ 50/50; 15-40 μm). The pure fractions were collected and the solvent was evaporated to dryness, yielding: 2.15 g of intermediate 3.

c) Preparation of Intermediate 4

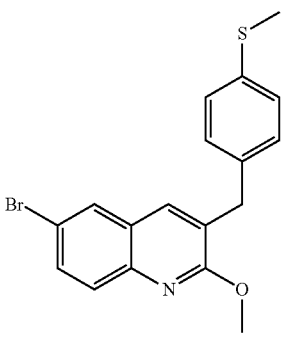 [SMILES: COc1nc2ccc(Br)cc2cc1Cc1ccc(SC)cc1]

A solution of intermediate 3 (2.15 g, 0.0057 mol) in CH$_3$ONa 33% in CH$_3$OH (5.6 ml) and CH$_3$OH (50 ml) was stirred and refluxed overnight, then cooled to 0° C. The precipitate was filtered, washed with CH$_3$OH and dried at 60° C. in vacuo, yielding: 1.75 g (82%) of intermediate 4.

d) Preparation of Intermediate 5

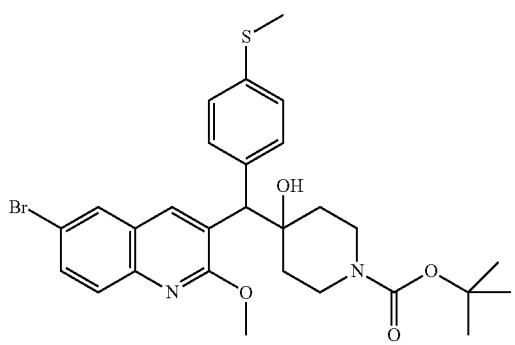 [SMILES: COc1nc2ccc(Br)cc2cc1C(c1ccc(SC)cc1)C1(O)CCN(C(=O)OC(C)(C)C)CC1]

n-BuLi 1.6M in hexane (8.015 ml, 12.824 mol) was added dropwise at −20° C. to a solution of diisopropylamine (1.797 ml, 12.824 mmol) in THF (18 ml) under N$_2$ flow. The mixture was stirred at −20° C. for 20 minutes, then cooled to −70° C. A solution of intermediate 4 (4 g, 10.687 mmol) in THF (40 ml) was added. The mixture was stirred for 1 hour at −70° C. A solution of 1,1-dimethylethyl 4-oxo-1-piperidinecarboxylic acid ester (3.194 g, 16.03 mmol) in THF (16 ml) was added at −70° C. then stirred at −70° C. for 1 hour. Water and EtOAc were added at −30° C. The organic layer was separated, washed with water then brine, dried (MgSO$_4$), filtered and the solvent was evaporated to dryness. The residue (7.5 g) was purified by column chromatography over silica gel (Merck, 200 g, SiO$_2$ 15-40 μm; eluent: cyclohexane/EtOAc: 80/20). The pure fractions were collected and the solvent was evaporated to dryness, yielding 1.95 g (32%) of intermediate 5.

e) Preparation of Intermediate 6

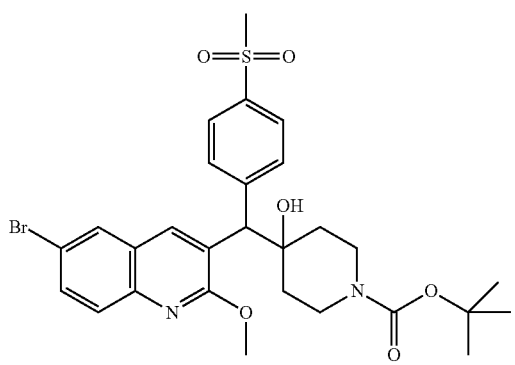 [SMILES: COc1nc2ccc(Br)cc2cc1C(c1ccc(S(C)(=O)=O)cc1)C1(O)CCN(C(=O)OC(C)(C)C)CC1]

A mixture of intermediate 5 (1.95 g, 3.4 mmol) and 3-chloroperoxybenzoic acid (2.514 g, 10.2 mmol) in DCM (40 ml) was stirred overnight. The mixture was poured into 10% aqueous potassium carbonate solution and extracted with DCM. The organic layer was separated, washed with water, dried over MgSO$_4$, filtered and the solvent evaporated to dryness yielding 2.6 g (106.859%) of intermediate 6.

Example A3 a) Preparation of Intermediate 7

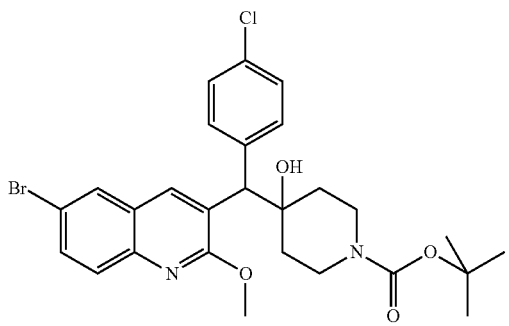 [SMILES: COc1nc2ccc(Br)cc2cc1C(c1ccc(Cl)cc1)C1(O)CCN(C(=O)OC(C)(C)C)CC1]

Intermediate 7 was prepared in an analogous manner to intermediate 5 starting from 6-bromo-3-[(4-chlorophenyl)methyl]-2-methoxyquinoline (5 g, 13.787 mmol) and 1,1-dimethylethyl 4-oxo-1-piperidinecarboxylic acid ester (3.297 g, 16.545 mmol). The residue was purified by column chromatography over silica gel (B6745; SiO$_2$ 10-40 μm; 450 g; cyclohexane/EtOAc 90/10). The desired fraction was collected and the eluent was evaporated, yielding 3.2 g (41.31%) of intermediate 7.

b) Preparation of Intermediate 8

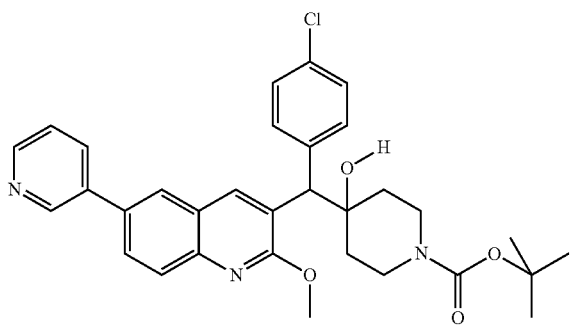 [SMILES: COc1nc2ccc(-c3cccnc3)cc2cc1C(c1ccc(Cl)cc1)C1(O)CCN(C(=O)OC(C)(C)C)CC1]

A solution of intermediate 7 (3.92 g, 0.0070 mol), 3-(1,3,2-dioxaborinan-2-yl)pyridine (2.27 g, 0.0140 mol) and Pd(PPh$_3$)$_4$ in DME (99 ml), MeOH (52 ml) and 2M K$_2$CO$_3$ solution (14.4 ml) was stirred for two hours at 90° C., then cooled to room temperature, poured into water and extracted with DCM. The organic layer was separated, dried over MgSO$_4$, filtered and the solvent evaporated. The residue was purified by column chromatography over silica gel (eluent: CH$_2$Cl$_2$/CH$_3$OH/NH$_4$OH from 99/1/0.1 to 94/6/0.6). The pure fractions were collected and the solvent was evaporated, yielding: 3.14 g (80%) of intermediate 8.

Example A4 a) Preparation of Intermediate 9

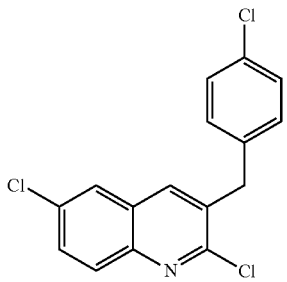 [SMILES: Clc1ccc(Cc2cc3cc(Cl)ccc3nc2Cl)cc1]

DMF (9.71 ml, 0.126 mol) was added dropwise to POCl$_3$ (54.89 ml, 0.589 mol) at 5° C. then 4-chloro-N-(4-chlorophenyl)benzenepropanamide (24.75 g, 84.132 mmol) was added portionwise at 5° C. The resulting mixture was heated at 80° C. overnight then cooled to RT and poured into water and ice. The precipitate was filtered off, washed with water, and taken up in DIPE. The precipitate was filtered off and dried (vacuum, 60° C.), yielding 26.67 g (98%) of intermediate 9.

b) Preparation of Intermediate 10

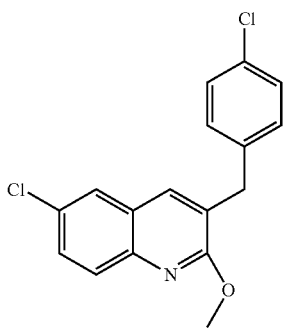 [SMILES: COc1nc2ccc(Cl)cc2cc1Cc1ccc(Cl)cc1]

CH$_3$ONa 30% in CH$_3$OH (110.272 ml, 0.579 mol) was added to a solution of intermediate 9 (26.67 g, 82.667 mmol) in methanol (518 ml). The mixture was stirred at 80° C. overnight, then cooled to RT and the solvent was evaporated under reduced pressure. The mixture was poured onto water and ice and the precipitate was filtered off, and washed with water. The powder was dried under vacuum at 60° C., yielding 21.4 g (81%) of intermediate 10.

c) Preparation of Intermediate 11

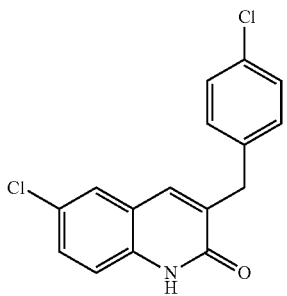 [SMILES: O=c1[nH]c2ccc(Cl)cc2cc1Cc1ccc(Cl)cc1]

HCl 3N (50 ml) was added to a solution of intermediate 10 (9.7 g, 30.484 mmol) in THF. The RM was heated at 70° C. overnight. The mixture was cooled to RT and poured into ice water. The solution was stirred for 45 min. and the precipitate was filtered, washed with water and dried under vacuum at 60° C. overnight, yielding 7.66 g (82%) of intermediate 11.

d) Preparation of Intermediate 12

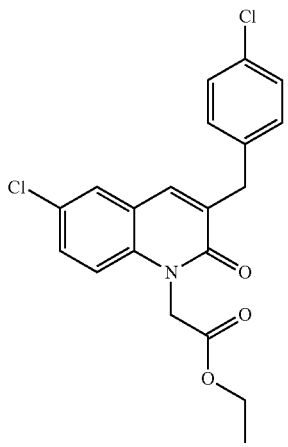 [SMILES: CCOC(=O)Cn1c(=O)c(Cc2ccc(Cl)cc2)cc2cc(Cl)ccc21]

NaH (173.568 mg, 7.233 mmol) was added to a solution of intermediate 11 (2 g, 6.575 mmol) in DMF (25 ml) at 5° C. under nitrogen. The RM was stirred for 30 minutes at RT. Then ethyl 2-bromoacetate (0.802 ml, 7.233 mmol) was added to the RM at 5° C. The RM was stirred overnight at RT. Water and EtOAc were added at RT.

The precipitate was filtered off and purified by flash chromatography over silica gel (15-40 µm, 1.95 g, cyclohexane/EtOAc 80/20). The fractions were collected and evaporated to dryness, yielding 0.89 g (34%) of intermediate 12.

The filtrate was separated, washed with water and brine, dried over MgSO$_4$ and filtered. The solvent was evaporated to dryness, yielding 1.78 g (69%) of intermediate 12.

e) Preparation of Intermediate 13

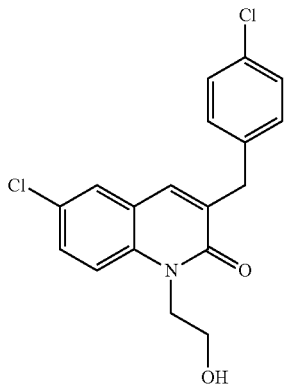 [SMILES: O=c1c(Cc2ccc(Cl)cc2)cc2cc(Cl)ccc2n1CCO]

H$_4$AlLi (48.626 mg, 1.281 mmol) was added to a solution of intermediate 12 (1 g, 2.562 mmol) in THF (10 ml) at 0° C. under nitrogen. The RM was stirred for 30 minutes at 0° C. H$_4$AlLi (0.5 eq) was added and the RM was stirred for 30 minutes at 0° C. Then EtOAc and water were added to the RM. The organic layer was separated and washed with water, dried over MgSO$_4$ and filtered. The solvent was evaporated to dryness.

The residue was purified by flash chromatography over silica gel (15-40 µm, 4.29 g, CH$_2$Cl$_2$ for 20 minutes then CH$_2$Cl$_2$/MeOH/NH$_4$OH 98/2/0.1 for 40 minutes). The pure fraction was collected and the eluent was evaporated, yielding intermediate 13, used in the next step procedure. More product can be obtained from the impure fraction by further purifications.

f) Preparation of Intermediate 14

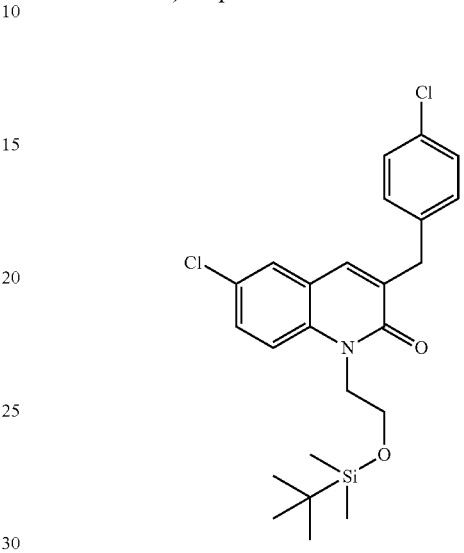

A solution of intermediate 13 (805 mg, 2.312 mmol), (1,1-dimethylethyl)dimethylsilyl 1,1,1-trifluoromethanesulfonic acid, ester (916.617 mg, 3.468 mmol) and pyridine (0.28 ml, 3.468 mmol) in DCM (2 ml) was stirred at RT for 7 hours. MeOH (800 µl) was added to the RM and it was poured into 10% aqueous K$_2$CO$_3$ solution. The mixture was extracted with CH$_2$Cl$_2$. The organic fraction was separated, washed with water, dried over MgSO$_4$ and evaporated to dryness. The residue was purified by flash chromatography over silica gel (15-40 µm, 0.915 g, cyclohexane/EtOAc 70/30).

The pure fractions were collected and evaporated to dryness, yielding intermediate 14, used in the next step procedure.

g) Preparation of Intermediate 15

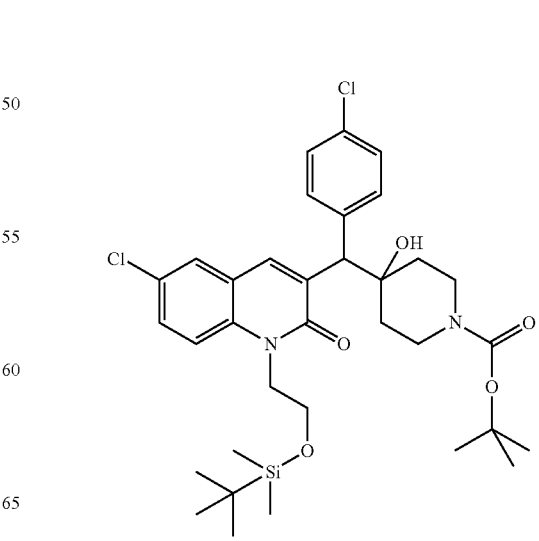

n-BuLi 1.6M in hexane (0.973 ml, 1.557 mmol) was added dropwise to a solution of diisopropylamine (0.219 ml, 1.557 mmol, 0.72 g/ml) in THF (2 ml) at −20° C. The mixture was stirred for 20 minutes at this temperature then cooled to −78° C. A solution of intermediate 14 (600 mg, 1.297 mmol) in THF (6 ml) was added then stirred at −78° C. for one hour. A solution of 1,1-dimethylethyl 4-oxo-1-piperidinecarboxylic acid ester (310.19 mg, 1.557 mmol) in THF (3 ml) was added at −78° C. then stirred for one hour at −78° C. Water and EtOAc were added, the organic layer was separated, washed with water then brine, dried over MgSO$_4$, filtered and evaporated to dryness.

The residue was purified by flash chromatography over silica gel (15-40 μm, 800 mg, cyclohexane/EtOAc 90/10 to 80/20). The pure fractions were collected and evaporated to dryness, yielding 614 mg (71.5%) of intermediate 15.

h) Preparation of Intermediate 16

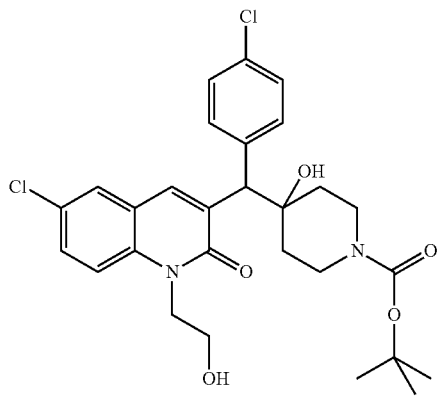 [SMILES: CC(C)(C)OC(=O)N1CCC(O)(C(c2ccc(Cl)cc2)c2cc3cc(Cl)ccc3n(CCO)c2=O)CC1]

A solution of intermediate 15 (520 mg, 0.786 mmol) and tetrabutylammonium fluoride (0.943 ml, 0.943 mmol) in THF (5 ml) was stirred for 2 hours at 0° C. Water and EtOAc were added, the organic layer was separated, washed with water and brine, dried over MgSO$_4$, filtered and the solvent was evaporated to dryness, yielding 535 mg of intermediate 16.

i) Preparation of Intermediate 17

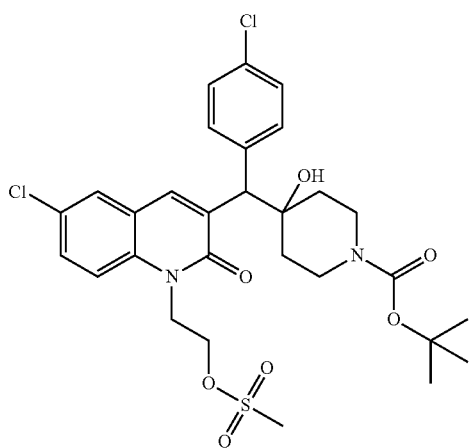 [SMILES: CC(C)(C)OC(=O)N1CCC(O)(C(c2ccc(Cl)cc2)c2cc3cc(Cl)ccc3n(CCOS(C)(=O)=O)c2=O)CC1]

Methanesulfonyl chloride (0.0537 ml, 0.694 mmol) was added to a solution of intermediate 16 (380 mg, 0.694 mmol) and N,N-diethylethanamine (0.0965 ml, 0.694 mmol) in DCM (4 ml) at 0° C. The RM was stirred for 2 hours at 0° C. The solvent was evaporated to dryness, yielding 600 mg of intermediate 17.

j) Preparation of Intermediate 18

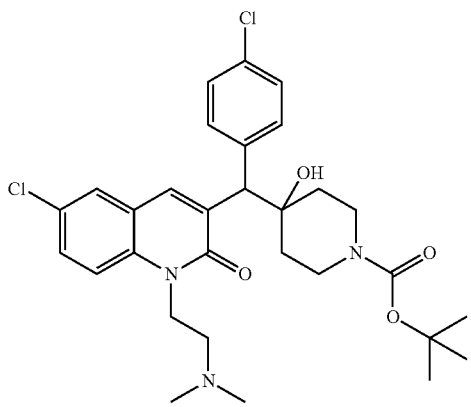 [SMILES: CN(C)CCn1c(=O)c(C(c2ccc(Cl)cc2)C2(O)CCN(C(=O)OC(C)(C)C)CC2)cc2cc(Cl)ccc21]

A solution of intermediate 17 (600 mg, 0.959 mmol), N-methylmethanamine (216.208 mg, 4.796 mmol) and K$_2$CO$_3$ (662.784 mg, 4.796 mmol) in acetonitrile (6 ml) was stirred at reflux (81° C.) overnight. EtOAc and water were added to the RM, the organic layer was washed with water and brine, dried, filtered and the solvent was evaporated. The residue was purified by flash chromatography over silica gel (15-40 μm, mg, CH$_2$Cl$_2$/MeOH/NH$_4$OH 95/5/0.1). The pure fractions were collected and evaporated to dryness, yielding 171 mg (31%) of intermediate 18.

Example A5 a) Preparation of Intermediate 19

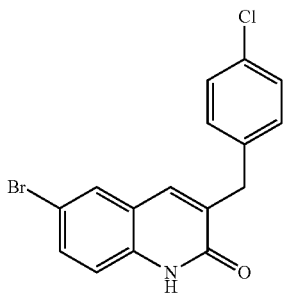

A solution of 6-bromo-3-[(4-chlorophenyl)methyl]-2-methoxyquinoline (10 g, 27.6 mmol), 3N HCl (100 ml) and THF (100 ml) was heated at 70° C. overnight. The mixture was cooled to RT and poured into ice water. The solution was stirred for 30 minutes and the precipitate was filtered, washed was with water and dried in vacuo at 60° C., yielding 9.56 g (99.4%) of intermediate 19; mp 220° C.

b) Preparation of Intermediate 20

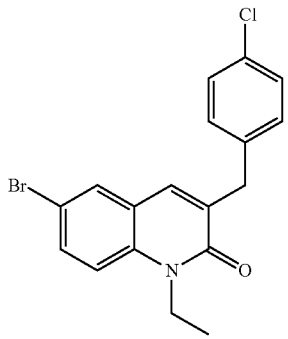 [SMILES: CCn1c(=O)c(Cc2ccc(Cl)cc2)cc2cc(Br)ccc21]

Ethyl iodide (3.29 ml, 41.13 mmol) was added to a solution of intermediate 19 (4.78 mg, 13.71 mmol), BTEAC (1.56 g, 6.85 mmol) and 10N NaOH (67 ml) in THF (50 ml). The mixture was poured into water and extracted with EtOAc. The combined organic layers were washed with brine, dried over MgSO$_4$, filtered and concentrated. The residue was purified by column chromatography over silica gel (eluent: DCM 100%, 15-40 μm).

The pure fractions were collected and evaporated, yielding 3 g (58%) of intermediate 20; mp 118° C.

B. Preparation of the Compounds

Example B1

Preparation of Compound 1

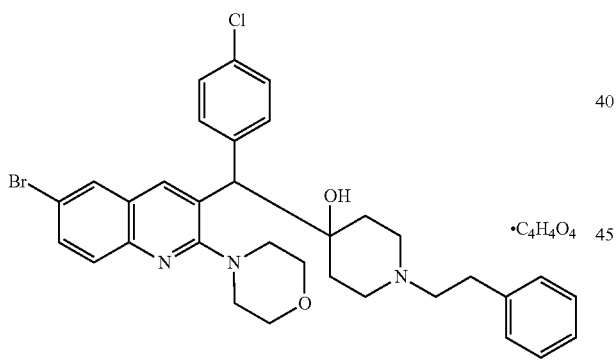

n-BuLi 1.6M in hexane (0.84 ml, 0.0013 mol) was added dropwise at −20° C. to a solution of N-(1-methylethyl)-2-propanamine (0.19 ml, 0.0013 mol) in THF (2.7 ml) under N$_2$ flow. The mixture was stirred at −20° C. for 20 minutes, then cooled to −70° C. A solution of intermediate 1 (0.508 g, 0.0012 mol) in THF (5 ml) was added. The mixture was stirred for 1.5 hours. A solution of 1-(2-phenylethyl)-4-piperidone (0.222 g, 0.0010 mol) in THF (2 ml) was added dropwise. The mixture was stirred at −70° C. for 2 hours, then brought to −30° C., poured out into H$_2$O and extracted with EtOAc. The organic layer was washed with saturated NaCl, dried (MgSO$_4$), filtered and the solvent was evaporated. The residue was purified by column chromatography over silica gel (eluent: CH$_2$Cl$_2$/CH$_3$OH 98/2; 15-40 μm). The pure fractions were collected and the solvent was evaporated. The residue was dissolved in 2-propanone/fumaric acid (3 eq) and converted into the fumaric acid salt. The precipitate was stirred for 1 hour, filtered, washed with 2-propanone and dried at 60° C. in vacuo, yielding: 0.194 g (92%) of compound 1; mp. 158° C.

Example B2 a) Preparation of Compound 2

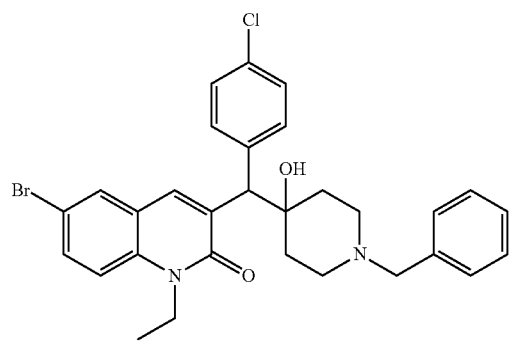 [SMILES: CCn1c(=O)c(C(c2ccc(Cl)cc2)C2(O)CCN(Cc3ccccc3)CC2)cc2cc(Br)ccc21]

n-BuLi 1.6M in hexane (3 ml. 4.78 mmol) was added slowly at −20° C. under a nitrogen flow to a solution of diisopropylamine (0.67 ml, 4.78 mmol) in THF (7 ml). The mixture was stirred at −20° C. for 20 minutes, then cooled to −70° C. A solution of intermediate 20 (1.5 g, 3.98 mmol) in THF (15 ml) was added slowly. The mixture was stirred at −70° C. for 1.5 hours. A solution of 1-phenylmethyl-4-piperidone (0.785 ml. 4.38 mmol) in THF (8 ml) was added slowly. The mixture was stirred at −70° C. for two hours, hydrolysed at −30° C. with ice water and extracted with EtOAc. The organic layer was separated, dried over MgSO$_4$, filtered and the solvent evaporated. The residue was purified by column chromatography over silica gel (15-40 μm, DCM/MeOH/NH$_4$OH: 97/3/0.1). The pure fractions were collected and evaporated to dryness, yielding a white foam which was crystallised in acetone (3 ml), yielding 0.105 g of compound 2; mp 212° C.

b) Preparation of Compound 3

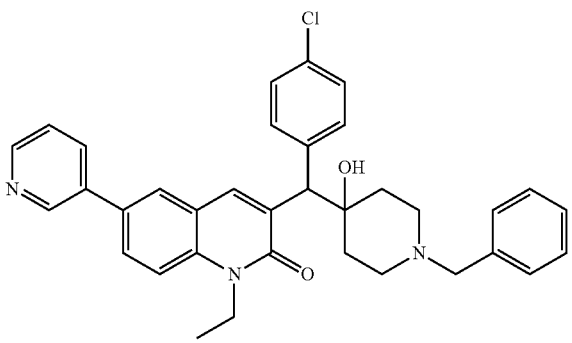 [SMILES: CCn1c(=O)c(C(c2ccc(Cl)cc2)C2(O)CCN(Cc3ccccc3)CC2)cc2cc(-c3cccnc3)ccc21]

A mixture of compound 2 (0.42 g, 0.7 mmol), 3-(1,3,2-dioxaborinan-2-yl)pyridine (0.241 g, 1.5 mmol) and tetrakis(triphenylphosphine) palladium (0.086 g) in DME (10 ml), CH$_3$OH (8 ml) and a solution of potassium carbonate 2M (1.8 ml) was stirred at 90° C. for 4 hours. After cooling to RT, the reaction mixture was poured out into water and extracted with CH$_2$Cl$_2$. The organic layer was separated, dried (MgSO$_4$), filtered and the solvent was evaporated. The residue was purified by column chromatography over silica gel (eluent: CH₂Cl₂/CH₃OH/NH₄OH; 98/2/0.1). The pure fraction was collected and the solvent was evaporated. The residue was crystallized from 2-propanone. The precipitate was filtered off and dried, yielding: 0.117 g (28%) of compound 3, mp. 172° C.

c) Preparation of Compound 4

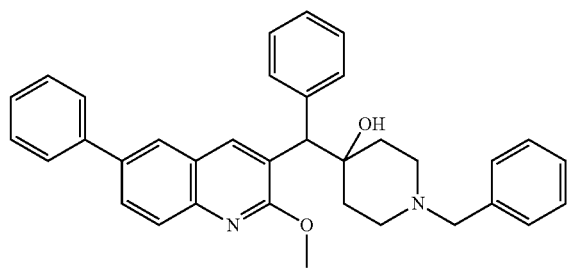 [SMILES: COc1nc2ccc(-c3ccccc3)cc2cc1C(c1ccccc1)C1(O)CCN(Cc2ccccc2)CC1]

A mixture of compound 29 (0.15 g, 0.2 mmol), phenylboronic acid (0.053 g, 0.4 mmol) and Pd(PPh₃)₄ (0.34 g, 0.3 mmol) in DME (4 ml), MeOH ((2 ml) and 2M potassium carbonate solution (0.3 ml) was stirred at 90° C. for 2 hours, then poured into water and DCM. The organic layer was separated, dried (MgSO₄), filtered and the solvent evaporated. The residue was purified by column chromatography over silica gel (eluent: CH₂Cl₂/CH₃OH 97/3; 15-40 μm). The pure fractions were collected and the solvent was evaporated, yielding 0.108 g (73%) of compound 4.

Example B3

Preparation of Compound 5

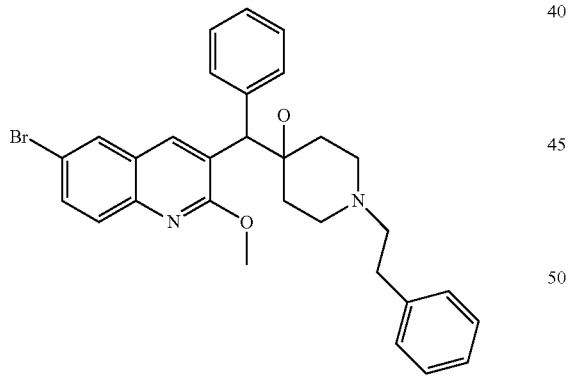

3-Benzyl-6-bromo-2-methoxyquinoline (0.00091 mol) was dissolved in THF (6 ml) and this solution was cooled to −70° C. under Ar atmosphere. Lithium-diisopropylamine 2M in THF/heptanes/ethylbenzene (0.00100 mol) was added dropwise and the reaction mixture was stirred for 1.5 hours at −70° C. A solution of 1-(2-phenylethyl)-4-piperidone (0.00109 mol) in THF (4 ml) was added and the resulting reaction mixture was stirred for 1.5 hours at −70° C., then for one hour at 0° C. The reaction solution was hydrolysed at −10° C. by adding ice-water. This mixture was extracted twice with diethyl ether and twice with DCM. The organic layer was separated, dried (Na₂SO₄), filtered and the solvent was evaporated. The residue (0.519 g) was purified by column chromatography over silica gel (eluent: petroleum ether/diethyl ether//NH₄OH 10/1/0.1, 5/1/0.1, 2/1/0.1 to pure diethyl ether). The product fractions were collected and the solvent was evaporated, yielding 0.100 g of compound 5.

Example B4 a) Preparation of Compound 6

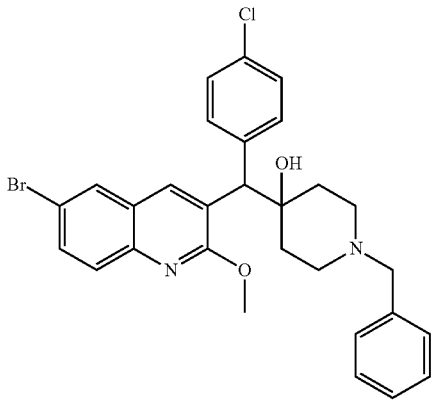 [SMILES: COc1nc2ccc(Br)cc2cc1C(c1ccc(Cl)cc1)C1(O)CCN(Cc2ccccc2)CC1]

n-BuLi 1.6M in hexane (0.84 ml, 0.0013 mol) was added dropwise at −20° C. to a solution of N-(1-methylethyl)-2-propanamine (0.19 ml, 0.0013 mol) in THF (2.7 ml) under N₂ flow. The mixture was stirred at −20° C. for 20 minutes, then cooled to −70° C. A solution of 6-bromo-3-[(4-chlorophenyl)methyl]-2-methoxyquinoline (2 g, 0.0055 mol) in THF (20 ml) was added. The mixture was stirred at −70° for one hour. A solution of 1-(phenylmethyl)-4-piperidone (1.17 ml, 0.0066 mol) in THF (12 ml) was added. The mixture was stirred at −70° C. for 3 hours. Water was added. The mixture was extracted with EtOAc. The organic layer was washed with saturated NaCl, dried (MgSO₄), filtered and the solvent was evaporated. The residue was purified by column chromatography over silica gel (eluent: cyclohexane/EtOAc: 30/70; 15-40 μm). The pure fractions were collected and the solvent was evaporated, yielding 1.8 g, 60% of compound 6.

b) Preparation of Compounds 7 and 8

Compound 7

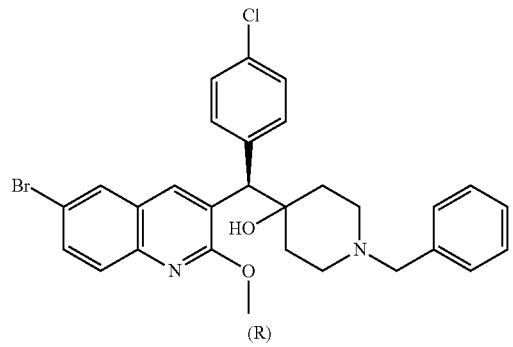

-continued

Compound 8

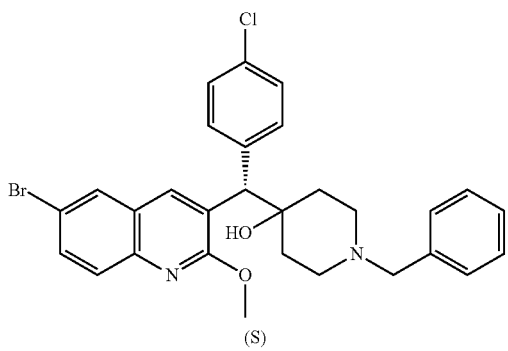

(S)

Compound 6 (0.4 g, 0.7 mmol) was divided into two enantiomers by SFC Chiralpack AD (eluent: CO₂/(CH₃CN/CH₃OH 90/10) 50/50, then CH₂Cl₂/CH₃OH 99/1). Two fractions were collected and the solvent was evaporated, yielding 0.14 g of compound 7; optical rotation: ~130.99° (589 nm, c 0.484 w/v %, DMF, 20° C.), and 0.16 g of compound 8; optical rotation: +132.07° (589 nm, c 0.421 w/v %, DMF, 20° C.).

Example B5

Preparation of Compound 9

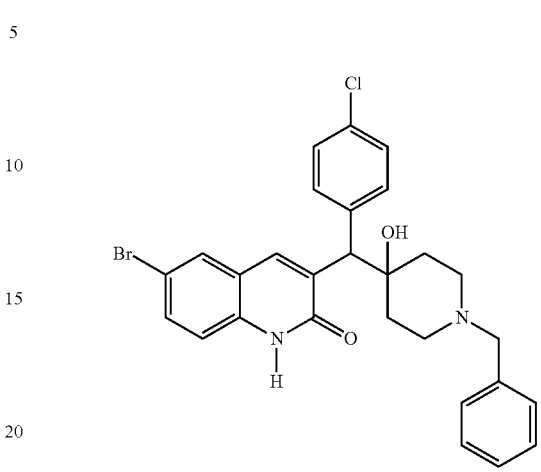

·C₄H₄O₄

A solution of intermediate 5 (0.25 g, 0.4 mmol) and trifluoroacetic acid (1 ml) in CH₂Cl₂ (5 ml) was stirred at RT for 45 minutes. The mixture was poured out into 10% K₂CO₃ aqueous solution and extracted with CH₂Cl₂. The organic layer was separated, washed with water, dried (MgSO₄), filtered and the solvent was evaporated to dryness. The residue was dissolved in 2-propanone/EtOH and converted into the (E)-2-butenedioic acid salt. The precipitate was filtered off and dried, yielding 0.146 g of compound 9 (55%), mp. 204° C.

Example B6

Preparation of Compound 10

HCl 3N (1 ml) was added to a solution of compound 6 (0.1 g, 0.1 mmol) in THF (1 ml). The mixture was stirred at 70° C. for 6 hours, then brought to RT, poured out into H₂O, basified with K₂CO₃ and extracted with EtOAc. The organic layer was washed with saturated NaCl, dried (MgSO₄), filtered and the solvent was evaporated. The residue was crystallized from diethyl ether. The precipitate was filtered off and dried, yielding 0.08 g (82%) of compound 10; mp. 244° C.

Example B7

Preparation of Compound 11

A solution of compound 6 (0.2 g, 0.3 mmol), tributylethenyl stannane (0.21 ml, 0.7 mmol) and dichlorobis(triphenylphosphine)palladium (0.025 g) in DMF (4 ml) was stirred 10 minutes at 80° C. 0.5 eq. of tributylethenyl stannane and 0.5 eq. of dichlorobis(triphenylphosphine)palladium were added. The mixture was stirred at 80° C. for 5 minutes. 0.5 eq. of tributylethenyl stannane and 0.5 eq. of dichlorobis(triphenylphosphine)palladium were added again. The mixture was stirred at 80° C. for 10 minutes and poured out into a solution of potassium fluoride. EtOAc was added.

The mixture was stirred for 1 hour, filtered over celite. The celite was washed with EtOAc. The organic layer was washed with saturated NaCl, dried (MgSO₄) filtered and the solvent was evaporated. The residue was purified by column chromatography over kromasil (eluent: CH₂Cl₂/CH₃OH 100/0 to 97/3/0.3; 3-5 μm). The pure fractions were collected and the solvent was evaporated. The residue was dissolved in 2-propanone/fumaric acid and converted into the fumaric acid salt.

The precipitate was stirred for 1 hour, filtered off, washed with 2-propanone and dried at 60° C. in vacuo, yielding 0.081 g (67%) of compound 11, mp. 195° C.

Example B8

Preparation of Compound 12

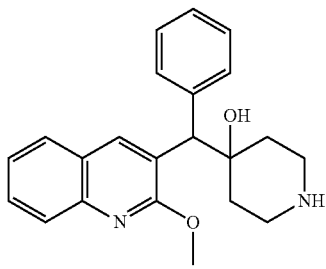 [SMILES: COc1nc2ccccc2cc1C(c1ccccc1)C1(O)CCNCC1]

Ammonium formate (0.143 g, 0.0022 mol) then palladium on charcoal (0.25 g) were added to a solution of compound 6 (0.25 g, 0.4 mmol) in $CH_3OH$ (5 ml) under $N_2$ flow. The mixture was stirred and refluxed for 1 hour and 15 minutes, then brought to RT, filtered over celite. The celite was washed with EtOAc. The filtrate was washed with saturated NaCl, dried ($MgSO_4$), filtered and the solvent was evaporated. The residue was purified by column chromatography over silica gel (eluent: $CO_2/CH_3OH$/isopropyl amine 90/10/0.5). The pure fractions were collected and the solvent was evaporated. The residue was crystallized from DIPE. The precipitate was filtered off and dried, yielding: 0.025 g (16%) of compound 12; mp. 119° C.

Example B9

Preparation of Compound 13

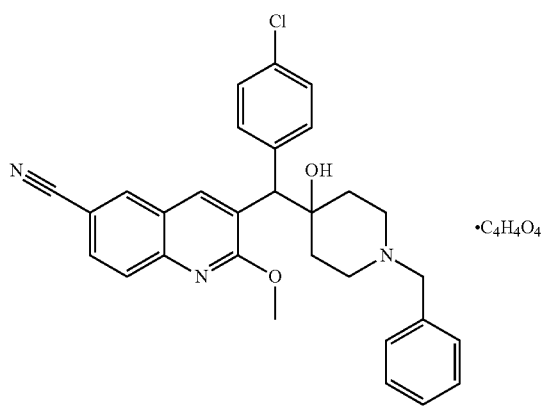

A mixture of compound 6 (0.15 g, 0.2 mmol), $Zn(CN)_2$ (0.019 g, 0.1 mmol), $Pd_2(dba)_3$ (0.012 g) and dppf (0.015 g) in DMF (1.5 ml) and $H_2O$ (15 drop) was stirred at 100° C. for 10 minutes in a microwave oven. $Zn(CN)_2$ (0.6 eq), $Pd_2(dba)_3$ (0.05 eq) and dppf (0.1 eq) were added. The mixture was stirred at 100° C. for 15 minutes in a microwave oven. $Zn(CN)_2$ (0.3 eq), $Pd_2(dba)_3$ (0.02 eq) and dppf (0.05 eq) were added. The mixture was stirred at 100° C. for 10 minutes, poured into $H_2O$ and extracted with EtOAc. The organic layer was washed with saturated NaCl, dried ($MgSO_4$), filtered and the solvent was evaporated. The residue was purified by column chromatography over Kromasil (eluent: $CH_2Cl_2/CH_3OH/NH_4OH$ 100/0/0 to 96/4/0.4; 3.55m then $CH_3OH/NH_4HCO_3$ 0.5%, 80/20; 5 µm). The pure fractions were collected and the solvent was evaporated. The residue was dissolved in 2-propanone/fumaric acid and converted into the fumaric acid salt. The precipitate was stirred for 3 hours, filtered, washed with 2-propanone and dried at 60° C. in vacuo, yielding 0.035 g (61%) of compound 13; mp. 199° C.

Example B10 a) Preparation of Compound 14

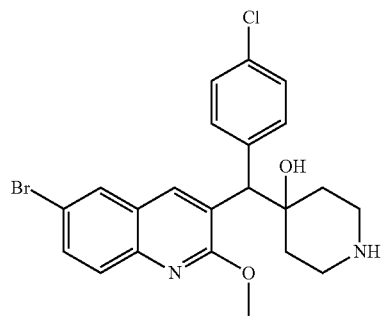 [SMILES: COc1nc2ccc(Br)cc2cc1C(c1ccc(Cl)cc1)C1(O)CCNCC1]

A mixture of intermediate 7 (2.7 g, 4.81 mmol) in trifluoroacetic acid (10 ml) and DCM (30 ml) was stirred for 30 minutes at 5° C. then for one hour at RT. The mixture was poured into 10% aqueous potassium carbonate solution and extracted with DCM. The organic layer was separated, washed with water, dried over $MgSO_4$, filtered and the solvent evaporated to dryness, yielding 1.12 g (50%) of compound 14, mp 169° C.

b) Preparation of compound 15

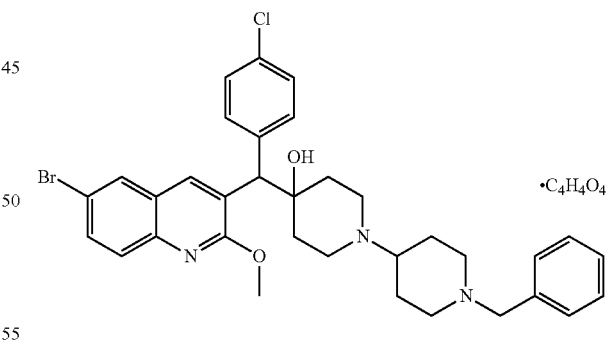

A mixture of compound 14 (0.4 g, 0.9 mmol) and 1-(phenylmethyl)-4-piperidone (0.23 ml, 0.0013 mol) in acetic acid (2 drops) and $CH_3OH$ (4 ml) was stirred at RT for 1 hour. $NaBH_3CN$ (0.11 g, 0.0017 mol) was added. The mixture was stirred at RT for 3 days. Water was added. The mixture was filtered over celite. The celite was washed with EtOAc. The organic layer was separated, dried over $MgSO_4$, filtered off and the solvent was evaporated. The residue was purified by column chromatography over silica gel (eluent: $CH_2Cl_2/MeOH/NH_4OH$ 95/5/0.5; 15-40 µm). The desired fraction was collected and the solvent was evaporated. The residue was dissolved in 2-propanone (2 ml) and converted into the (E)-2-butenedioic acid salt (2 eq, 0.2 mmol). The precipitate was filtered off and dried (vacuum, 60° C.), yielding 0.065 g of compound 15; mp. 228° C.

Example B11

Preparation of Compound 16

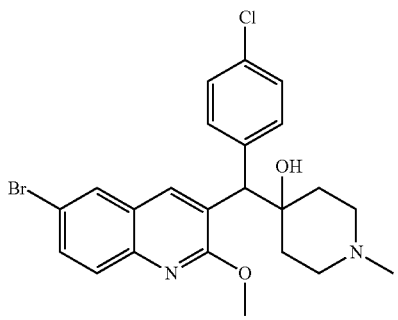

A mixture of compound 14 (0.4 g, 0.72 mmol) and formaldehyde, 37% in water (0.24 ml, 3.0 mmol) in CH$_2$Cl$_2$ (8 ml) was stirred for 15 minutes then sodium triacetoxyborohydride (0.38 g, 1.8 mmol) was added and the resulting mixture was stirred overnight at room temperature. The mixture was poured out into water and extracted with CH$_2$Cl$_2$. The organic layer was separated, washed with water, dried over MgSO$_4$, filtered and the solvent was evaporated to dryness. The residue was crystallized from diethyl ether. The precipitate was filtered off and dried, yielding: 0.052 g (15%) of compound 16; mp. 193° C.

Example B12

Preparation of Compound 17

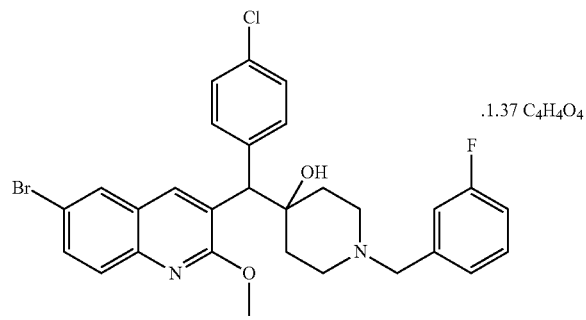 [SMILES: COc1nc2ccc(Br)cc2cc1C(c1ccc(Cl)cc1)C1(O)CCN(Cc2cccc(F)c2)CC1]

A mixture of compound 14 (0.26 mmol; 120 mg), 1-(bromomethyl)-3-fluorobenzene (0.39 mmol; 50 µl) and K$_2$CO$_3$ (0.39 mmol, 53.9 mg) in CH$_3$CN (5 ml) was stirred and refluxed for 18 hours. The mixture was cooled to RT and poured into water. EtOAc was added to the mixture and the organic layer was extracted, washed with water then brine, dried over MgSO$_4$, filtered and the solvent was evaporated under reduced pressure. Purification was carried out by column chromatography (Merck, 30 g, SiO$_2$ 15-40 µm, cyclohexane/EtOAc 75/25). The pure fraction was collected and the eluent was evaporated. The residue was dissolved in acetone (1 ml). Fumaric acid (1 eq) dissolved in acetone/ EtOH (50/50: 2 ml) was added to the mixture. The resulting precipitate was filtered off and dried, yielding 27 mg (15.15%) of compound 17.

Example B13 a) Preparation of Compounds 18 and 19

Compound 18
Compound 19: .1.16 C$_4$H$_4$O$_4$

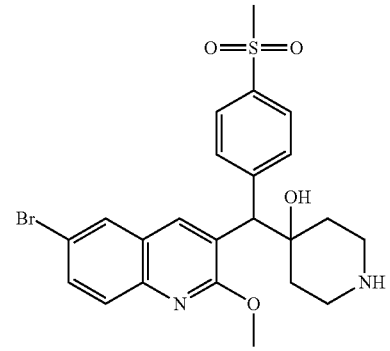

A solution of intermediate 6 (3.4 mmol, 2.059 g) in trifluoroacetic acid (5 ml) and DCM (25 ml) was stirred at RT for 45 minutes. The mixture was poured into 10% aqueous potassium carbonate solution and extracted with DCM. The organic layer was separated, washed with water, dried over MgSO$_4$, filtered and the solvent evaporated to dryness. The residue was purified by column chromatography over silica gel (B 6694, SiO$_2$ 14-40 µm, eluent: DCM/MeOH/ NH$_4$OHaq: 93/7/0.1 to 90/10/1. The pure fractions were collected and the solvent evaporated to dryness, yielding 0.3 g (17.457%) of compound 18. A sample of the base final product was crystallized as the fumarate salt compound 19.

b) Preparation of Compound 20

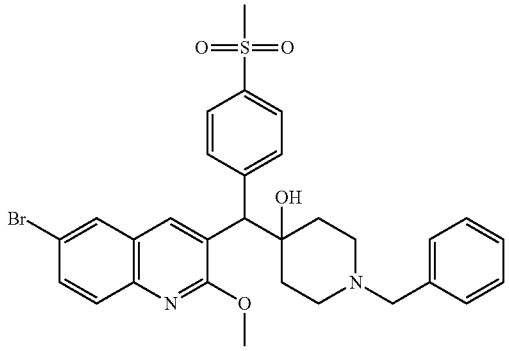 [SMILES: COc1nc2ccc(Br)cc2cc1C(c1ccc(S(C)(=O)=O)cc1)C1(O)CCN(Cc2ccccc2)CC1]

A mixture of compound 18 (0.3 g, 0.6 mmol), benzaldehyde (0.06 ml, 0.6 mmol) and sodium triacetoxyborohydride (0.189 g, 0.89 mmol) in 1,2 dichloroethane (5 ml) was stirred overnight. The solution was poured into water. The mixture was extracted with CH$_2$Cl$_2$, washed with water, dried (MgSO$_4$), filtered and the solvent was evaporated to dryness. The crude product was purified by column chromatography over silica gel (SiO$_2$ 3.5 µm, eluent: CH$_2$Cl$_2$/MeOH/NH$_4$OH aq: from 100/0/0 to 96/4/0.4). The pure fractions were col-

Example B14 a) Preparation of Compound 21

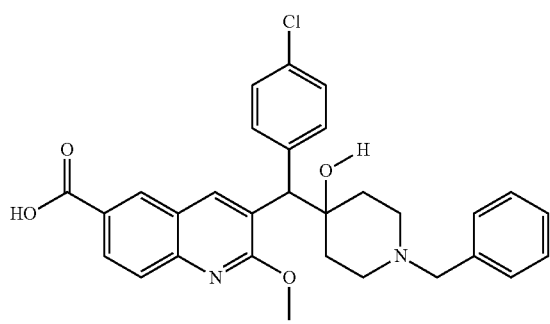 [SMILES: COc1nc2ccc(C(=O)O)cc2cc1C(c1ccc(Cl)cc1)C1(O)CCN(Cc2ccccc2)CC1]

n-BuLi 1.6M in hexane (5.7 ml; 9.06 mmol) was added dropwise at −70° C. under nitrogen flow to a solution of compound 6 (2 g; 3.62 mmol) in THF (20 ml). The mixture was stirred for 1.30 hours at −70° C. then DMF (2.24 ml; 29 mmol) was added. The resulting mixture was stirred for 2 hours at −70° C. then water was added. The mixture was extracted with EtOAc. The organic layer was washed with water then brine, dried over $MgSO_4$, filtered and evaporated to dryness. The residue was crystallized from diisopropylether and methanol. The residue was purified by column chromatography over silica gel (eluent: $CH_2Cl_2$/MeOH, 96/4, 15-40 μm, 450 g). The pure fractions were collected and the solvent was evaporated to dryness, yielding 0.712 g (39%) of compound 21.

b) Preparation of Compound 22

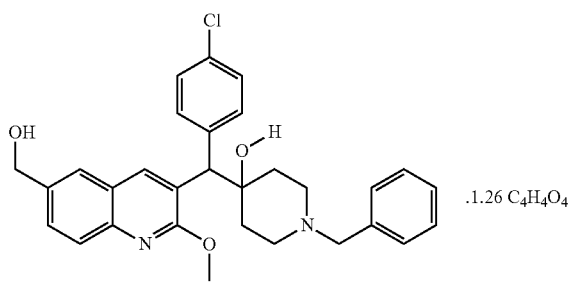 [SMILES: COc1nc2ccc(CO)cc2cc1C(c1ccc(Cl)cc1)C1(O)CCN(Cc2ccccc2)CC1]

.1.26 $C_4H_4O_4$

Sodium borohydride (9.1 mg, 0.24 mmol) was added at 0° C. to a solution of compound 21 (0.12 g, 0.24 mmol) in MeOH (2.5 ml) and THF (2.5 ml). The mixture was stirred for 2 hours at 0° C. then water was added and extracted with EtOAc. The organic layer was washed with water then brine, dried over $MgSO_4$, filtered and evaporated to dryness. Fumaric acid (0.049 g, 0.42 mmol) was added portionwise to a solution of pure product in acetone (3 ml) which was converted into the (E)-2-butenedioic acid salt. The mixture was stirred for 1 hour at room temperature. The precipitate was filtered off, washed with acetone, and dried under vacuum at 60° C., yielding 0.080 g (51.9%) of compound 22; mp. 196° C.

Example B15 a) Preparation of Compound 23

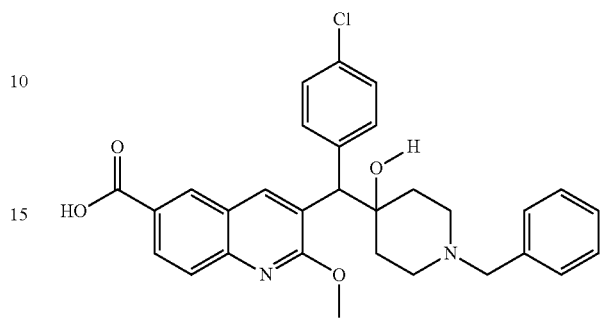

n-BuLi 1.6M in hexane (5.7 ml, 9.06 mmol) was added dropwise at −70° C. under nitrogen flow to a solution of compound 6 (2 g, 3.62 mmol) in THF (20 ml). The mixture was stirred for 2 hours at −70° C. $CO_2$ was bubbled through the RM at −78° C. Water was added carefully at −20° C. The organic layer was extracted with EtOAc, dried over $MgSO_4$, filtered and the solvent was concentrated. The residue was purified by column chromatography over silica gel (eluent: $CH_2Cl_2$/MeOH, 85/15, 15-40 μm, 300 g). The pure fractions were collected and the solvent was evaporated to dryness, yielding 0.600 g (32.6%). of compound 23.

b) Preparation of Compound 24

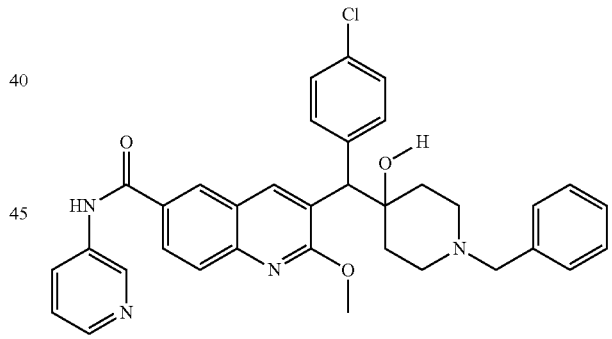

1-Hydroxy-1H-benzotriazole (58 mg, 0.43 mmol) and N'-(ethylcarbonimidoyl)-N,N-dimethyl-1,3-propanediamine monohydrochloride (82 mg, 0.43 mmol) were added to a solution of compound 23 (170 mg, 0.33 mmol) in $CH_2Cl_2$ (2 ml). The resulting mixture was stirred for 2 hours at RT, and then 3-pyridinamine (40 mg, 0.43 mmol) was added portionwise. The solution was stirred overnight at room temperature. Water was added and the organic layer was extracted with EtOAc, dried over $MgSO_4$, filtered and concentrated. The residue was purified by chromatography on a SiOH column (5 μm, 30×150 mm) from $CH_2Cl_2$/$CH_3OH$/$NH_4OH$ 98/2/0.2 to $CH_2Cl_2$/$CH_3OH$/$NH_4OH$ 92/8/0.8. The pure fractions were collected and evaporated. The residue was crystallized from DIPE, yielding 65 mg (33.33%) of compound 24.

Example B16

Preparation of Compound 25

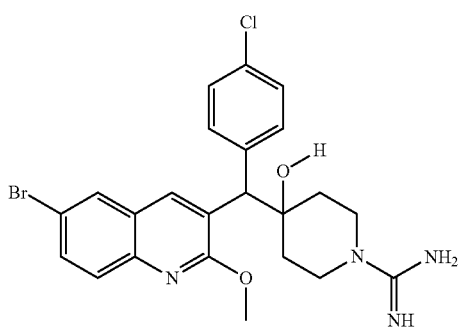 [SMILES: COc1nc2ccc(Br)cc2cc1C(c1ccc(Cl)cc1)C1(O)CCN(C(=N)N)CC1]

Compound 14 (0.365 g, 0.79 mmol) was added to a solution of N,N-diethylethanamine (0.55 ml, 3.95 mol) in acetonitrile (9 ml). Then 1H-pyrrazole-1-carboxamidine monohydrochloride (0.348 g, 2.37 mmol) was added and the resulting mixture was stirred 36 hours at 75° C. The resulting precipitate was filtered and washed with CH$_3$CN. The solid was washed 3 times with water and dried under vacuum at 60° C., yielding 0.276 g (69%) of compound 25.

Example B17

Preparation of Compound 26

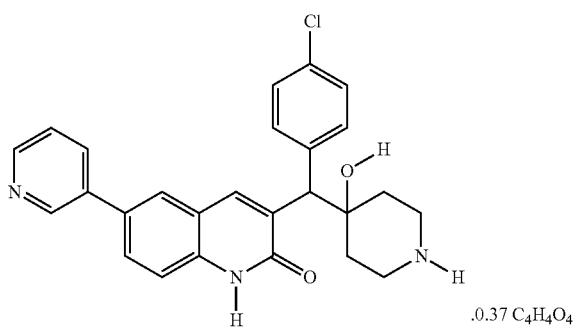 [SMILES: O=c1[nH]c2ccc(-c3cccnc3)cc2cc1C(c1ccc(Cl)cc1)C1(O)CCNCC1]

A mixture of intermediate 8 (0.9 mmol) in HCl 3N (5 ml) in THF (5 ml) was stirred at 70° C. overnight, then cooled to RT, poured out into ice water and stirred for 30 minutes. The precipitate was filtered, washed with water and dried at 60° C. in vacuo. The residue was crystallized from DIPE. The precipitate was filtered off and dried at 60° C. in vacuo. This fraction was dissolved in 2-propanone and converted into the (E)-2-butenedioic acid salt. The precipitate was filtered off, washed with 2-propanone and dried at 60° C. in vacuo, yielding 0.047 g (37%) of compound 26; mp. 250° C.

Example B18

Preparation of Compound 27

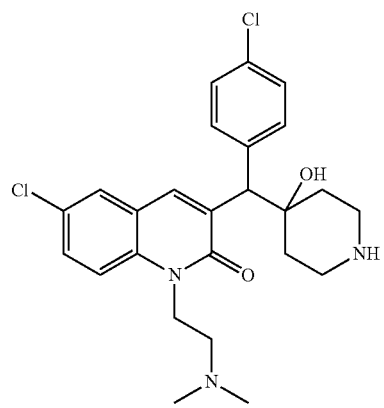 [SMILES: CN(C)CCn1c(=O)c(C(c2ccc(Cl)cc2)C2(O)CCNCC2)cc2cc(Cl)ccc21]

A solution of intermediate 18 (170 mg, 0.296 mmol) in HCl/2-propanol 5M (2 ml) was stirred at 0° C. for 5 hours at RT. 10% aqueous K$_2$CO$_3$ solution was added to the reaction mixture. The organic layer was separated, washed with water, dried over MgSO$_4$, filtered and the solvent was evaporated. Purification was carried out by flash chromatography over silica gel (15-40 nm, 52 mg, CH$_2$Cl$_2$/MeOH/NH$_4$OH 85/15/1). The pure fractions were collected and evaporated to dryness, yielding 25 mg (17.8%) of compound 27.

The following final compounds were prepared according to the methods described above. The compounds which are described in the Examples in Section B above are indicated with an asterisk against the relevant B example; the other compounds are prepared in an analogous manner to the relevant specified B example.

TABLE 1

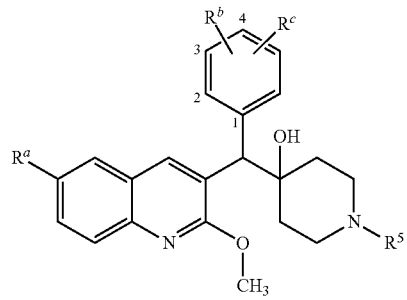

| Comp. No. | Ex. No. | R$^a$ | R$^b$ | R$^c$ | R$^5$ | Physical data |
|---|---|---|---|---|---|---|
| 28 | B1 | Br | H | H | CH$_3$ | |
| 29 | B1 | Br | H | H | phenylmethyl | |

TABLE 1-continued

| Comp. No. | Ex. No. | $R^a$ | $R^b$ | $R^c$ | $R^5$ | Physical data |
|---|---|---|---|---|---|---|
| 30 | B1 | Br | H | H | CH(CH$_3$)$_2$ | |
| 5 | B3* | Br | H | H | phenylethyl | |
| 6 | B4a* | Br | H | 4-Cl | phenylmethyl | |
| 35 | B4 | Br | H | 4-Cl | phenylmethyl | •1.12 C$_4$H$_4$O$_4$ |
| 36 | B4 | Br | H | 4-Cl | phenylmethyl | •1.15 C$_2$H$_2$O$_4$ |
| 38 | B3 | Br | H | H | (3-methylphenyl)methyl | |
| 39 | B3 | Br | H | 4-CH$_3$ | phenylmethyl | |
| 40 | B3 | Br | H | 4-CH$_3$O | phenylmethyl | |
| 42 | B3 | Br | H | H | 2-pyridinyl | |
| 7 | B4b* | Br | H | 4-Cl | phenylmethyl | R |
| 8 | B4b* | Br | H | 4-Cl | phenylmethyl | S |
| 14 | B10a* | Br | H | 4-Cl | H | |
| 45 | B10a | Br | H | 4-Cl | H | •1.14 C$_4$H$_4$O$_4$ |
| 46 | B1 | Br | H | 4-Cl | phenylethyl | |
| 47 | B1 | Br | H | 4-Cl | phenylethyl | •1.25 C$_4$H$_4$O$_4$ |
| 48 | B1 | Br | 3-CH$_3$ | 4-Cl | phenylmethyl | |
| 49 | B1 | Br | 3-CH$_3$ | 4-Cl | phenylmethyl | •1.14 C$_4$H$_4$O$_4$ |
| 53 | B1 | Br | 3-F | 4-Cl | phenylmethyl | •1.22 C$_4$H$_4$O$_4$ |
| 55 | B1 | Br | 3-CH$_3$ | 4-F | phenylmethyl | •1.15 C$_4$H$_4$O$_4$ |
| 58 | B1 | Br | H | 4-CN | phenylmethyl | •1.12 C$_4$H$_4$O$_4$ |
| 59 | B1 | Br | H | 3-Cl | phenylmethyl | |
| 60 | B1 | Br | H | 3-Cl | phenylmethyl | •1.12 C$_4$H$_4$O$_4$ |
| 61 | B3 | Br | H | 3-CH$_3$ | phenylmethyl | |
| 62 | B1 | Br | H | 4-Cl | (2-methylphenyl)methyl | |
| 63 | B1 | Br | H | 4-Cl | (2-methylphenyl)methyl | •1.24 C$_4$H$_4$O$_4$ |
| 65 | B1 | Br | 3-Cl | 4-Cl | phenylmethyl | •1.25 C$_4$H$_4$O$_4$ |
| 66 | B1 | Br | 3-CF$_3$ | 4-Cl | phenylmethyl | •1.42 C$_4$H$_4$O$_4$ |
| 67 | B1 | Br | H | 2-Cl | phenylmethyl | •1.25 C$_4$H$_4$O$_4$ |
| 72 | B1 | Br | H | 4-F | phenylmethyl | •1.2 C$_4$H$_4$O$_4$ |
| 83 | B1 | Br | H | 2-F | phenylmethyl | |
| 84 | B1 | Br | H | 3-F | phenylmethyl | |
| 15 | B10b* | Br | H | 4-Cl | 4-methyl-1-benzylpiperidinyl | •2.24 C$_4$H$_4$O$_4$ |
| 16 | B11* | Br | H | 4-Cl | CH$_3$ | |
| 95 | B5 | Br | H | 2-Cl | H | •1.24 C$_4$H$_4$O$_4$ |
| 98 | B5 | Br | H | 3-Cl | H | •1.38 C$_4$H$_4$O$_4$ |
| 18 | B13a* | Br | H | 4-S(=O)$_2$CH$_3$ | H | |
| 19 | B13a* | Br | H | 4-S(=O)$_2$CH$_3$ | H | •1.16 C$_4$H$_4$O$_4$ |
| 20 | B13b* | Br | H | 4-S(=O)$_2$CH$_3$ | phenylmethyl | |
| 17 | B12* | Br | H | 4-Cl | (3-fluorophenyl)methyl | •C$_4$H$_4$O$_4$ |
| 105 | B12 | Br | H | 4-Cl | (3-cyanophenyl)methyl | •C$_4$H$_4$O$_4$ |

TABLE 1-continued

| Comp Ex. No. | No. | R$^a$ | R$^b$ | R$^c$ | R$^5$ | Physical data |
|---|---|---|---|---|---|---|
| 25 | B16* | Br | H | 4-Cl | (amidino: C(=NH)NH$_2$) | |
| 12 | B8* | H | H | H | H | |
| 89 | B2b | phenyl | H | 4-Cl | phenylethyl | •1.21 C$_4$H$_4$O$_4$ |
| 91 | B1 | CH(CH$_3$)$_2$ | H | 4-Cl | phenylethyl | •1.65 C$_4$H$_4$O$_4$ |
| 92 | B5 | Br | H | 4-Cl | (2R)-2-benzyl-4-methylpiperidinyl | 2.42 C$_4$H$_4$O$_4$ |
| 93 | B5 | 3-pyridinyl | H | 4-Cl | H | •2.64 C$_4$H$_4$O$_4$ |
| 94 | B11 | 3-pyridinyl | H | 4-Cl | CH$_3$ | |
| 97 | B2a | 3-pyridinyl | H | 2-Cl | H | •1.61 C$_4$H$_4$O$_4$ |
| 99 | B5 | CH$_3$-S(=O)$_2$- | H | H | H | •0.89 C$_4$H$_4$O$_4$ |
| 21 | B14a* | H—C(=O)— | H | 4-Cl | phenylmethyl | |
| 23 | B15a* | HO—C(=O)— | H | 4-Cl | phenylmethyl | |
| 9 | B5* | Br | H | 4-CH$_3$S | H | C$_4$H$_4$O$_4$ |
| 82 | B1 | morpholinyl | H | H | phenylmethyl | C$_4$H$_4$O$_4$ |

TABLE 2

| Comp Ex. No. | No. | R$^a$ | R$^b$ | R$^c$ | X | Physical data |
|---|---|---|---|---|---|---|
| 32 | B3 | H | H | H | S | |
| 41 | B3 | 6-CH$_3$ | H | H | S | |

TABLE 2-continued

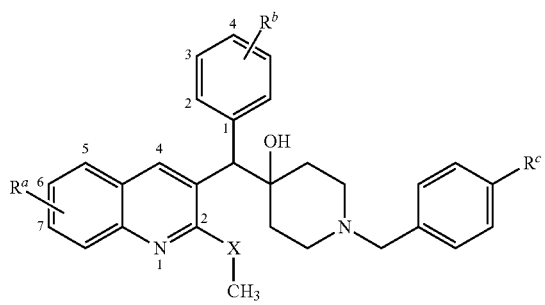

| Comp No. | Ex. No. | $R^a$ | $R^b$ | $R^c$ | X | Physical data |
|---|---|---|---|---|---|---|
| 4 | B2c* | 6-phenyl | H | H | O | |
| 31 | B2b | 6-(4-pyridinyl) | H | H | O | |
| 33 | B3 | 6-Cl | H | H | O | |
| 34 | B3 | 6-CH$_3$O | H | H | O | |
| 37 | B2b | 6-[2-furanyl] | H | H | O | |
| 43 | B3 | 7-Br | H | H | O | |
| 44 | B3 | 5-Br | H | H | O | |
| 50 | B2a | 6-[3-pyridinyl] | 4-Cl | H | O | •1.24 C$_4$H$_4$O$_4$ |
| 51 | B2b | 6-phenyl | 4-Cl | H | O | •1.20 C$_4$H$_4$O$_4$ |
| 52 | B1 | H | 4-Cl | H | O | •1.31 C$_4$H$_4$O$_4$ |
| 64 | B2b | 6-[2-furanyl] | 4-Cl | H | O | •1.23 C$_4$H$_4$O$_4$ |
| 69 | B2b | 6-phenyl | 4-Cl | CH$_3$ | O | •1.29 C$_4$H$_4$O$_4$ |
| 70 | B2b | 6-[2-furanyl] | 4-Cl | CH$_3$ | O | •1.34 C$_4$H$_4$O$_4$ |
| 71 | B2a | 6-[3-pyridinyl] | 4-Cl | CH$_3$ | O | •1.21 C$_4$H$_4$O$_4$ |
| 11 | B7* | 6-CH=CH$_2$ | 4-Cl | H | O | •1.13 C$_4$H$_4$O$_4$ |
| 73 | B7 | 6-CH=CH$_2$ | 4-Cl | CH$_3$ | O | •1.18 C$_4$H$_4$O$_4$ |
| 76 | B9 | 6-CN | 4-Cl | CH$_3$ | O | |
| 13 | B9* | 6-CN | 4-Cl | H | O | •1.24 C$_4$H$_4$O$_4$ |
| 81 | B1 | 6-CH$_3$O | 4-Cl | H | O | •1.13 C$_4$H$_4$O$_4$ |
| 86 | B1 | 6-CF$_3$ | 4-Cl | H | O | •1.34 C$_4$H$_4$O$_4$ |
| 88 | B1 | 6-Cl | 4-Br | H | O | |
| 90 | B1 | 6-[CH(CH$_3$)$_2$] | 4-Cl | H | O | •1.21 C$_4$H$_4$O$_4$ |
| 110 | B12 | 6-[CH$_3$-S(=O)$_2$-] | H | H | O | •0.7 C$_4$H$_4$O$_4$ |
| 106 | B5 | 6-[HN-piperidinyl-4-OH, 4-methyl] | 4-Cl | H | | |
| 22 | B14b* | 6-(hydroxymethyl) | 4-Cl | H | O | •1.26 C$_4$H$_4$O$_4$ |
| 107 | B15b | 6-(aminocarbonyl) | 4-Cl | H | O | |
| 24 | B15b* | 6-[pyridin-3-yl-NH-C(=O)-] | 4-Cl | H | O | |
| 108 | B15b | 6-[(CH$_3$)$_2$N—C(=O)—] | 4-Cl | H | O | |

TABLE 3

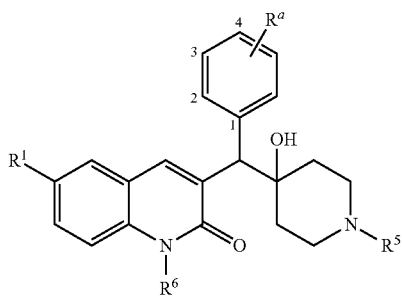

| Comp No. | Ex. No. | R² | R⁴ | p | Physical data |
|---|---|---|---|---|---|
| 54 | B1 | CH₃O | 2-benzofuranyl | 1 | •1.13 C4H4O4 |
| 56 | B1 | CH₃O | 2-naphtalenyl | 1 | •1.2 C₄H₄O₄ |
| 57 | B1 | CH₃O | 3-pyridinyl | 1 | •1.07 C₄H₄O₄ |
| 68 | B1 | CH₃O | 2-furanyl | 1 | •1.18 C₄H₄O₄ |
| 85 | B1 | CH₃O | 1,3-benzodioxol-2-yl | 1 | •1.1 C₄H₄O₄ |
| 75 | B1 | N(CH₃)₂ | 4-chlorophenyl | 1 | •1.13 C₄H₄O₄ |
| 77 | B1 | 4-morpholinyl | 4-chlorophenyl | 1 | •1.22 C₄H₄O₄ |
| 1 | B1* | 4-morpholinyl | 4-chlorophenyl | 2 | •2.03 C₄H₄O₄ |
| 87 | B1 | 1-piperidinyl | 4-chlorophenyl | 1 | •1.36 C₄H₄O₄ |
| 109 | B1 | 1-piperidinyl | 4-chlorophenyl | 2 | •1.25 C₄H₄O₄ |

TABLE 5

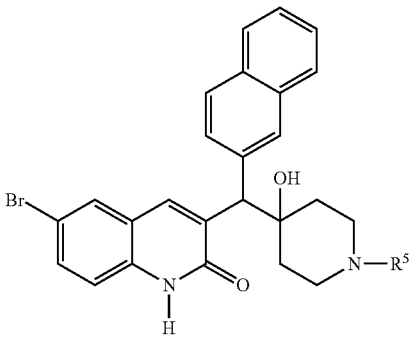

| Comp No. | Ex. No. | R⁵ | Physical data |
|---|---|---|---|
| 80 | B6 | phenylmethyl | |

TABLE 4

| Comp No. | Ex. No. | R¹ | Rᵃ | R⁶ | R⁵ | Physical data |
|---|---|---|---|---|---|---|
| 74 | B6 | Br | 4-Cl | H | phenylethyl | |
| 78 | B6 | 3-pyridinyl | 4-Cl | H | phenylmethyl | |
| 79 | B6 | Br | 4-Cl | H | H | |
| 10 | B6* | Br | 4-Cl | H | phenylmethyl | |
| 26 | B17* | 3-pyridinyl | 4-Cl | H | H | •0.37 C₄H₄O₄ |
| 96 | B1 | Br | 4-Cl | CH₃ | phenylmethyl | |
| 27 | B18 | Cl | Cl | (CH₃)₂—N—(CH₂)₂— | H | |
| 100 | B6 | CH₃-S(=O)(=O)- | H | H | H | •HCl |
| 2 | B2a* | Br | 4-Cl | C₂H₅ | phenylmethyl | |
| 3 | B2b* | 3-pyridinyl | 4-Cl | C₂H₅ | phenylmethyl | |
| 101 | B6 | Br | 3-Cl | H | H | •0.87 HCl |
| 102 | B5 | Br | 4-Cl | C₂H₅ | H | •0.9 C₄H₄O₄ |
| 103 | B6 | Br | 4-CN | H | H | •HCl |
| 104 | B5 | 3-pyridinyl | 4-Cl | C₂H₃ | H | •1.75 C2HF3O2 |

C. Analytical Methods

General Procedure A

The HPLC measurement was performed using an Alliance HT 2795 (Waters) system comprising a quaternary pump with degasser, an autosampler, a diode-array detector (DAD) and a column as specified in the respective methods below, the column is hold at a temperature of 30° C. Flow from the column was split to a MS spectrometer. The MS detector was configured with an electrospray ionization source. The capillary needle voltage was 3 kV and the source temperature was maintained at 100° C. on the LCT (Time of Flight Zspray™ mass spectrometer from Waters—for methods 1, 2 and 3 and 3.15 kV at 110° C. on the ZQ™ (simple quadrupole Zspray™ mass spectrometer from Waters—for methods 4 and 5. Nitrogen was used as the nebulizer gas. Data acquisition was performed with a Waters-Micromass MassLynx-Openlynx data system.

General procedure B

The LC measurement was performed using a UPLC (Ultra Performance Liquid Chromatography) Acquity (Waters) system comprising a binary pump with degasser, an autosampler, a diode-array detector (DAD) and a column as specified in the respective methods below, the column is hold at a temperature of 40° C. Flow from the column was brought to a MS detector. The MS detector was configured with an electrospray ionization source. The capillary needle voltage was 3 kV and the source temperature was maintained at 130° C. on the Quattro (triple quadrupole mass spectrometer from Waters). Nitrogen was used as the nebulizer gas. Data acquisition was performed with a Waters-Micromass MassLynx-Openlynx data system.

Method 1

In addition to the general procedure A: Reversed phase HPLC was carried out on a Kromasil C18 column (5 µm, 4.6×150 mm) with a flow rate of 1.0 ml/min. Three mobile phases (mobile phase A: 100% 7 mM ammonium acetate; mobile phase B: 100% acetonitrile; mobile phase C: 0.2% formic acid+99.8% ultra-pure Water) were employed to run a gradient condition from 30% A, 40% B and 30% C (hold for 1 minute) to 100% B in 4 minutes, 100% B for 5 minutes and reequilibrated with initial conditions for 3 minutes. An injection volume of 5 µl was used. Cone voltage was 20 V for positive ionization mode. Mass spectra were acquired by scanning from 100 to 900 in 0.8 seconds using an interscan delay of 0.08 seconds.

Method 2

In addition to the general procedure A: Reversed phase HPLC was carried out on a Kromasil C18 column (5 µm, 4.6×150 mm) with a flow rate of 1.0 ml/min. Three mobile phases (mobile phase A: 100% 7 mM ammonium acetate; mobile phase B: 100% acetonitrile; mobile phase C: 0.2% formic acid+99.8% ultra-pure Water) were employed to run a gradient condition from 30% A, 40% B and 30% C (hold for 1 minute) to 100% B in 4 minutes, 100% B for 5 minutes and reequilibrated with initial conditions for 3 minutes. An injection volume of 5 µl was used. Cone voltage was 20 V for positive and negative ionization mode. Mass spectra were acquired by scanning from 100 to 900 in 0.8 seconds using an interscan delay of 0.08 seconds.

Method 3

In addition to the general procedure A: Reversed phase HPLC was carried out on a Xterra-MS C18 column (5 µm, 4.6×150 mm) with a flow rate of 1.0 ml/min. Two mobile phases (mobile phase A: 100% 7 mM ammonium acetate; mobile phase B: 100% acetonitrile; were employed to run a gradient condition from 85% A, 15% B (hold for 3 minutes) to 20% A, 80% B in 5 minutes, hold at 20% A and 80% B for 6 minutes and reequilibrated with initial conditions for 3 minutes. An injection volume of 20 µl was used. Cone voltage was 20 V for positive ionization mode and 20 V for negative ionization mode. Mass spectra were acquired by scanning from 100 to 900 in 0.8 seconds using an interscan delay of 0.08 seconds.

Method 4

In addition to the general procedure A: Reversed phase HPLC was carried out on a Sunfire C18 column (3.5 µm, 4.6×100 mm) with an initial flow rate of 0.8 ml/min. Two mobile phases (mobile phase A: 35% 6.5 mM ammonium acetate+30% acetonitrile+35% formic acid (2 ml/1); mobile phase B: 100% acetonitrile) were employed to run a gradient condition from 100% A (hold for 1 minute) to 100% B in 4 minutes, hold at 100% B at a flow rate of 1.2 ml/min for 4 minutes and reequilibrated with initial conditions for 3 minutes. An injection volume of 10 µl was used. Cone voltage was 20 V for positive and negative ionization mode. Mass spectra were acquired by scanning from 100 to 1000 in 0.4 seconds using an interscan delay of 0.3 seconds.

Method 5

In addition to the general procedure A: Reversed phase HPLC was carried out on a Sunfire C18 column (3.5 nm, 4.6×100 mm) with an initial flow rate of 0.8 ml/min. Two mobile phases (mobile phase A: 35% 6.5 mM ammonium acetate+30% acetonitrile+35% formic acid (2 ml/l); mobile phase B: 100% acetonitrile) were employed to run a gradient condition from 100% A (hold for 1 minute) to 100% B in 4 minutes, hold at 100% B at a flow rate of 1.2 ml/min for 4 minutes and reequilibrated with initial conditions for 3 minutes. An injection volume of 10 µl was used. Positive ionization mode was used with four different cone voltages (20, 40, 50, 55 V). Mass spectra were acquired by scanning from 100 to 1000 in 0.4 seconds using an interscan delay of 0.1 seconds.

Method 6

In addition to the general procedure B: Reversed phase UPLC was carried out on a Waters Acquity bridged ethylsiloxane/silica hybrid (BEH) C18 column (1.7 µm, 2.1×100 mm) with a flow rate of 0.4 ml/min. Two mobile phases (mobile phase A: 100% 7 mM ammonium acetate; mobile phase B: 100% acetonitrile) were employed to run a gradient condition from 80% A and 20% B (hold for 0.5 minutes) to 10% A and 90% B in 3.5 minutes, hold for 2 minutes and reequilibrated with initial conditions for 2 minutes. An injection volume of 2 µl was used. Cone voltage was 20 V for positive and negative ionization mode. Mass spectra were acquired by scanning from 100 to 1000 in 0.2 seconds using an interscan delay of 0.1 seconds.

Method 7

In addition to the general procedure B: Reversed phase UPLC was carried out on a Waters Acquity bridged ethylsiloxane/silica hybrid (BEH) C18 column (1.7 µm, 2.1×100 mm) with a flow rate of 0.4 ml/min. Two mobile phases (mobile phase A: 100% 7 mM ammonium acetate; mobile phase B: 100% acetonitrile) were employed to run a gradient condition from 80% A and 20% B (hold for 0.5 minutes) to 10% A and 90% B in 3.5 minutes, hold for 2 minutes and reequilibrated with initial conditions for 2 minutes. An injection volume of 2 µl was used. Cone voltages were 20, 30, 45, 60 V for positive ionization mode. Mass spectra were acquired by scanning from 100 to 1000 in 0.2 seconds using an interscan delay of 0.1 seconds.

Method 8

In addition to the general procedure B: Reversed phase UPLC was carried out on a Waters Acquity BEH (bridged ethylsiloxane/silica hybrid) C18 column (1.7 μm, 2.1×100 mm) with a flow rate of 0.35 ml/min. Two mobile phases (mobile phase A: 95% 7 mM ammonium acetate/5% acetonitrile; mobile phase B: 100% acetonitrile) were employed to run a gradient condition from 90% A and 10% B (hold for 0.5 minutes) to 8% A and 92% B in 3.5 minutes, hold for 2 min and back to the initial conditions in 0.5 min, hold for 1.5 minutes. An injection volume of 2 μl was used. Cone voltage was 20 V for positive and negative ionization mode. Mass spectra were acquired by scanning from 100 to 1000 in 0.2 seconds using an interscan delay of 0.1 seconds.

Method 9

In addition to the general procedure B: Reversed phase UPLC was carried out on a Thermo Hypersil Gold C18 column (1.9 μm, 2.1×100 mm) with a flow rate of 0.40 ml/min. Two mobile phases (mobile phase A: 95% 7 mM ammonium acetate/5% acetonitrile; mobile phase B: 100% acetonitrile) were employed to run a gradient condition from 72% A and 28% B (hold for 0.5 minutes) to 8% A and 92% B in 3.5 minutes, hold for 2 min and back to the initial conditions in 0.5 min, hold for 1.5 minutes. An injection volume of 2 μl was used. Cone voltage was 20 V for positive and negative ionization mode. Mass spectra were acquired by scanning from 100 to 1000 in 0.2 seconds using an interscan delay of 0.1 seconds.

Method 10

In addition to the general procedure B: Reversed phase UPLC was carried out on a Waters HSS (High Strength Silica) C18 column (1.8 μm, 2.1×100 mm) with a flow rate of 0.40 ml/min. Two mobile phases (mobile phase A: 95% 7 mM ammonium acetate/5% acetonitrile; mobile phase B: 100% acetonitrile) were employed to run a gradient condition from 72% A and 28% B (hold for 0.5 minutes) to 8% A and 92% B in 3.5 minutes, hold for 2 min and back to the initial conditions in 0.5 min, hold for 1.5 minutes. An injection volume of 2 μl was used. Cone voltage was 20 V for positive and negative ionization mode. Mass spectra were acquired by scanning from 100 to 1000 in 0.2 seconds using an interscan delay of 0.1 seconds.

C2. Optical Rotation

The optical rotation was measured using a polarimeter. $[\alpha]_D^{20}$ indicates the optical rotation measured with light at the wavelength of the D-line of sodium (589 nm) at a temperature of 20° C. The cell pathlength is 1 dm. After $[\alpha]_D^{20}$ value the temperature, concentration and solvent of the solution which was used to measure the optical rotation are indicated.

C3. Melting Points

For a number of compounds, melting points were obtained with a Kofler hot bench, consisting of a heated plate with linear temperature gradient, a sliding pointer and a temperature scale in degrees Celsius.

TABLE 6

| Co. | MP (° C.) (Kofler) | Rt | (MH+) | LCMS Method |
|---|---|---|---|---|
| 28 | 94° C. | 4.60 | 441 | 1 |
| 29 | 72° C. | 5.29 | 517 | 1 |
| 30 |  | 4.81 | 469 | 1 |
| 4 |  | 6.04 | 515 | 1 |
| 31 | 220° C. | 3.13 | 517 | 1 |
| 5 |  | 5.47 | 531 | 2 |
| 32 |  | 4.97 | 455 | 2 |
| 33 |  | 5.2 | 473 | 2 |
| 34 |  | 4.7 | 469 | 2 |
| 6 |  | 5.02 | 553 | 4 |
| 35 |  | 5.02 | 553 | 4 |
| 36 |  | 5.02 | 553 | 4 |
| 37 |  | 5.64 | 505 | 1 |
| 38 |  | 5.47 | 531 | 2 |
| 39 |  | 5.6 | 531 | 2 |
| 40 |  | 5.23 | 547 | 2 |
| 41 |  | 5.27 | 469 | 2 |
| 42 |  | 4.94 | 518 | 2 |
| 43 |  | 5.37 | 517 | 2 |
| 44 |  | 5.2 | 517 | 2 |
| 7 |  | 4.98 | 553 | 4 |
| 8 |  | 4.98 | 553 | 4 |
| 14 | 210° C. | 4.97 | 463 | 2 |
| 45 | 210° C. | 4.97 | 463 | 2 |
| 46 | 217° C. | 5.13 | 567 | 4 |
| 47 | 213° C. | 5.13 | 567 | 4 |
| 48 | 167° C. | 5.18 | 567 | 4 |
| 49 | 167° C. | 5.18 | 567 | 4 |
| 50 | 196° C. | 4.28 | 550 | 4 |
| 51 | 209° C. | 5.33 | 549 | 4 |
| 52 | 214° C. | 5.04 | 473 | 2 |
| 53 | 182° C. | 5.02 | 571 | 4 |
| 54 | 158° C. | 5.64 | 557 | 2 |
| 55 | 161° C. | 5.61 | 549 | 2 |
| 56 | 159° C. | 5.83 | 567 | 2 |
| 57 | 155° C. | 3.54 | 518 | 2 |
| 58 | 220° C. | 4.73 | 544 | 4 |
| 59 | 159° C. | 5.74 | 553 | 2 |
| 60 | 159° C. ( | 5.74 | 553 | 2 |
| 61 |  | 5.1 | 533 | 6 |
| 62 |  | 6.02 | 567 | 7 |
| 63 | 212° C. | 5.91 | 567 | 2 |
| 64 | 203° C. | 5.71 | 539 | 2 |
| 65 | 190° C. | 6.13 | 587 | 2 |
| 66 | 217° C. | 6.17 | 621 | 2 |
| 67 | 184° C. | 4.88 | 553 | 4 |
| 68 | 151° C. | 4.62 | 509 | 4 |
| 69 | 215° C. | 5.33 | 563 | 4 |
| 70 | 220° C. | 5.15 | 553 | 4 |
| 71 | 218° C. | 4.45 | 564 | 4 |
| 11 | 195° C. | 4.58 | 501 | 4 |
| 72 | 184° C. | 4.83 | 537 | 4 |
| 73 | 198° C. | 4.73 | 515 | 4 |
| 74 | 217° C. | 4.53 | 553 | 4 |
| 75 | 173° C. | 5.02 | 566 | 4 |
| 12 | 119° C. | 3.29 | 349 | 2 |
| 76 |  | 4.77 | 512 | 5 |
| 77 | 170° C. | 5 | 608 | 5 |
| 13 | 199° C. | 4.63 | 498 | 5 |
| 78 | 207° C. | 8.83 | 536 | 3 |
| 79 | 200° C. | 8.06 | 449 | 3 |
| 10 | 244° C. | 9.9 | 539 | 3 |
| 80 | 249° C. | 10.06 | 553 | 3 |
| 81 | 203° C. | 4.8 | 503 | 5 |
| 82 | 217° C. | 4.33 | 524 | 5 |
| 83 |  | 4.92 | 537 | 5 |
| 84 |  | 4.92 | 537 | 5 |
| 85 | 163° C. | 4.83 | 563 | 5 |
| 86 | 182° C. | 5.32 | 541 | 4 |
| 1 | 158° C. | 5.23 | 622 | 4 |
| 87 | 181° C. | 6.74 | 606 | 6 |
| 88 |  | 5.08 | 553 | 6 |
| 89 | 202° C. | 5.1 | 563 | 6 |
| 90 | 185° C. | 5.47 | 515 | 6 |
| 91 | 207° C. | 5.14 | 529 | 6 |
| 15 | 218° C. | 4.2 | 636 | 9 |
| 92 | 174° C. | 4.07 | 634 | 9 |
| 16 | 193° C. | 4.01 | 477 | 9 |
| 26 | >250° C. | 1.98 | 446 | 9 |
| 93 | 212° C. | 2.86 | 460 | 9 |
| 94 | 226° C. | 3.17 | 474 | 9 |
| 95 | 248° C. | 3.51 | 463 | 9 |
| 96 | 233° C. | 4 | 553 | 9 |
| 97 | 241° C. | 2.71 | 460 | 9 |
| 98 | >250° C. | 3.72 | 463 | 9 |
| 9 | 204° C. | 3.75 | 475 | 9 |
| 99 | >260° C. | 1.96 | 427 | 9 |
| 19 |  | 2.57 | 507 | 9 |
| 100 | >260° C. | 1.09 | 413 | 9 |

TABLE 6-continued

| Co. | MP (° C.) (Kofler) | Rt | (MH+) | LCMS Method |
|---|---|---|---|---|
| 2 | 212° C. | 4.34 | 567 | 9 |
| 3 | 172° C. | 3.7 | 564 | 9 |
| 101 | >250° C. | 2.65 | 449 | 9 |
| 102 | 232° C. | 3.46 | 477 | 9 |
| 103 | >260° C. | 2.05 | 440 | 9 |
| 104 | >250° C. | 2.8 | 474 | 9 |
| 20 |  | 3.97 | 597 | 10 |
| 17 | 220° C. | 5.72 | 571 | 8 |
| 105 | 208° C. | 5.12 | 578 | 10 |
| 106 | 137° C. | 3.66 | 287 | 8 |
| 22 | 196° C. | 4.09 | 503 | 8 |
| 107 | 137° C. | 3.85 | 516 | 8 |
| 24 | 146° C. | 4.28 | 593 | 8 |
| 108 |  | 4.23 | 544 | 8 |
| 25 | >250° C. | 4.1 | 505 | 8 |

D. Pharmacological Examples

D.1. In-Vitro Method for Testing Compounds for Anti-Bacterial Activity Against Strain *M. Smegmatis* ATCC607.

Flat-bottom, sterile 96-well plastic microtiter plates were filled with 180 µl of sterile deionized water, supplemented with 0.25% BSA. Subsequently, stock solutions (7.8× final test concentration) of compounds were added in 45 µl volumes to a series of duplicate wells in column 2 so as to allow evaluation of their effects on bacterial growth. Serial five-fold dilutions (45 µl in 180 µl) were made directly in the microtiter plates from column 2 to 11 using a customised robot system (Zymark Corp., Hopkinton, Mass.). Pipette tips were changed after every 3 dilutions to minimize pipetting errors with high hydrophobic compounds. Untreated control samples with (column 1) and without (column 12) inoculum were included in each microtiter plate. Approximately 250 CFU per well of bacteria inoculum, in a volume of 100 in 2.8× Mueller-Hinton broth medium, was added to the rows A to H, except column 12. The same volume of broth medium without inoculum was added to column 12 in row A to H. The cultures were incubated at 37° C. for 48 hours in a humidified 5% $CO_2$ atmosphere (incubator with open air valve and continuous ventilation). At the end of incubation, two days after inoculation, the bacterial growth was quantitated fluorometrically. Therefore Alamar Blue (10×) was added to all wells in a volume of 20 and plates were incubated for another 2 hours at 50° C.

The fluorescence was read in a computer-controlled fluorometer (Cytofluor, Biosearch) at an excitation wavelength of 530 nm and an emission wavelength of 590 nm (gain 30). The percentage growth inhibition achieved by the compounds was calculated according to standard methods and expressed as $IC_{90}$ (µ/ml) which defines the 90% inhibitory concentration for bacterial growth. The results are shown in Table 7.

D.2. In-Vitro Method for Testing Compounds for Anti-Bacterial Activity Against a Non-Mycobacterial Strain Preparation of Bacterial Suspensions for Susceptibility Testing:

The bacteria used in this study were grown overnight in flasks containing 100 ml Mueller-Hinton Broth (Becton Dickinson—cat. no. 275730) in sterile de-ionized water, with shaking, at 37° C. Stocks (0.5 ml/tube) were stored at −70° C. until use. Bacteria titrations were performed in microtiter plates to detect the $TCID_{50}$, in which $TCID_{50}$ represents the dilution that gives rise to bacterial growth in 50% of inoculated cultures. In general, an inoculum level of approximately 100 $TCID_{50}$ was used for susceptibility testing.

Anti Bacterial Susceptibility Testing: $IC_{90}$ Determination Microtitre Plate Assay Flat-bottom, sterile 96-well plastic microtiter plates were filled with 180 µl of sterile deionized water, supplemented with 0.25% BSA. Subsequently, stock solutions (7.8× final test concentration) of compounds were added in 45 µl volumes in column 2 Serial five-fold dilutions (45 µl in 180 µl) were made directly in the microtiter plates from column 2 to reach column 11. Untreated control samples with (column 1) and without (column 12) inoculum were included in each microtiter plate. Depending on the bacteria type, approximately 10 to 60 CFU per well of bacteria inoculum (100 TCID50), in a volume of 100 µl in 2.8× Mueller-Hinton broth medium, was added to the rows A to H, except column 12. The same volume of broth medium without inoculum was added to column 12 in row A to H. The cultures were incubated at 37° C. for 24 hours under a normal atmosphere (incubator with open air valve and continuous ventilation). At the end of incubation, one day after inoculation, the bacterial growth was quantitated fluorometrically. Therefore resazurin (0.6 mg/ml) was added in a volume of 20 µl to all wells 3 hours after inoculation, and the plates were re-incubated overnight. A change in colour from blue to pink indicated the growth of bacteria. The fluorescence was read in a computer-controlled fluorometer (Cytofluor Biosearch) at an excitation wavelength of 530 nm and an emission wavelength of 590 nm. The % growth inhibition achieved by the compounds was calculated according to standard methods. The $IC_{90}$ (expressed in µg/ml) was defined as the 90% inhibitory concentration for bacterial growth. The results are shown in Table 7 for an assay using a *Staphylococcus aureus* strain.

Agar Dilution Method.

$MIC_{99}$ values (the minimal concentration for obtaining 99% inhibition of bacterial growth) can be determined by performing the standard Agar dilution method according to NCCLS standards* wherein the media used includes Mueller-Hinton agar.

* Clinical laboratory standard institute. 2005. Methods for dilution Antimicrobial susceptibility tests for bacteria that grows Aerobically: approved standard—sixth edition Time Kill Assays Bactericidal or bacteriostatic activity of the compounds may be determined in a time kill assay using the broth microdilution method *. In a time kill assay on *Staphylococcus aureus*, the starting inoculum of *S. aurues* is $10^6$ CFU/ml in Muller Hinton broth. The antibacterial compounds are used at the concentration of 0.1 to 10 times the MIC (i.e. $IC_{90}$ as determined in microtitre plate assay). Wells receiving no antibacterial agent constitute the culture growth control. The plates containing the microorganism and the test compounds are incubated at 37° C. After 0, 3, 6, and 24 hrs of incubation samples are removed for determination of viable counts by serial dilution ($10^{-1}$ to $10^{-6}$) in sterile PBS and plating (200 µl) on Mueller Hinton agar. The plates are incubated at 37° C. for 24 hrs and the number of colonies are determined Killing curves can be constructed by plotting the $\log_{10}$ CFU per ml versus time. A bactericidal effect is commonly defined as 3-$\log_{10}$ decrease in number of CFU per ml as compared to untreated inoculum. The potential carryover effect of the drugs is removed by serial dilutions and counting the colonies at highest dilution used for plating.

* Zurenko, G. E. et al. In vitro activities of U-100592 and U-100766, novel oxazolidinone antibacterial agents. *Antimicrob. Agents Chemother.* 40, 839-845 (1996).

Determination of Cellular ATP Levels

In order to analyse the change in the total cellular ATP concentration (using ATP bioluminescence Kit, Roche), assays are carried out by growing a culture of *S. aureus* (ATCC29213) stock in 100 ml Mueller Hinton flasks and incubate in a shaker-incubator for 24 hrs at 37° C. (300 rpm). Measure $OD_{405}$ and calculate the CFU/ml. Dilute the cultures to $1\times10^6$ CFU/ml (final concentration for ATP measurement: $1\times10^5$ CFU/100 µl per well) and add test compound at 0.1 to 10 times the MIC (i.e. $IC_{90}$ as determined in microtitre plate assay). Incubate these tubes for 0, 30 and 60 minutes at 300 rpm and 37° C. Use 0.6 ml bacterial suspension from the snap-cap tubes and add to a new 2 ml eppendorf tubes. Add 0.6 ml cell lysis reagent (Roche kit), vortex at max speed and incubate for 5 minutes at room temperature. Cool on ice. Let the luminometer warm up to 30° C. (Luminoskan Ascent Labsystems with injector). Fill one column (=6 wells) with 100 µl of the same sample. Add 100 µl Luciferase reagent to each well by using the injector system. Measure the luminescence for 1 sec.

TABLE 7

$IC_{90}$ values (µg/ml).

| Comp No. | STA B29213 | MSM 607 |
|---|---|---|
| 28 | >27.85 | 11.09 |
| 29 | 32.65 | |
| 30 | >29.62 | |
| 4 | >32.47 | |
| 31 | >32.54 | |
| 5 | 8.42 | |
| 32 | >28.69 | |
| 33 | 14.96 | |
| 34 | >29.57 | |
| 6 | >13.86 | >13.86 |
| 35 | >43.03 | |
| 36 | 32.85 | |
| 37 | >31.84 | |
| 38 | >33.54 | |
| 39 | 33.54 | |
| 40 | 13.75 | |
| 41 | >29.57 | |
| 42 | 32.71 | |
| 43 | 20.60 | |
| 44 | >32.65 | |
| 7 | >34.82 | |
| 8 | >34.82 | |
| 14 | 11.60 | |
| 45 | 19.23 | |
| 46 | >35.71 | |
| 47 | 17.86 | 4.49 |
| 48 | >35.71 | |
| 49 | >44.06 | |
| 50 | >43.79 | |
| 51 | >42.92 | |
| 52 | 19.77 | |
| 53 | >44.89 | |
| 54 | >43.45 | |
| 55 | >43.09 | |
| 56 | >44.60 | |
| 57 | 20.32 | |
| 58 | 8.47 | |
| 59 | 17.45 | |
| 60 | >43.03 | |
| 61 | 15.85 | 3.16 |
| 62 | 15.85 | 3.16 |
| 63 | >44.79 | |
| 64 | >43.02 | |
| 65 | >46.15 | |
| 66 | >49.51 | |
| 67 | >43.98 | |
| 68 | >40.66 | |
| 69 | >44.98 | |
| 70 | >44.71 | |
| 71 | >44.46 | |

TABLE 7-continued $IC_{90}$ values (µg/ml).

| Comp No. | STA B29213 | MSM 607 |
|---|---|---|
| 11 | >39.76 | |
| 72 | 33.82 | |
| 73 | >41.02 | |
| 74 | 6.95 | |
| 75 | 34.89 | |
| 12 | >21.99 | |
| 76 | >21.99 | |
| 77 | >47.23 | |
| 13 | 25.56 | |
| 78 | 13.47 | |
| 79 | 28.25 | |
| 10 | 4.27 | |
| 80 | 4.40 | |
| 81 | 10.05 | |
| 83 | >33.79 | |
| 84 | >33.79 | |
| 85 | 34.54 | |
| 86 | >43.95 | |
| 1 | 6.81 | |
| 87 | >48.13 | |
| 109 | >48.21 | |
| 88 | 3.98 | 3.16 |
| 89 | >44.39 | |
| 90 | >41.36 | |
| 91 | 3.16 | 0.63 |
| 15 | 11.27 | |
| 92 | 4.59 | |
| 16 | 5.99 | 2.39 |
| 26 | >30.85 | 3.09 |
| 93 | 10.83 | 3.05 |
| 94 | 14.99 | 6.70 |
| 95 | 15.22 | 6.06 |
| 96 | 13.86 | 6.19 |
| 97 | 16.25 | 4.08 |
| 98 | 15.62 | 7.83 |
| 9 | 7.58 | 4.78 |
| 99 | >13.31 | >13.31 |
| 19 | >16.08 | >16.08 |
| 100 | >11.28 | >11.28 |
| 2 | 11.29 | 3.57 |
| 3 | 7.10 | 3.56 |
| 101 | >12.04 | 12.04 |
| 110 | >15.03 | >15.03 |
| 102 | 14.58 | 11.58 |
| 103 | >11.93 | >11.93 |
| 104 | 16.92 | 6.74 |
| 20 | 7.50 | 3.76 |
| 17 | 14.32 | 14.32 |
| 105 | 14.49 | 14.49 |
| 106 | 14.37 | 11.42 |
| 22 | >16.31 | 16.31 |
| 107 | >12.96 | 12.96 |
| 24 | 8.38 | 7.47 |
| 108 | >13.67 | >13.67 |
| 25 | 1.59 | 6.34 |

STA B29213 means *Staphylococcus aureus* (ATCC29213);
MSM 607 means *Mycobacterium smegmatis* (ATCC607);
ATCC means American Type Tissue Culture.

The invention claimed is:

1. A compound of formula (Ia) or (Ib):

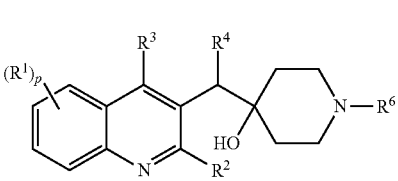

(Ia)

-continued

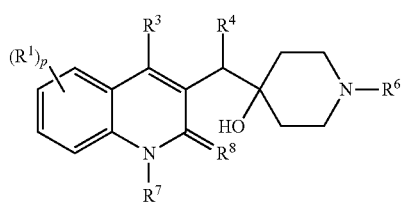
(Ib)

including any stereochemically isomeric form thereof, wherein p is an integer equal to 1, 2, 3 or 4;

$R^1$ is hydrogen, cyano, cyano$C_{1-6}$alkyl, formyl, carboxyl, halo, $C_{1-6}$alkyl, $C_{2-6}$alkenyl, $C_{2-6}$ alkynyl, polyhalo$C_{1-6}$ alkyl, hydroxy, hydroxy$C_{1-6}$ alkyl, $C_{1-6}$alkyloxy, $C_{1-6}$alkyloxy$C_{1-6}$ alkyl, $C_{1-6}$alkylthio, $C_{1-6}$ alkylthio$C_{1-6}$alkyl, —C=N—$OR^{11}$, amino, mono or di($C_{1-6}$ alkyl)amino, amino$C_{1-6}$ alkyl, mono or di($C_{1-6}$ alkyl) amino$C_{1-6}$alkyl, $C_{1-6}$ alkylcarbonylamino$C_{1-6}$ alkyl, $R^{9b}R^{10b}$N—C(O)—, aryl$C_{1-6}$alkyl, arylcarbonyl, $R^{9a}R^{10a}$N—$C_{1-6}$alkyl, di(aryl)$C_{1-6}$alkyl, aryl, $C_{3-6}$cycloalkyl, $R^{9a}R^{10a}$N—, $R^{9a}R^{10a}$N—C(=O)—, $C_{1-4}$alkyl-S(=O)$_2$—, or Het;

$R^2$ is hydrogen, $C_{1-6}$alkyloxy, aryl, aryloxy, hydroxy, mercapto, $C_{1-6}$alkyloxy$C_{1-6}$alkyloxy, $C_{1-6}$alkylthio, mono or di($C_{1-6}$alkyl)amino, amino, pyrrolidino or a radical of formula

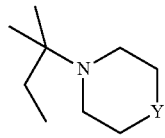

wherein Y is $CH_2$, O, S, NH or N—$C_{1-6}$alkyl;

$R^3$ is hydrogen, halo, $C_{1-6}$alkyl, aryl or Het;

$R^4$ is aryl$^1$ or Het;

$R^6$ is hydrogen, $C_{1-6}$alkyl, aryl$C_{1-6}$alkyl, Het, Het$C_{1-6}$alkyl or —C(=NH)—$NH_2$;

$R^7$ is hydrogen, $C_{1-6}$alkyl or mono or di($C_{1-6}$alkyl)amino;

$R^8$ is oxo; or $R^7$ and $R^8$ together form the radical —CH=CH—N=;

$R^{9a}$ and $R^{10a}$ together with the nitrogen atom to which they are attached form a radical selected from the group consisting of pyrrolidinyl, piperidinyl, piperazinyl, morpholinyl, 4-thiomorpholinyl, 2,3-dihydroisoindol-1-yl, thiazolidin-3-yl, 1,2,3,6-tetrahydropyridyl, hexahydro-1H-azepinyl, hexahydro-1H-1,4-diazepinyl, hexahydro-1,4-oxazepinyl, 1,2,3,4-tetrahydroisoquinolin-2-yl, pyrrolinyl, pyrrolyl, imidazolidinyl, pyrazolidinyl, 2-imidazolinyl, 2-pyrazolinyl, imidazolyl, pyrazolyl, triazolyl, pyridinyl, pyridazinyl, pyrimidinyl, pyrazinyl and triazinyl, each radical being optionally substituted with 1, 2, 3 or 4 substituents, each substituent being independently selected from $C_{1-6}$alkyl, polyhalo$C_{1-6}$ alkyl, halo, aryl$C_{1-6}$alkyl, hydroxy, $C_{1-6}$alkyloxy, amino, mono- or di($C_{1-6}$alkyl)amino, $C_{1-6}$alkylthio, $C_{1-6}$alkylthio$C_{1-6}$alkyl, aryl, pyridyl or pyrimidinyl;

$R^{9b}$ and $R^{10b}$ each independently represent hydrogen, $C_{1-6}$alkyl, aryl or Het;

$R^{11}$ is hydrogen or $C_{1-6}$alkyl;

aryl is a homocycle selected from phenyl, naphthyl, acenaphthyl or tetrahydronaphthyl, each being optionally substituted with 1, 2 or 3 substituents, each substituent being independently selected from hydroxy, hydroxy$C_{1-6}$alkyl, halo, cyano, cyano$C_{1-6}$ alkyl, nitro, amino, mono- or di($C_{1-6}$alkyl)amino, $C_{1-6}$ alkyl, $C_{2-6}$alkenyl optionally substituted with phenyl, polyhalo$C_{1-6}$alkyl, $C_{1-6}$alkyloxy, $C_{1-6}$ alkyloxy$C_{1-6}$ alkyl, polyhalo$C_{1-6}$ alkyloxy, carboxyl, $C_{1-6}$ alkyloxycarbonyl, aminocarbonyl, morpholinyl or mono- or di($C_{1-6}$ alkyl)aminocarbonyl;

aryl$^1$ is a homocycle selected from phenyl, naphthyl, acenaphthyl or tetrahydronaphthyl, each being optionally substituted with 1, 2 or 3 substituents, each substituent being independently selected from hydroxy, hydroxy$C_{1-6}$alkyl, halo, cyano, cyano$C_{1-6}$ alkyl, nitro, amino, mono- or di($C_{1-6}$alkyl)amino, $C_{1-6}$ alkyl, polyhalo$C_{1-6}$alkyl, $C_{1-6}$alkyloxy, $C_{1-6}$ alkyloxy$C_{1-6}$alkyl, $C_{1-6}$ alkylthio, polyhalo$C_{1-6}$alkyloxy, carboxyl, $C_{1-6}$alkyloxycarbonyl, aminocarbonyl, Het, mono- or di($C_{1-6}$ alkyl)aminocarbonyl, or $C_{1-4}$ alkyl-S(=O)$_2$—;

Het is a monocyclic heterocycle selected from N-phenoxypiperidinyl, piperidinyl, piperazinyl, morpholinyl, 4-thiomorpholinyl, pyrrolyl, pyrazolyl, imidazolyl, furanyl, thienyl, oxazolyl, isoxazolyl, thiazolyl, isothiazolyl, pyridinyl, pyrimidinyl, pyrazinyl or pyridazinyl; or a bicyclic heterocycle selected from quinolinyl, quinoxalinyl, indolyl, benzimidazolyl, benzoxazolyl, benzisoxazolyl, benzothiazolyl, benzisothiazolyl, benzofuranyl, benzothienyl, 2,3-dihydrobenzo[1,4]dioxinyl or benzo[1,3]dioxolyl; each monocyclic and bicyclic heterocycle being optionally substituted with 1, 2 or 3 substituents, each substituent being independently selected from halo, hydroxy, $C_{1-6}$alkyl, $C_1$-6alkyloxy or aryl$C_{1-6}$alkyl;

the N-oxides thereof, the pharmaceutically acceptable salts thereof or the solvates thereof.

2. A compound according to claim 1 wherein $R^1$ is halo, $C_{1-4}$alkyl-S(=O)$_2$— or Het.

3. A compound according to claim 1 wherein p is 1.

4. A compound according to claim 1 wherein $R^2$ is $C_{1-6}$alkyloxy or a radical of formula

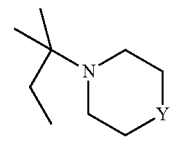

wherein Y is O.

5. A compound according to claim 1 wherein $R^3$ is hydrogen.

6. A compound according to claim 1 wherein $R^4$ is phenyl optionally substituted with 1 substituent, said substituent being selected from halo, cyano or $C_{1-4}$alkyl-S(=O)$_2$—.

7. A compound according to claim 1 wherein $R^4$ is naphthyl.

8. A compound according to claim 1 wherein $R^6$ is hydrogen, $C_{1-6}$alkyl, phenyl$C_{1-6}$alkyl or —C(=NH)—$NH_2$.

9. A compound according to claim 1 wherein $R^7$ is hydrogen and $R^8$ is oxo.

10. A compound according to claim 1 wherein the compound is a compound of formula (Ia).

11. A compound according to claim 1 wherein $R^1$ is placed in position 6 of the quinoline ring.

12. A compound according to claim 1 wherein aryl is phenyl, optionally substituted with one or two substituents each being independently selected from halo; cyano; alkyl; or alkyloxy.

13. A compound according to claim 1 wherein Het is piperdinyl, furanyl, pyridinyl, benzofuranyl or benzo[1,3]dioxolyl.

14. A compound according to claim 1 wherein p is 1;
$R^1$ is halo; $C_{1-6}$alkylthio; $C_{1-4}$alkyl-S(=O)$_2$; or Het;
$R^2$ is $C_{1-6}$alkyloxy, or morpholinyl;
$R^3$ is hydrogen;
$R^4$ is phenyl optionally substituted with halo, cyano or $C_{1-4}$alkyl-S(=O)$_2$—, in either the 3- or 4-position; and
$R^6$ is hydrogen, $C_{1-6}$alkyl, phenyl$C_{1-6}$alkyl, or —C(=NH)—NH$_2$.

15. A compound according to claim 1 wherein the compound is selected from the following compounds:

Comp. No.25

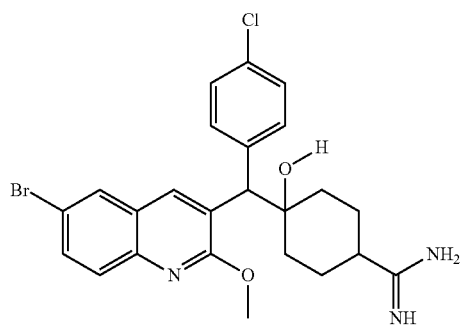

Comp. No.10

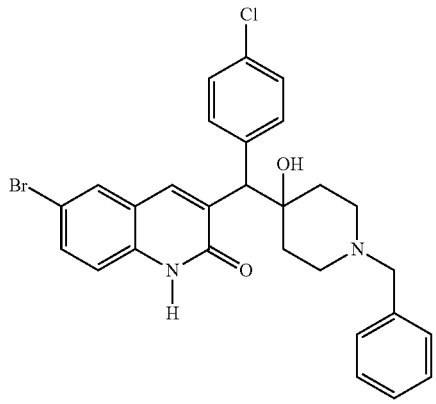

Comp. No.80

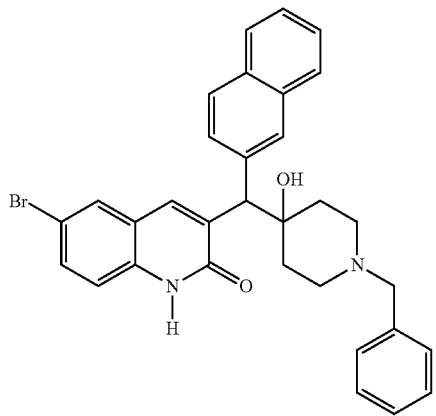

-continued

Comp. No.16

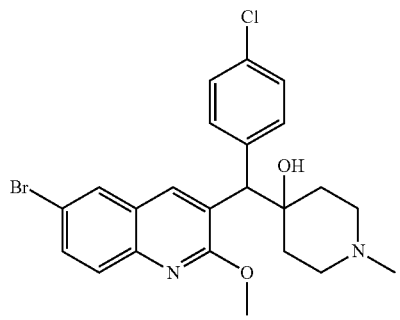

Comp. No.1

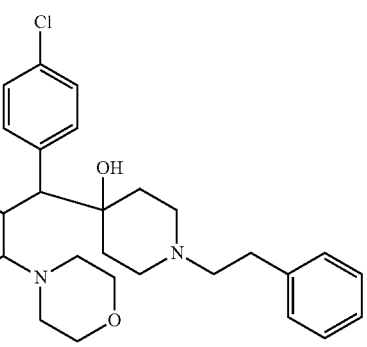

Comp. No.3

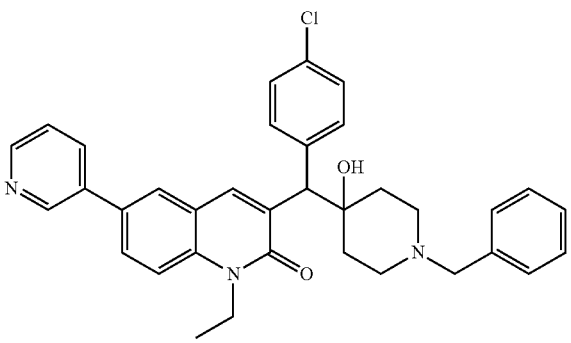

Comp. No.20

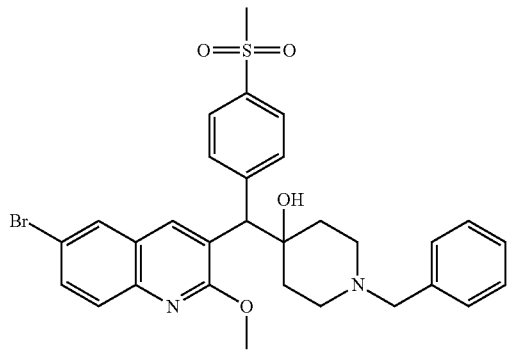

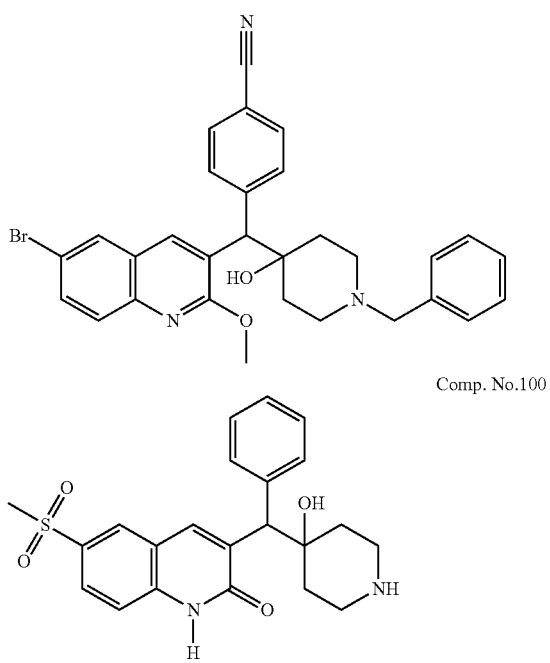

including any stereochemically isomeric form thereof; a N-oxide thereof, a pharmaceutically acceptable salt thereof or a solvate thereof.

16. A method for treating a patient with a bacterial infection comprising administering to said patient an effective amount of a compound according to claim 1.

17. A pharmaceutical composition comprising a pharmaceutically acceptable carrier and, as active ingredient, a therapeutically effective amount of a compound as defined in claim 1.

18. A method according to claim 16 wherein the bacterial infection is an infection with a gram-positive bacterium.

19. A method according to claim 18 wherein the gram-positive bacterium is *Staphylococcus aureus*.

20. A method according to claim 18 wherein the gram-positive bacterium is methicillin-resistant *Staphylococcus aureus*.

21. A method according to claim 16 wherein the bacterial infection is a mycobacterial infection.

22. A method according to claim 12 wherein the mycobacterial infection is an infection with *Mycobacterium tuberculosis*.

23. A combination of (a) a compound according to claim 1, and (b) one or more other antibacterial agents.

24. A product containing (a) a compound according to claim 1, and (b) one or more other antibacterial agents, as a combined preparation for simultaneous, separate or sequential use in the treatment of a bacterial infection.

25. A process for the preparation of a compound according to claim 1 characterized by:

a) deprotecting an intermediate of formula (II-a) wherein $P^1$ is a suitable protecting group

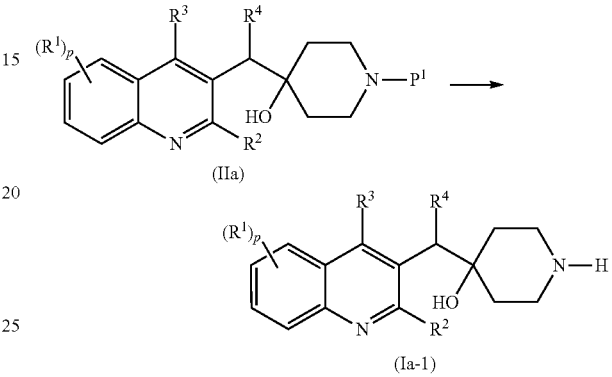

to prepare compounds of formula (Ia) wherein $R^6$ is hydrogen, said compounds being represented by formula (Ia-1);

b) deprotecting an intermediate of formula (IIa) with a suitable acid

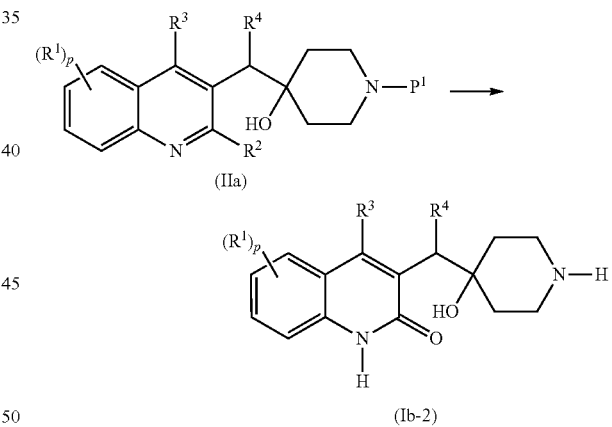

to prepare compounds of formula (Ib) wherein $R^6$ is hydrogen, $R^7$ is hydrogen and $R^8$ is oxo, said compounds being represented by formula (Ib-2); or c) reacting an intermediate of formula (Va) with a compound of formula (VIa)

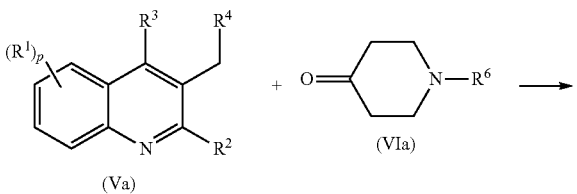

-continued

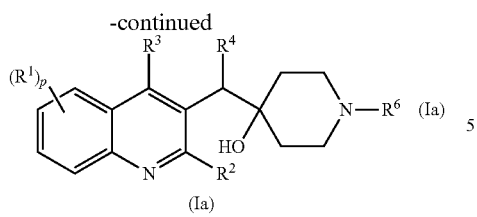

(Ia)

to prepare compounds of formula (Ia);
or, if desired, converting compounds of formula (Ia) or (Ib) into each other following art-known transformations, and further, if desired, converting the compounds of formula (Ia) or (Ib), into a therapeutically active non-toxic acid addition salt by treatment with an acid, or into a therapeutically active non-toxic base addition salt by treatment with a base, or conversely, converting the acid addition salt form into the free base by treatment with alkali, or converting the base addition salt into the free acid by treatment with acid; and, if desired, preparing stereochemically isomeric forms or N-oxide forms thereof.

* * * * *